(12) United States Patent
Xu et al.

(10) Patent No.: US 9,554,971 B2
(45) Date of Patent: Jan. 31, 2017

(54) NANOSTRUCTURED ANTIBACTERIAL AND REMINERALIZING DENTAL BONDING AGENTS AND DENTAL BONDING SYSTEMS

(71) Applicant: UNIVERSITY OF MARYLAND, BALTIMORE, Baltimore, MD (US)

(72) Inventors: Huakun Xu, Frederick, MD (US); Michael Weir, Silver Spring, MD (US)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 29 days.

(21) Appl. No.: 14/377,313

(22) PCT Filed: Feb. 8, 2013

(86) PCT No.: PCT/US2013/025270
§ 371 (c)(1),
(2) Date: Aug. 7, 2014

(87) PCT Pub. No.: WO2013/119901
PCT Pub. Date: Aug. 15, 2013

(65) Prior Publication Data
US 2016/0058675 A1    Mar. 3, 2016

Related U.S. Application Data

(60) Provisional application No. 61/597,345, filed on Feb. 10, 2012, provisional application No. 61/714,520, filed on Oct. 16, 2012.

(51) Int. Cl.
*A61K 6/00* (2006.01)
*A61K 6/02* (2006.01)

(52) U.S. Cl.
CPC ........... *A61K 6/0067* (2013.01); *A61K 6/0023* (2013.01); *A61K 6/02* (2013.01); *A61K 6/024* (2013.01); *A61K 6/0235* (2013.01)

(58) Field of Classification Search
CPC .... A61K 6/0067; A61K 6/0235; A61K 6/024; A61K 6/0023; A61K 6/02
See application file for complete search history.

(56) References Cited

U.S. PATENT DOCUMENTS

| 2002/0035169 | A1 | 3/2002 | Nakatsuka et al. |
| 2008/0306168 | A1 | 12/2008 | Craig et al. |
| 2009/0093563 | A1* | 4/2009 | Qian ............... A61K 6/0029 522/79 |
| 2009/0208909 | A1 | 8/2009 | Rusin et al. |
| 2009/0304809 | A1 | 12/2009 | Rusin et al. |
| 2010/0260849 | A1* | 10/2010 | Rusin ............... A61K 6/083 424/486 |

FOREIGN PATENT DOCUMENTS

| JP | 59-130806 | * 7/1984 | ............... A61K 6/08 |
| WO | 99/42079 | 8/1999 | |
| WO | 2012/003290 | 1/2012 | |

OTHER PUBLICATIONS

Yamauchi (JP59-130806) Machine Translation.*
Extended European Search Report issued Jul. 27, 2015 in corresponding European Application No. 13746175.2.
International Search Report for PCT/US2013/025270, dated Jun. 2, 2013.

* cited by examiner

*Primary Examiner* — Sean Basquill
(74) *Attorney, Agent, or Firm* — Wenderoth, Lind & Ponack, L.L.P.

(57) ABSTRACT

The present invention provides dental bonding agents and dental bonding systems comprising the dental bonding agents. The dental bonding agents of the invention are characterized by having antibacterial properties, and in some aspects of the invention, remineralizing properties.

14 Claims, 27 Drawing Sheets

NANOSTRUCTURED ANTIBACTERIAL AND REMINERALIZING DENTAL BONDING AGENTS AND DENTAL BONDING SYSTEMS

STATEMENT REGARDING FEDERALLY SPONSORED RESEARCH

This invention was made with government support under Grant Number DE017974 awarded by the National Institutes of Health. The government has certain rights in the invention.

BACKGROUND

Tooth caries are the result of a dietary carbohydrate-modified bacterial infectious disease, one of the most common bacterial infections in humans (Loesche, 1986; van Houte, 1994; Featherstone, 2000). The basic mechanism of dental caries is demineralization, or mineral loss, through attack by acid generated by bacteria (Featherstone, 2004; Deng, 2005; Totiam et al., 2007). Therefore, acidogenic bacteria growth, typically in the context of plaque and biofilm formation, is responsible for dental caries (Loesche, 1986; van Houte, 1994; Zero, 1995; Featherstone, 2000; Deng et al., 2005; Cenci et al., 2009). Plaque formation has been described to have three steps: pellicle formation, bacteria colonization, and biofilm maturation (Burne, 1998). In the initial stage, a proteinaceous film called pellicle forms on the tooth surface with adsorbed components from saliva, mucosa, and bacteria (Carlén et al., 2001). Bacteria then adhere and colonize on this surface to grow into a biofilm, which is a heterogeneous structure consisting of clusters of various types of bacteria embedded in an extracellular matrix (Stoodley et al., 2008). Cariogenic bacteria such as *Streptococcus mutans* (*S. mutans*) and lactobacilli in the plaque can take nutrients from carbohydrates and produce organic acids. Acid production causes demineralization to the tooth structure beneath the biofilm.

Resin composites have been increasingly used for tooth cavity restorations because of their aesthetics, direct-filling capability, and enhanced performance (Ferracane, 1995; Bayne et al., 1998; Lim et al., 2002; Ruddell et al., 2002; Watts et al., 2003; Drummond, 2008). While there has been significant improvement in resin compositions, filler types, and cure conditions since their introduction (Ruddell et al., 2002; Imazato, 2003; Drummond and Bapna, 2003; Watts et al., 2003; Lu et al., 2005; Xu X et al., 2006; Krämer et al., 2006), formation of secondary caries and bulk fracture remain challenges to the use of resins (Sarrett, 2005; Sakaguchi, 2005). Indeed, resin composites generally do not prevent secondary caries because they do not hinder bacteria colonization and plaque formation. In fact, several studies have indicated that resin composites have a greater accumulation of bacteria and plaque than other restorative materials (Svanberg et al., 1990; Imazato et al., 1994; Takahashi et al., 2004). Indeed, caries at the restoration margins are a frequent reason for replacing existing restorations (Mjör et al., 2000), accounting for 50-70% of all restorations (Deligeorgi et al., 2001; Frost, 2002).

Secondary caries may form in the tooth-restoration interface. Dental bonding systems are used to adhere resin composites to tooth structures (Spencer and Wang, 2002; Park et al., 2009; Pashley et al., 2011), but microleakage can allow bacteria to invade the interface. Residual bacteria can also exist in a clean tooth cavity prior to being packed with the resin composition.

Dental bonding systems that possess antibacterial properties could prove useful as an additional means of inhibiting the development of secondary caries by preventing the growth of residual and invading bacteria. Such antibacterial dental bonding systems would also find use in other applications to which dental bonding is employed, including dentin bonding, enamel bonding, tooth roots, marginal repair, as a crown cement, as an inlay/onlay cement, as a pit and fissure sealant, and as an orthodontic bracket adhesive or cement.

SUMMARY

The present invention provides dental bonding agents and dental bonding systems comprising the dental bonding agents. The dental bonding agents of the invention are characterized by having antibacterial properties, and in some aspects of the invention, remineralizing properties.

Dental bonding systems employing the dental bonding agents of the invention can be used in a variety of applications where a bond between two components is required in a dental application. For example, the bonding systems can be prepared for use in dentin bonding, enamel bonding, tooth roots, marginal repair, as a crown cement, as an inlay/onlay cement, as a pit and fissure sealant, and as an orthodontic bracket adhesive or cement. As a specific example, the dental bonding systems can be used in conjunction with resin composites that are used to fill voids in teeth after removal of decayed materials. The dental bonding systems of the invention include a two-component system comprising a dental primer and a dental adhesive, a three-step bonding system, a two-step bonding system, and a one-step self-adhesive bonding system.

The dental bonding agents of the invention include dental primers and dental adhesives. As suggested above, the dental primers and the dental adhesives are characterized as having antibacterial properties. These properties are imparted by one or more antibacterial agents that are included in the dental primers and dental adhesives. In certain aspects of the invention, the dental primers and dental adhesives may also have remineralizing properties.

Therefore, in a first embodiment the present invention includes a dental primer comprising a primer and one or more antibacterial agents. In one aspect, the dental primer further comprises a remineralizing agent.

In a second embodiment, the invention includes a dental adhesive comprising a adhesive and one or more antibacterial agents. In one aspect, the dental adhesive further comprises a remineralizing agent.

In a third embodiment, the invention includes a dental bonding system comprising (i) a dental primer and (ii) a dental adhesive, wherein the dental primer comprises a primer and one or more antibacterial agents and wherein the dental adhesive comprises an adhesive and one or more antibacterial agents. In certain aspects, one or both of the dental primer and the dental adhesive further comprises a remineralizing agent. In certain aspects, the system further comprises an etchant.

In one aspect, the dental bonding system is a two-component dental bonding system comprising (i) a dental primer and (ii) a dental adhesive, wherein the dental primer comprises a primer and one or more antibacterial agents and wherein the dental adhesive comprises an adhesive and one or more antibacterial agents. In certain aspects, one or both of the dental primer and the dental adhesive further comprises a remineralizing agent. In certain aspects, the system further comprises an etchant.

In another aspect, the dental bonding system is three-step dental bonding system comprising (i) an etchant, (ii) a dental primer, and (iii) a dental adhesive, wherein the dental primer comprises a primer and one or more antibacterial agents and wherein the dental adhesive comprises an adhesive and one or more antibacterial agents. In certain aspects, one or both of the dental primer and the dental adhesive further comprises a remineralizing agent.

In a further aspect, the dental bonding system is two-step dental bonding system comprising (i) an etchant, and (ii) a mixture comprising a dental primer and a dental adhesive, wherein the dental primer comprises a primer and one or more antibacterial agents and wherein the dental adhesive comprises an adhesive and one or more antibacterial agents. In certain aspects, one or both of the dental primer and the dental adhesive further comprises a remineralizing agent.

In an additional aspect, the dental bonding system is one-step self-adhesive bonding system comprising a mixture that comprises an etchant, a dental primer, and a dental adhesive, wherein the dental primer comprises a primer and one or more antibacterial agents and wherein the dental adhesive comprises an adhesive and one or more antibacterial agents. In certain aspects, one or both of the dental primer and the dental adhesive further comprises a remineralizing agent.

In each of the embodiments of the present invention, the dental primer comprises (i) one or more primers, and (ii) one or more antibacterial agents. The primers include, but are not limited to, those comprising Bisphenol A diglycidyl methacrylate (Bis-GMA), glycerol dimethacrylate (GDMA), 2-hydroxyethyl methacrylate (HEMA), mono-2-methacryloyloxyethyl phthalate (MMEP), methacrylic acid (MA), methyl methacrylate (MMA), 4-acryloyloxyethyl trimellitate anhydride (4-AETA), N-phenylglycine glycidyl methacrylate (NPG-GMA), N-tolylglycine glycidyl methacrylate or N-(2-hydroxy-3-((2-methyl-1-oxo-2-propenyl)oxy)propyl)-N-tolyl glycine (NTG-GMA), pyromellitic diethylmethacrylate or 2,5-dimethacryloyloxyethyloxycarbonyl-1,4-benzenedicarboxylic acid (PMDM), pyromellitic glycerol dimethacrylate or 2,5-bis(1,3-dimethacryloyloxyprop-2-yloxycarbonyl)benzene-1,4-dicarboxylic acid (PMGDM), and triethylene glycol dimethacrylate (TEGDMA). In certain aspects, the primer comprises SCOTCHBOND MULTI-PURPOSE™ (SBMP) primer comprising 35-45% 2-hydroxyethylmethacrylate (HEMA), 10-20% copolymer of acrylic and itaconic acids, 40-50% water. In certain other aspects, the primer comprises PMGDM/HEMA at 3.3/1 ratio+1% BAPO+50% acetone.

In each of the embodiments of the present invention, the dental adhesive comprises (i) one or more adhesives, and (ii) one or more antibacterial agents. The adhesives include, but are not limited to, those comprising ethoxylated bisphenol A glycol dimethacrylate (Bis-EMA), bisphenol A diglycidyl methacrylate (Bis-GMA), 2-hydroxyethyl methacrylate (HEMA), triethylene glycol dimethacrylate (TEGDMA), urethane dimethacrylate (UDMA), 4-methacryloyloxyethyl trimellitate anhydride (4-META), methacrylic acid (MA), methyl methacrylate (MMA), 4-acryloyloxyethyl trimellitate anhydride (4-AETA), ethyleneglycol dimethacrylate (EGDMA), glycerol dimethacrylate (GDMA), glycerol phosphate dimethacrylate (GPDM), pyromellitic glycerol dimethacrylate or 2,5-bis(1,3-dimethacryloyloxyprop-2-yloxycarbonyl)benzene-1,4-dicarboxylic acid (PMGDM). In certain aspects, the adhesive comprises SBMP adhesive comprising 60-70% BisGMA and 30-40% HEM. In certain other aspects, the adhesive comprises BisGMA/TEGMA at 7/3 ratio+1% BAPO.

The antibacterial agents included in the dental primers and dental adhesive of the invention include, but are not limited to, antibacterial monomers, silver-containing nanoparticles (NAg), quaternary ammonium salts (QAS), chlorhexidine particles, TiO2 particles and ZnO particles.

The antibacterial monomers include dimethylamino propyl methacrylate (DMAPM), dimethylamino hexyl methacrylate (DMAHM), dimethylamino heptyl methacrylate (DMAHPM), dimethylamino octyl methacrylate (DMAOM), dimethylamino nonyl methacrylate (DMANM), dimethylamino decyl methacrylate (DMADM), dimethylamino undecyl methacrylate (DMAUDM), dimethylamino dodecyl methacrylate (DMADDM), dimethylamino tridecyl methacrylate (DMATDM), dimethylamino tetradecyl methacrylate (DMATTDM), dimethylamino pentadecyl methacrylate (DMAPDM), dimethylamino hexadecyl methacrylate (DMAHDM), dimethylamino heptadecyl methacrylate (DMAHPDM), dimethylamino octadecyl methacrylate (DMAODM), dimethylamino nonadecyl methacrylate (DMANDM), dimethylamino icosyl methacrylate (DMAIOM), dimethylamino henicosyl methacrylate (DMAHOM), and dimethylamino docosyl methacrylate (DMADOM). In certain aspects, the antibacterial monomer is DMADDM, DMATDM, DMATTDM, DMAPDM or DMAHDM.

In certain aspects of the invention, the combined amount of the one or more antibacterial monomers incorporated into the dental primer or dental adhesive ranges from about 1% to about 50% of the mass of the dental primer or the dental adhesive. In particular aspects, the combined amount of the one or more antibacterial monomers present in the dental primer or dental adhesive is about 10%, 7.5%, or 5% of the mass of the dental primer or dental adhesive.

In certain aspects of the invention, the amount of NAg present in the dental primer or dental adhesive ranges from about 0.05% and about 5% of the mass of the dental primer or dental adhesive. In particular aspects, the amount of NAg present in the dental primer or dental adhesive is a mass fraction of about 0.1%, 0.25%, or 0.5%.

When present, quaternary ammonium salts may be a mass fraction of between about 1% to 50% of the mass of the dental primer or dental adhesive, preferably about 3% to about 15% of the mass of the dental primer or dental adhesive.

In embodiments where the dental primer or dental adhesive comprises a remineralizing agent, such agents include, but are not limited to, nanoparticles of amorphous calcium phosphate (NACP). In certain aspects of the invention, the amount of NACP included in the dental primers and dental adhesives ranges from about 10% to about 40% of the mass of the dental primer or dental adhesive. In particular aspects, the mass fraction of NACP in the dental primer or dental adhesive is about 20% or about 30%.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BEMA=2-bromoethyl methacrylate. DMAHM=dimethylaminohexane methacrylate. DMAD=1-(dimethylamino)docecane. DMADDM=dimethylaminododecyl methacrylate. EtOH=anhydrous ethanol. The number of the alkyl chain length units was 6 for DMAHM and 12 for DMADDM.

FIGS. 17A-B. FTIR spectra of reactants and products for: (A) DMAHM, and (B) DMADDM.

FIGS. 18A-B. Mechanical properties of composites: (A) flexural strength, and (B) elastic modulus (mean±sd; n=6). NACP+ODMADDM refers to NACP nanocomposite containing 0% DMADDM; NACP+0.75DMADDM refers to NACP nanocomposite containing 0.75% of DMADDM; and so on. Adding up to 3% of DMADDM into NACP nanocomposite resulted in no significant decrease in strength and elastic modulus. Horizontal line indicates values that are not significantly different from each other ($p>0.1$).

FIGS. 19A-B. Dental plaque microcosm biofilms adherent on composites: (A) MTT metabolic activity, and (B) lactic acid production (mean±sd; n=6). NACP+ODMADDM refers to NACP nanocomposite containing 0% DMADDM; NACP+0.75DMADDM refers to NACP nanocomposite containing 0.75% of DMADDM; and so on. In each plot, values with dissimilar letters are significantly different ($p<0.05$).

FIGS. 20A-C. Colony-forming unit (CFU) counts for: (A) Total microorganisms, (B) total streptococci, and (C) *mutans* streptococci (mean±sd; n=6). NACP+ODMADDM refers to NACP nanocomposite containing 0% DMADDM; NACP+0.75DMADDM refers to NACP nanocomposite containing 0.75% of DMADDM; and so on. In each plot, values with dissimilar letters are significantly different ($p<0.05$). Note the log scale for the y-axis.

Figure 21:
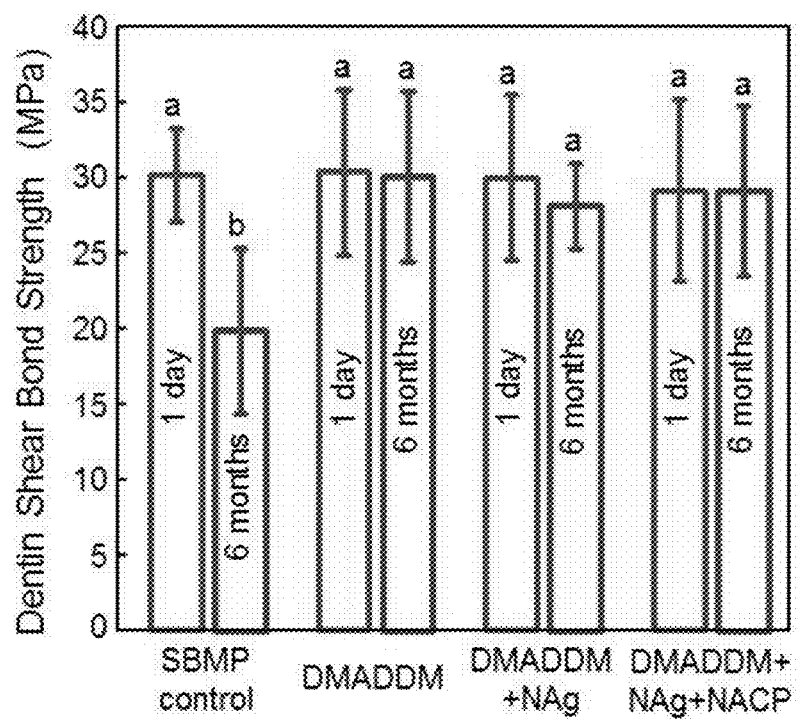

FIG. 21. Measurement of dentin shear bond strength. Extracted human molar teeth were used (n=10). Monomer DMADDM and nanoparticles of silver (NAg) were incorporated into a commercial bonding agent SBMP. The bonded dentin samples were immersed in water for 1 day and 6 months, to test the degradation of bond strength over time. The commercial control lost ⅓ of its strength in 6 months.

Figure 22:
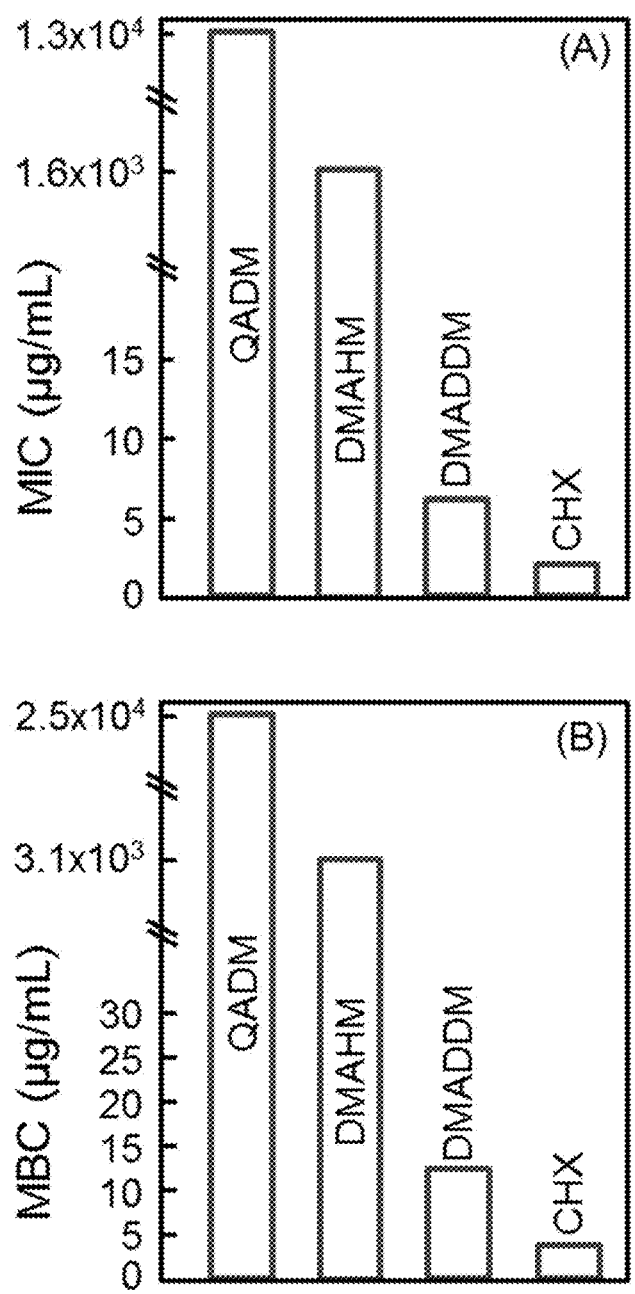

FIG. 22. Minimum inhibitory concentration (MIC), and minimum bactericidal concentration (MBC) against *S. mutans*. A lower MIC and MBC indicate a stronger antibacterial potency for the antibacterial agent. CHX had the lowest MIC and MBC. Regarding the two monomers, DMADDM (dimethylaminododecyl methacrylate) with an alkyl chain length of 12 was much more potent than DMAHM (dimethylhexylamine methacrylate) with a chain length of 6. The tests were performed in triplicate (n=3).

Figure 23:
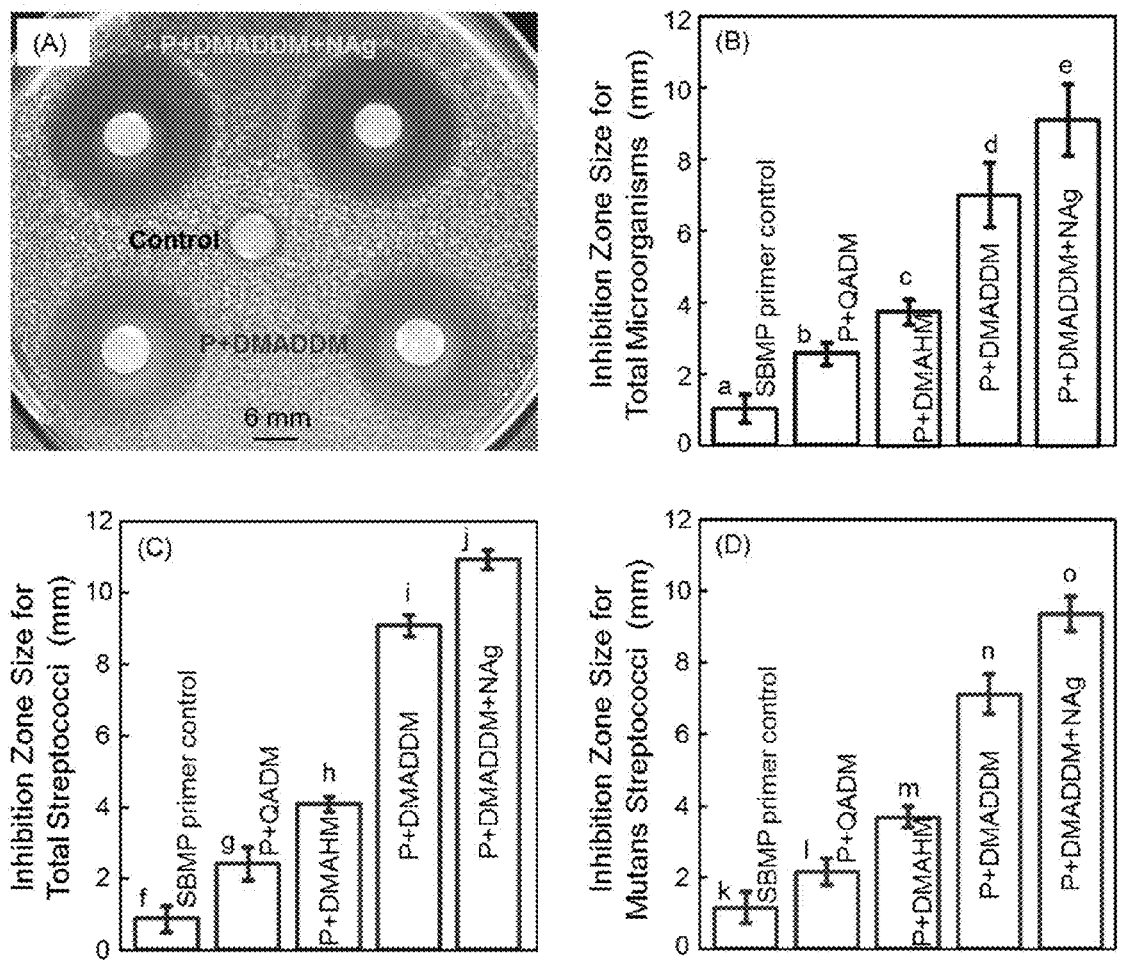

FIG. 23. Antibacterial activity of un-cured primers against human saliva microcosm bacteria in agar disk diffusion test (ADT). In the examples shown in (A), the top two paper disks were impregnated with P+DMADDM+NAg. The middle disk was impregnated with control primer. The two lower disks were impregnated with P+DMADDM. Primer with DMADDM and NAg had strong antibacterial effects against (B) total microorganisms, (C) total streptococci, and (D) *mutans* streptococci. Each value is mean±sd (n=6). In each plot, values with dissimilar letters are different from each other ($p<0.05$).

Figure 24:
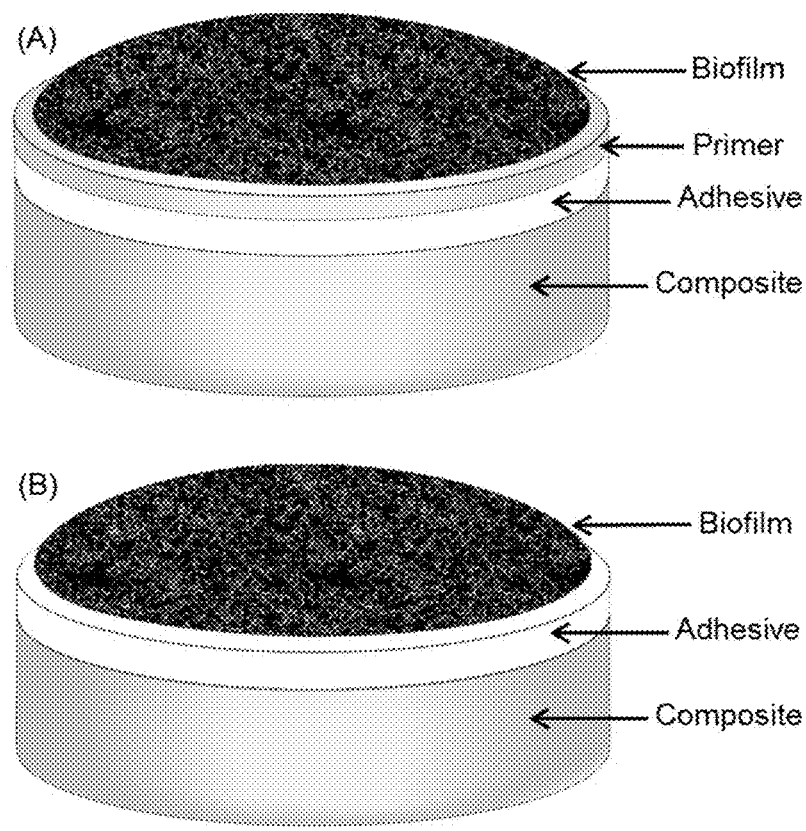
Figure 24:
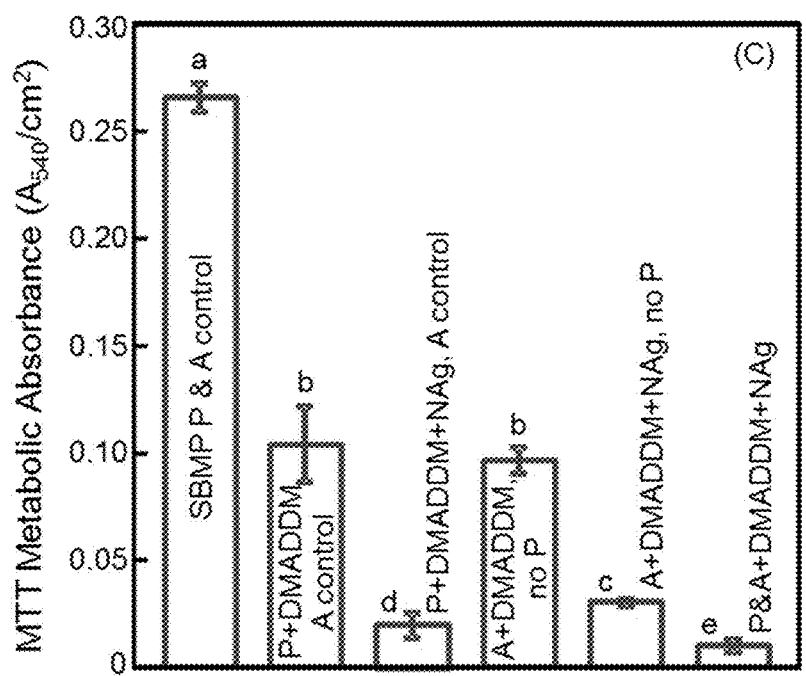

FIG. 24. MTT metabolic activity: (A) Schematic of biofilm on the primer covering the adhesive and composite, (B) biofilm on the adhesive surface covering the composite, and (C) MTT metabolic activity. Biofilms were grown for 2 days using a microcosm model. Groups 1-3, and 6, were tested following schematic of FIG. 24A. Groups 4 and 5 were tested following schematic of FIG. 24B without a primer layer, to investigate the antibacterial activity of the adhesive. Each values is mean±sd (n=6). Values with dissimilar letters are significantly different from each other ($p<0.05$).

Figure 25:
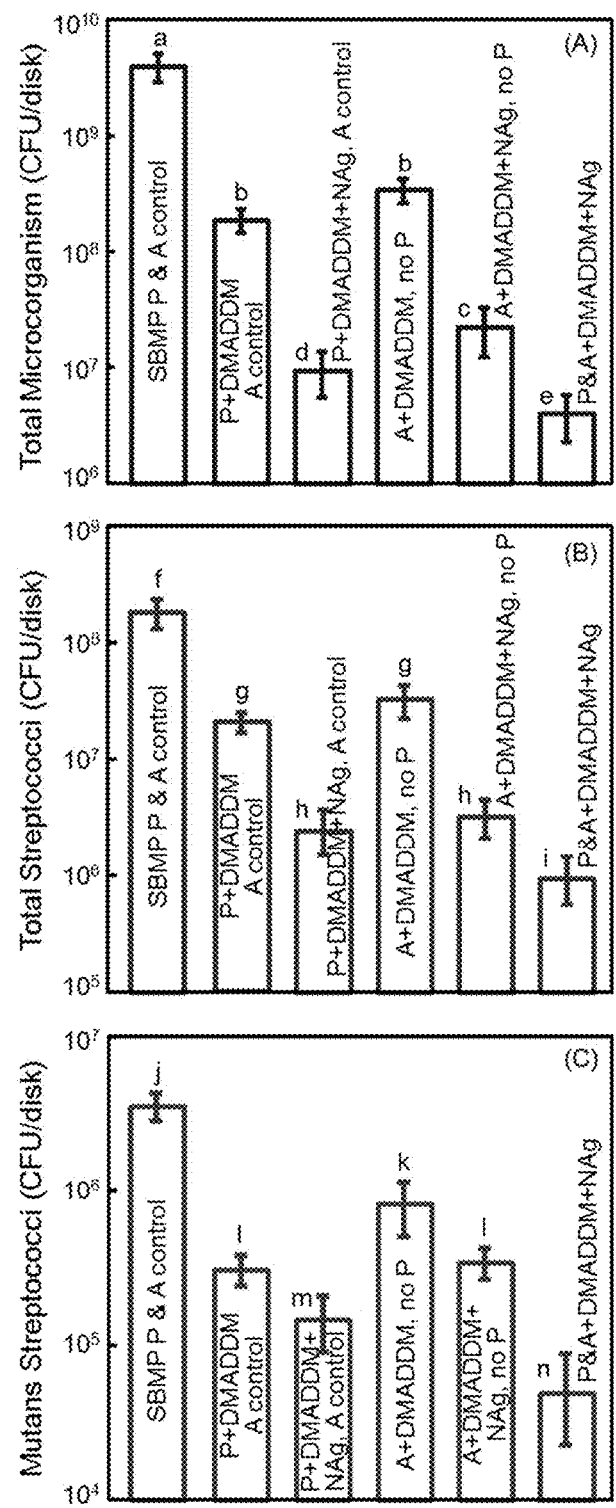

FIG. 25. Biofilm CFU on the cured disks of the six groups for: (A) Total microorganisms, (B) total streptococci, and (C) *mutans* streptococci. Note the log scale for the y-axis. The DMADDM greatly reduced the CFU. Adding DMADDM and NAg together in primer or adhesive was more potent than using DMADDM alone. Each values is mean±sd (n=6). Values with dissimilar letters are significantly different from each other ($p<0.05$).

Figure 26:
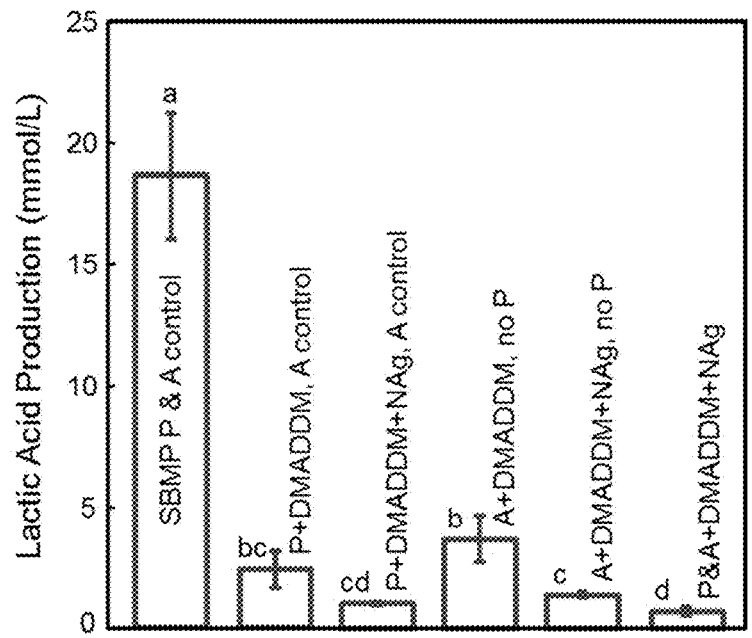

FIG. 26. Lactic acid production by microcosm biofilms adherent on the cured specimens for the six groups. Bars 1-3 are for biofilms on primer, with the adhesive being the unmodified SBMP adhesive. Bars 4 and 5 are for biofilms on the adhesive without a primer. Bar 6 is for primer and adhesive both being antibacterial. Each value is mean±sd (n=6). Values with dissimilar letters are significantly different from each other ($p<0.05$).

Figure 27:
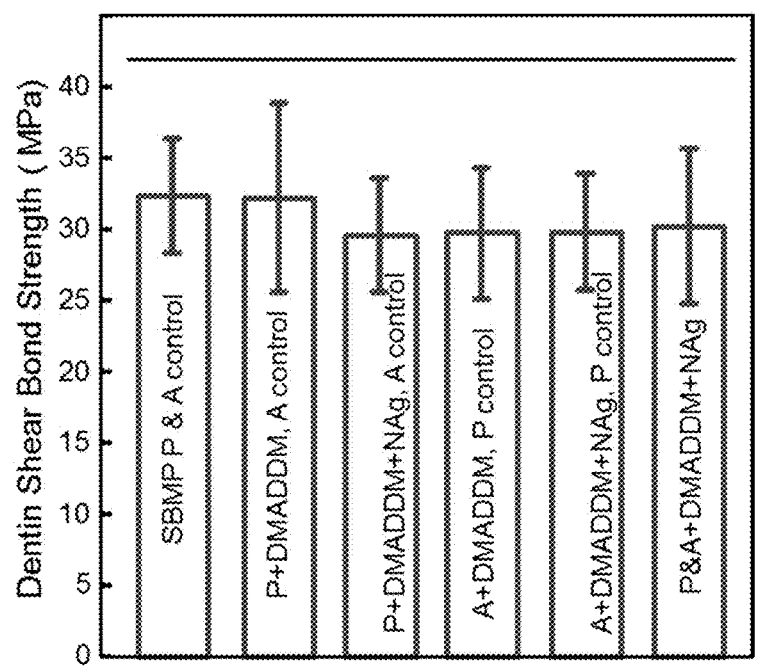

FIG. 27. Dentin shear bond strength. Ten extracted human molars were used for each group, requiring a total of sixty teeth. Each value is mean±sd (n=10). The horizontal line indicates that the dentin shear bond strength was not compromised by adding DMADDM and NAg into primer and adhesive ($p>0.1$).

Figure 28:
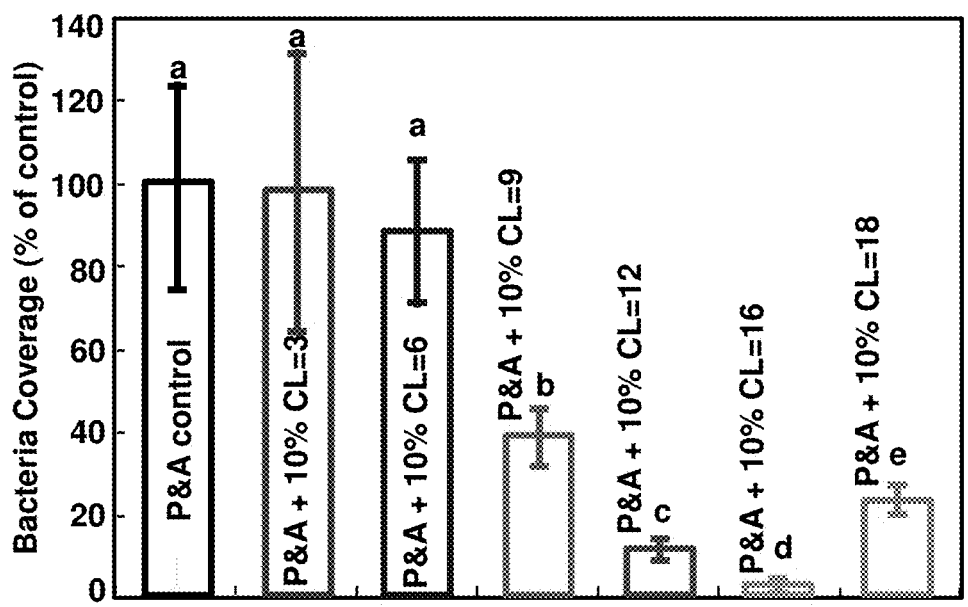

FIG. 28: Effect of antibacterial monomers from Table 1, with chain length (CL) of 3, 6, 9, 12, 16 and 18, on early attachment (4 hour culture) and contact-killing of bacteria. Each monomer was mixed into the primer and adhesive control (P&A control) at 10% mass fraction (mean+−sd; n=6). In the plot, values with dissimilar letters are significantly different from each other ($p<0.05$).

Figure 29:
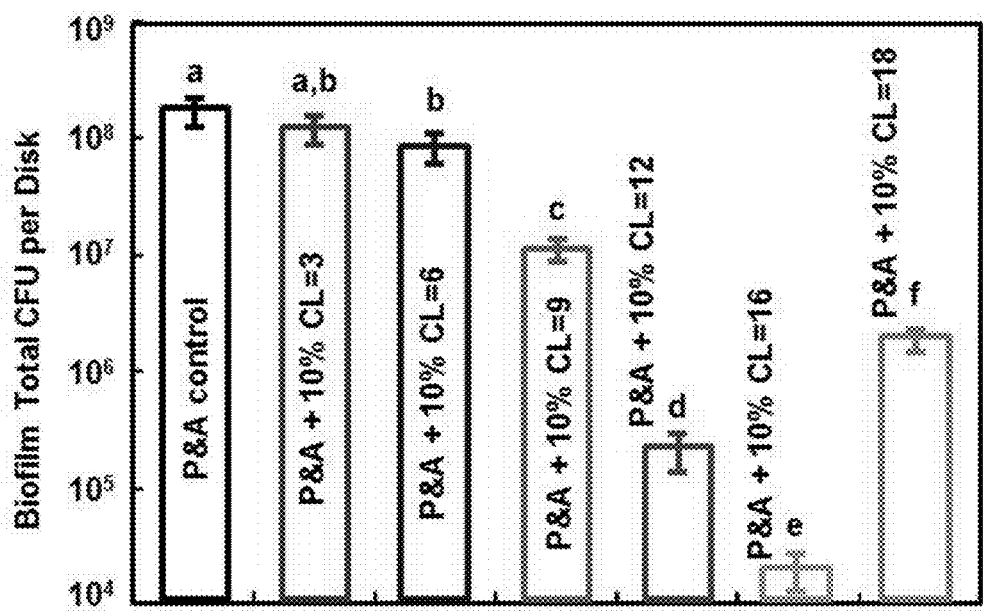

FIG. 29: Effect of antibacterial monomers from Table 1, with chain length (CL) of 3, 6, 9, 12, 16 and 18, on mature biofilms (48 hours). Each monomer was mixed into the primer and adhesive control (P&A control) at 10% mass fraction (mean+−sd; n=6). Values with dissimilar letters are significantly different from each other ($p<0.05$). CL=16 reduced the biofilm CFU by 4 orders of magnitude, compared to control.

Figure 30:
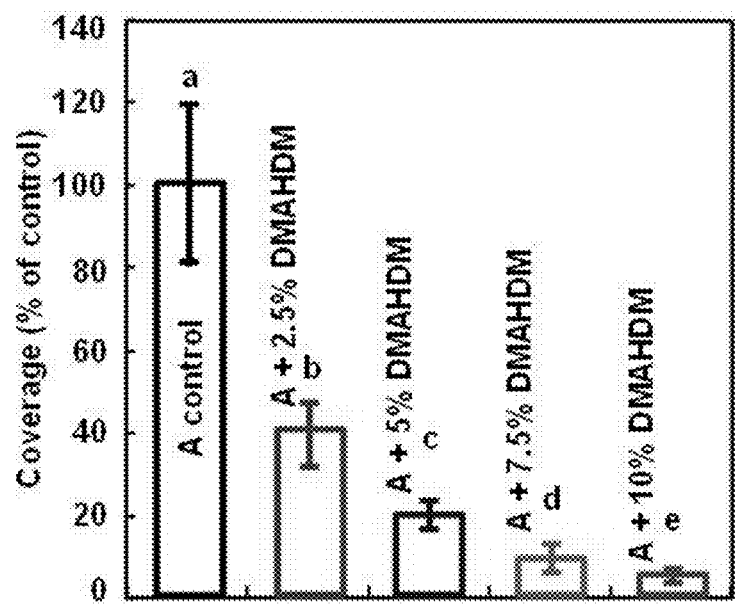

FIG. 30: Effect of mass fraction of the antibacterial monomer DMAHDM (with chain length of 16) on early attachment (4 hour culture) and contact-killing of bacteria (mean+−sd; n=6). In the plot, values with dissimilar letters are significantly different from each other ($p<0.05$).

Figure 31:
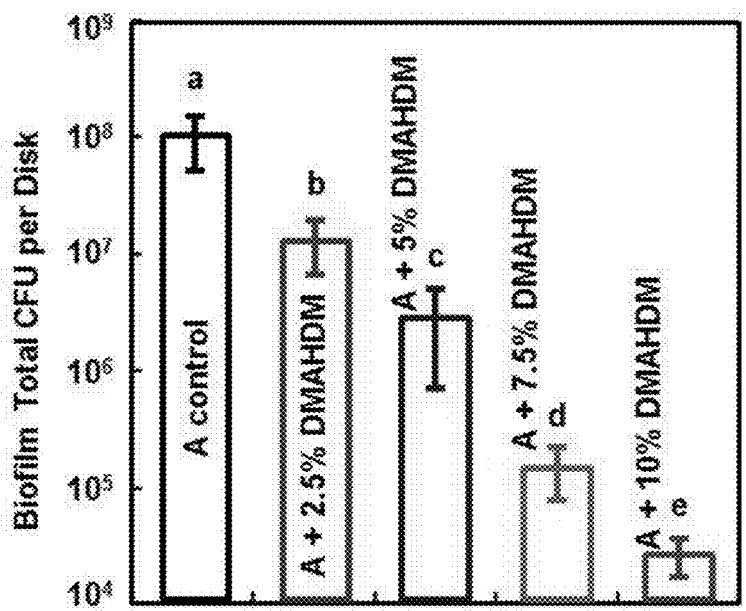

FIG. 31: Effect of mass fraction of the antibacterial monomer DMAHDM (with chain length of 16) on mature biofilms (48 hours) (mean+−sd; n=6). Values with dissimilar letters are significantly different from each other ($p<0.05$). DMAHDM at 10% mass fraction reduced the biofilm CFU by nearly 4 orders of magnitude, compared to control.

DETAILED DESCRIPTION

Described herein are novel dental bonding agents, and dental bonding systems comprising the agents. Dental bonding systems employing the dental bonding agents of the invention can be used in a variety of applications where a bond between two components is required in a dental application. For example, the bonding systems can be prepared for use in dentin bonding, enamel bonding, tooth roots, marginal repair, as a crown cement, as an inlay/onlay cement, as a pit and fissure sealant, and as an orthodontic bracket adhesive or cement.

The dental bonding agents of the invention include dental primers and dental adhesives. Both the dental primers and the dental adhesives are unique in that they have antibacterial properties. These properties are imparted by one or more antibacterial agents that may be included in the dental primers and the dental adhesives. In certain aspects of the invention, the dental primers and dental adhesives may also have remineralizing properties.

The dental primers of the present invention comprise any primer, or combination of primers, that is suitable for dental use in a subject, such as a human, and one or more antibacterial agents. Suitable primers will be those commonly used in dental applications. Exemplary primers comprise Bisphenol A diglycidyl methacrylate (Bis-GMA), glycerol dimethacrylate (GDMA), 2-hydroxyethyl methacrylate (HEMA), mono-2-methacryloyloxyethyl phthalate (MMEP), methacrylic acid (MA), methyl methacrylate (MMA), 4-acryloyloxyethyl trimellitate anhydride (4-AETA), N-phenylglycine glycidyl methacrylate (NPG-GMA), N-tolylglycine glycidyl methacrylate or N-(2-hydroxy-3-((2-methyl-1-oxo-2-propenyl)oxy)propyl)-N-tolyl glycine (NTG-GMA), pyromellitic diethylmethacrylate or 2,5-dimethacryloyloxyethyloxycarbonyl-1,4-benzenedicarboxylic acid (PMDM), pyromellitic glycerol dimethacrylate or 2,5-bis(1,3-dimethacryloyloxyprop-2-yloxycarbonyl)benzene-1,4-dicarboxylic acid (PMGDM), and triethylene glycol dimethacrylate (TEGDMA). In one example, a suitable primer comprises SBMP primer comprising 35-45% 2-hydroxyethylmethacrylate (HEMA), 10-20% copolymer of acrylic and itaconic acids, 40-50% water. In another example, the primer comprises PMGDM/HEMA at 3.3/1 ratio+1% BAPO+50% acetone.

Similarly, the dental adhesives of the present invention comprise any adhesive, or combination of adhesives, that is suitable for dental use in a subject, such as a human, and one or more antibacterial agents. Suitable adhesives will be those commonly used in dental applications. Exemplary adhesives comprise ethoxylated bisphenol A glycol dimethacrylate (Bis-EMA), bisphenol A diglycidyl methacrylate (Bis-GMA), 2-hydroxyethyl methacrylate (HEMA), triethylene glycol dimethacrylate (TEGDMA), urethane dimethacrylate (UDMA), 4-methacryloyloxyethyl trimellitate anhydride (4-META), methacrylic acid (MA), methyl methacrylate (MMA), 4-acryloyloxyethyl trimellitate anhydride (4-AETA), ethyleneglycol dimethacrylate (EGDMA), glycerol dimethacrylate (GDMA), glycerol phosphate dimethacrylate (GPDM), pyromellitic glycerol dimethacrylate or 2,5-bis(1,3-dimethacryloyloxyprop-2-yloxycarbonyl)benzene-1,4-dicarboxylic acid (PMGDM). In one example, a suitable adhesive comprises SBMP adhesive comprising 60-70% BisGMA and 30-40% HEM. In another example, the adhesive comprises BisGMA/TEGMA at 7/3 ratio+1% BAPO.

The antibacterial agents included in the dental primers and dental adhesives of the invention include, but are not limited to, antibacterial monomers, silver-containing nanoparticles (NAg), quaternary ammonium salts (QAS), chlorhexidine particles, TiO2 particles and ZnO particles.

The antibacterial monomers differ based on the length of the alkyl chain and include dimethylamino propyl methacrylate (DMAPM), dimethylamino hexyl methacrylate (DMAHM), dimethylamino heptyl methacrylate (DMAHPM), dimethylamino octyl methacrylate (DMAOM), dimethylamino nonyl methacrylate (DMANM), dimethylamino decyl methacrylate (DMADM), dimethylamino undecyl methacrylate (DMAUDM), dimethylamino dodecyl methacrylate (DMADDM), dimethylamino tridecyl methacrylate (DMATDM), dimethylamino tetradecyl methacrylate (DMATTDM), dimethylamino pentadecyl methacrylate (DMAPDM), dimethylamino hexadecyl methacrylate (DMAHDM), dimethylamino heptadecyl methacrylate (DMAHPDM), dimethylamino octadecyl methacrylate (DMAODM), dimethylamino nonadecyl methacrylate (DMANDM), dimethylamino icosyl methacrylate (DMAIOM), dimethylamino henicosyl methacrylate (DMAHOM), and dimethylamino docosyl methacrylate (DMADOM). The alkyl chain lengths (CL) of the monomers are provided in Table 2 of the Examples. These antibacterial monomers are well suited for use in dental primers and dental adhesives that are used in dental applications. In certain aspects, the antibacterial monomer is DMADDM (alkyl chain length (CL)=12), DMATDM (CL=13), DMATTDM (CL=14), DMAPDM (CL=15), or DMAHDM (CL=16).

The antibacterial monomers can be incorporated into the dental primer or dental adhesive at antibacterial monomer mass fractions ranging from about 0.5% to about 50% of the dental primer or dental adhesive, preferably from about 2% to about 20% of the mass of the dental primer or dental adhesive. In certain aspects, the antibacterial monomers can be incorporated into the dental primer or dental adhesive at antibacterial monomer mass fractions ranging from about 1% to about 50%, from about 1% to about 25%, from about 2% to about 20%, from about 2.5% to about 25%, from about 2.5% to about 20%, from about 2.5% to about 15%, from about 2.5% to about 12.5%, from about 5% to about 25%, from about 5% to about 20%, from about 5% to about 15%, from about 5% to about 10%, from about 7.5% to about 25%, from about 7.5% to about 20%, about 7.5% to about 15% or from about 7.5% to about 12.5% of the mass of the dental primer or dental adhesive. In particular aspects, the amount of the antibacterial monomers present in the dental primer or dental adhesive is a combined amount of about 0.5, 1, 2, 2.5, 3, 4, 5, 6, 7, 7.5, 8, 9, 10, 11, 12, 12.5, 13, 14, 15, 16, 17, 17.5, 18, 19, 20, 21, 22, 22.5, 23, 24, 25, 26, 27, 27.5, 28, 29, 30, 31, 32, 33, 34, 35, 36, 37, 38, 39, 40, 41, 42, 43, 44, 45, 46, 47, 48, 49 or 50% of the mass of the dental primer or dental adhesive. In certain aspects of the invention, the combined amount of the antibacterial monomers incorporated into the dental primer or dental adhesive ranges from about 1% to about 50% of the mass of the dental primer or dental adhesive. In particular aspects, the combined amount of the antibacterial monomers present in the dental primer or dental adhesive is about 10%, 7.5%, or 5% of the mass of the primer or adhesive. In certain aspects, one of the antibacterial monomers identified herein is included in a dental primer or dental adhesive. In certain other aspects, two, three, four, or more of the antibacterial monomers identified herein are included in a dental primer or dental adhesive.

Suitable silver-containing nanoparticles (NAg) include, but are not limited to, silver 2-ethylhexanoate salt, silver-containing glass particles and silver benzoate. In addition to silver salts, pre-formed silver nanoparticles can be used. When present, NAg may make up between about 0.001% and about 20% of a mass fraction of the dental primer or dental adhesive. In certain aspects, NAg will make up between about 0.001% and about 3%, about 0.05% and about 1%, about 0.05% and about 2%, about 0.05% and about 5%, about 0.08% and about 10%, or about 0.1% and about 0.5%, of a mass fraction of the dental primer or dental adhesive, or about 0.01%, 0.08%, 0.15%, 0.20%, 0.25%, 0.30%, 0.35%, 0.40%, 0.45%, 0.50%, 1.0%, 1.5%, 2.0%, 2.5%, 3.0%, 3.5%, 4.0%, 4.5% or 5.0% of a mass fraction of the dental primer or dental adhesive. In one aspect, NAg makes up about 0.1% of a mass fraction of the dental primer or dental adhesive. The silver particle size can range from about 1 nm to about 1000 nm, and in one aspect, from about 2 nm to about 500 nm. In certain aspects, the amount of NAg present in the dental primer or dental adhesive ranges from about 0.05% and about 5% of the mass of the dental primer or dental adhesive. In particular aspects, the amount of NAg present in the dental primer or dental adhesive is a mass fraction of about 0.1%, 0.25%, or 0.5%.

Suitable quaternary ammonium salts (QASs) include both polymerizable monomers and non-polymerizable small molecules, and include, but are not limited to, bis(2-methacryloyloxy-ethyl)dimethyl-ammonium bromide (QADM), methacryloyloxydodecylpyridinium bromide, methacryloxyethyl benzyl dimethyl ammonium chloride, methacryloxyethyl m-chloro benzyl dimethyl ammonium chloride, methacryloxyethyl cetyl dimethyl ammonium chloride, cetylpyridinium chloride, and methacryloxyethyl cetyl ammonium chloride, QAS chlorides, QAS bromides, QAS monomethacrylates, QAS dimethacrylates, and pre-fabricated QAS particles. When present, the QAS may make up between about 1% and about 50% of a mass fraction of the dental primer or dental adhesive. In certain aspects, the QAS will make up between about 2% and about 25%, about 3% and about 15%, about 5% and about 20%, or about 7.5% and about 15% of a mass fraction of the dental primer or dental adhesive, or about 1%, 2.5%, 5%, 7.5%, 10%, 12.5, 15%, 17.5%, 20%, 22.5%, 25%, 27.5% or 30% of a mass fraction of the dental primer or dental adhesive.

In embodiments where the dental primer or dental adhesive comprises a remineralizing agent, such agents include, but are not limited to, nanoparticles of amorphous calcium phosphate (NACP). NACP comprises nanometer-sized amorphous calcium phosphate ($Ca_3[PO_4]_2$) particles that can be used to produce a dental primer or dental adhesive with high Ca and $PO_4$ release, improved mechanical properties, and improved antibacterial properties. The dental primers and dental adhesives that include NACP exhibit greatly increased ion release at acidic, cariogenic pH, when these ions are most needed to inhibit caries.

The NACP included in the dental primers and dental adhesives of the present invention, when present, will vary in size, but at least about 50, 55, 60, 65, 70, 75, 80, 85, 86, 87, 88, 89, 90, 91, 92, 93, 94, 95, 96, 97, 98 or 99% of the particles, or all of the particles (100%), have an average diameter of between about 10 nm and about 500 nm. In certain aspects, the average diameter will be between about 25 nm and about 400 nm, about 50 nm and about 300 nm, about 75 nm and about 200 nm, or about 100 nm and about 150 nm. In a particular aspect, the NACP particles have an average diameter of between about 50 nm and about 200 nm.

The amount of NACP included in the dental primers and dental adhesives may vary, but the NACP will generally comprise about 1% to about 90% of the mass of the dental primer or dental adhesive. In certain aspects, the NACP will comprise about 1% to about 40%, about 5% to about 70%, about 5% to about 60%, about 5% to about 50%, about 5% to about 45%, about 5% to about 40%, about 5% to about 30%, about 10% to about 90%, about 10% to about 80%, about 10% to about 70%, about 10% to about 60%, about 10% to about 50%, about 10% to about 40%, about 15% to about 70%, about 15% to about 60%, about 15% to about 50%, about 15% to about 40%, about 20% to about 90%, about 85% to about 70%, about 20% to about 80%, about 20% to about 70%, about 20% to about 60%, about 20% to about 50%, about 20% to about 40%, about 25% to about 70%, about 25% to about 60%, about 25% to about 50%, about 25% to about 40%, about 30% to about 90%, about 30% to about 85%, about 30% to about 80%, about 30% to about 75%, about 30% to about 70%, about 30% to about 60%, about 15% to about 45%, about 15% to about 35%, or about 15% to about 25% of the mass of the dental primer or dental adhesive. In certain other aspects, the NACP is a mass fraction of about 25%, about 25.5%, about 26%, about 26.5%, about 27%, about 27.5%, about 28%, about 28.5%, about 29%, about 29.5% or about 30% of the dental primer or dental adhesive. In particular aspects, the NACP will comprise about 5, 6, 7, 8, 9, 10, 11, 12, 13, 14, 15, 16, 17, 18, 19, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90% of the mass of the dental primer or dental adhesive. In certain aspects, the NACP will range from about 10% to about 40% of the mass of the dental primer or dental adhesive.

The dental primers and dental adhesives of the invention may include one, two, three, four or more antibacterial agents of different identity. As non-limiting examples, the dental primers may include:

(a) one type of antibacterial monomer;
(b) one type of silver-containing nanoparticle;
(c) one type of quaternary ammonium salt;
(d) one type of antibacterial monomer and one type of silver-containing nanoparticle;
(e) one type of antibacterial monomer and one type of quaternary ammonium salt;
(f) one type of silver-containing nanoparticle and one type of quaternary ammonium salt;
(g) one type of antibacterial monomer, one type of silver-containing nanoparticle, and one type of quaternary ammonium salt;
(h) two types of antibacterial monomer and one type of silver-containing nanoparticle;
(i) two types of antibacterial monomer and one type of quaternary ammonium salt; or
(j) two types of antibacterial monomer, one type of silver-containing nanoparticle, and one type of quaternary ammonium salt.

As non-limiting examples, the dental adhesives may include:

(a) one type of antibacterial monomer;
(b) one type of silver-containing nanoparticle;
(c) one type of quaternary ammonium salt;
(d) one type of antibacterial monomer and one type of silver-containing nanoparticle;
(e) one type of antibacterial monomer and one type of quaternary ammonium salt;
(f) one type of silver-containing nanoparticle and one type of quaternary ammonium salt;
(g) one type of antibacterial monomer, one type of silver-containing nanoparticle, and one type of quaternary ammonium salt;
(h) two types of antibacterial monomer and one type of silver-containing nanoparticle;
(i) two types of antibacterial monomer and one type of quaternary ammonium salt;
(j) two types of antibacterial monomer, one type of silver-containing nanoparticle, and one type of quaternary ammonium salt;
(k) one type of antibacterial monomer and NACP;
(l) one type of silver-containing nanoparticle and NACP;
(m) one type of quaternary ammonium salt and NACP;

(n) one type of antibacterial monomer, one type of silver-containing nanoparticle and NACP;
(o) one type of antibacterial monomer, one type of quaternary ammonium salt and NACP;
(p) one type of silver-containing nanoparticle, one type of quaternary ammonium salt and NACP;
(q) one type of antibacterial monomer, one type of silver-containing nanoparticle, one type of quaternary ammonium salt and NACP;
(r) two types of antibacterial monomer, one type of silver-containing nanoparticle and NACP;
(s) two types of antibacterial monomer, one type of quaternary ammonium salt and NACP; or
(t) two types of antibacterial monomer, one type of silver-containing nanoparticle, one type of quaternary ammonium salt and NACP.

Non-limiting examples of the dental primers of the present invention include:
(a) a dental primer comprising about 95% primer and about 5% QADM by mass;
(b) a dental primer comprising about 90% primer and about 10% QADM by mass;
(c) a dental primer comprising about 99.95% primer and about 0.05% NAg by mass;
(d) a dental primer comprising about 99.9% primer and about 0.1% NAg by mass;
(e) a dental primer comprising about 89.95% primer, about 10% QADM and about 0.05% NAg by mass;
(f) a dental primer comprising about 95% primer and about 5% DMAHM by mass;
(g) a dental primer comprising about 95% primer and about 5% DMADDM by mass;
(h) a dental primer comprising about 94.9% primer, about 5% DMAHM by mass and about 0.1% NAg by mass; or
(i) a dental primer comprising about 94.9% primer, about 5% DMADDM by mass and about 0.1% NAg by mass. In each of these examples, the primer in the dental primer may be any of the primers disclosed here, including (a) SBMP primer comprising 35-45% 2-hydroxyethylmethacrylate (HEMA), 10-20% copolymer of acrylic and itaconic acids, and 40-50% water; and (b) PMGDM/HEMA at 3.3/1 ratio+1% BAPO+50% acetone.

Non-limiting examples of the dental adhesives of the present invention include:
(a) a dental adhesive comprising about 90% adhesive and about 10% QADM by mass;
(b) a dental adhesive comprising about 99.95% adhesive and about 0.05% NAg by mass;
(c) a dental adhesive comprising about 99.9% adhesive and about 0.1% NAg by mass;
(d) a dental adhesive comprising about 89.95% adhesive, about 10% QADM and about 0.05% NAg by mass;
(e) a dental adhesive comprising about 89.9% adhesive, about 10% QADM and about 0.1% NAg by mass;
(f) a dental adhesive comprising about 89.9% adhesive, about 10% NACP and about 0.1% NAg by mass;
(g) a dental adhesive comprising about 79.9% adhesive, about 20% NACP and about 0.1% NAg by mass;
(h) a dental adhesive comprising about 69.9% adhesive, about 30% NACP and about 0.1% NAg by mass;
(i) a dental adhesive comprising about 59.9% adhesive, about 40% NACP and about 0.1% NAg by mass;
(j) a dental adhesive comprising about 79.9% adhesive, about 10% NACP, about 10% QADM and about 0.1% NAg by mass;
(k) a dental adhesive comprising about 59.9% adhesive, about 20% NACP, about 20% QADM and about 0.1% NAg by mass;
(l) a dental adhesive comprising about 59.9% adhesive, about 30% NACP, about 10% QADM and about 0.1% NAg by mass;
(m) a dental adhesive comprising about 49.9% adhesive, about 40% NACP, about 10% QADM and about 0.1% NAg by mass;
(n) a dental adhesive comprising about 95% adhesive and about 5% DMAHM by mass;
(o) a dental adhesive comprising about 95% adhesive and about 5% DMADDM by mass;
(p) a dental adhesive comprising about 94.9% adhesive, about 5% DMAHM by mass and about 0.1% NAg by mass; or
(q) a dental adhesive comprising about 94.9% adhesive, about 5% DMADDM by mass and about 0.1% NAg by mass. In each of these example, the adhesive in the dental adhesive may be any of the adhesives disclosed here, including (a) SBMP adhesive comprising 60-70% BisGMA and 30-40% HEMA; and (b) BisGMA/TEGMA at 7/3 ratio+1% BAPO.

The dental bonding systems of the invention include a two-component dental bonding system comprising a dental primer and a dental adhesive, a three-step bonding system, a two-step bonding system, and a one-step self-adhesive bonding system.

The two-component dental bonding systems of the invention comprise (i) a dental primer and (ii) a dental adhesive, wherein one or both the dental primer and the dental adhesive has antibacterial properties. In a related embodiment, the two-component dental bonding systems comprise (i) a dental primer and (ii) a dental adhesive, wherein one or both the dental primer and the dental adhesive has antibacterial properties, and wherein one or both the dental primer and the dental adhesive has remineralizing properties. The two-component dental bonding system may be used, in one example, as follows. Before using the bonding system, the tooth is prepared by removing decayed material, cleaning the enamel/dentin surface and applying an etchant to the enamel/dentin surface. A bonding system is then utilized, which can comprise, as an example, application of a dental primer, followed by a dental adhesive. After curing the adhesive, a composite is packed into the void of the tooth. In some aspects, the dental primer or the dental adhesive in the two-component dental bonding systems may exclude antibacterial agents.

Three-step dental bonding systems of the invention include those that comprise (i) an etchant, (ii) a dental primer, and (iii) a dental adhesive, wherein one or both the dental primer and the dental adhesive has antibacterial properties. In certain aspects, one or both of the dental primer and the dental adhesive also has remineralizing properties.

Two-step dental bonding systems of the invention include those that comprise (i) an etchant, and (ii) a mixture comprising a dental primer and a dental adhesive, wherein one or both the dental primer and the dental adhesive has antibacterial properties. In certain aspects, one or both of the dental primer and the dental adhesive also has remineralizing properties.

One-step self-adhesive bonding systems of the invention include those that comprise a mixture that comprises an etchant, a dental primer, and a dental adhesive, wherein one or both the dental primer and the dental adhesive has antibacterial properties. In certain aspects, one or both of the dental primer and the dental adhesive also has remineralizing properties.

Suitable etchants for use in the dental bonding systems of the present invention include Scotchbond Multi-Purpose (SBMP) (3M, St. Paul, Minn.) etchant which contains 37% phosphoric acid.

Each of the dental bonding systems, dental primers and dental adhesives of the present invention are suitable for use in the teeth of mammals, including primates such as human or non-human primates, and those of dogs, cats, horses, cattle, pigs, goats and sheep, for example.

The dental bonding systems, dental primers and dental adhesives described herein can be used in a method of inhibiting growth of aciduric bacteria on a surface of a tooth of a subject, comprising restoring a surface of the tooth from which a decayed portion has been removed by applying a dental composite using a dental bonding system, dental primer and/or dental adhesive described herein to the surface of the tooth, thereby inhibiting growth of aciduric bacteria on the tooth of the subject.

The dental bonding systems, dental primers and dental adhesives described herein can also be used in a method of inhibiting further decay of a decaying tooth in a subject, comprising restoring a surface of the tooth from which a decayed portion has been removed by applying a dental composite using a dental bonding system, dental primer and/or dental adhesive described herein to the surface of the tooth, thereby inhibiting further decay of the decaying tooth in the subject.

EXAMPLES

Example 1

Antibacterial Dental Primers with Quaternary Ammonium and Silver Nanoparticles

The objective of this study was to develop antibacterial dental primers by incorporation of QADM and NAg, and to investigate biofilm viability and acid production using a dental plaque microcosm model. It was found that: (1) Incorporating QADM or NAg into a dental primer did not compromise dentin shear bond strength; (2) QADM-NAg-containing dental primer, in uncured or cured state, was strongly antibacterial; (3) Combining QADM and NAg together in a dental primer yielded a stronger antibacterial capability than each agent alone.

Materials and Methods

SCOTCHBOND MULTI-PURPOSE™ adhesive (referred as "SBMP") (3M, St. Paul, Minn.) was used as the parent adhesive to test the effect of QADM-NAg incorporation. SBMP etchant contained 37% phosphoric acid. SBMP primer contained 35-45% 2-hydroxyethylmethacrylate (HEMA), 10-20% copolymer of acrylic/itaconic acids, and 40-50% water. SBMP adhesive contained 60-70% Bis-GMA and 30-40% HEMA. QADM-NAg were incorporated into SBMP primer. SBMP etchant and adhesive were not modified.

The QADM, bis(2-methacryloyloxyethyl)dimethylammonium bromide, was recently synthesized (Antonucci et al., 2011; Cheng et al., 2012a). Briefly, 10 mmol of 2-(N, N-dimethylamino)ethyl methacrylate (DMAEMA, Sigma-Aldrich, St. Louis, Mo.) and 10 mmol of 2-bromoethyl methacrylate (BEMA, Monomer-Polymer Labs, Trevose, Pa.) were combined with 3 g of ethanol, and stirred at 60° C. for 24 h. The solvent was then evaporated, yielding QADM. QADM was mixed with SBMP primer at QADM/(primer+QADM)=10% by mass, following a previous study (Cheng et al., 2012a).

Silver 2-ethylhexanoate (Strem, New Buryport, Mass.) of 0.08 g was dissolved into 1 g of 2-(tert-butylamino)ethyl methacrylate (TBAEMA, Sigma). TBAEMA could facilitate Ag salt dissolution in the resin (Cheng Y J et al., 2011). This Ag solution was mixed with SBMP primer at 0.05% by mass of silver 2-ethylhexanoate (Cheng et al., 2012a).

Hence, the following four primers were tested: (1) SBMP primer (control); (2) control primer+10% QADM (termed "10QADM"); (3) control primer+0.05% NAg (termed "0.05NAg"); (4) control primer+10% QADM+0.05% NAg (termed "10QADM+0.05NAg").

A transmission electron microscope (TEM, Tecnai-T12, FEI Company, Hillsboro, Oreg.) was used to examine the silver nanoparticles in the resin. Following a previous study (Cheng Y J et al., 2011), a thin sheet of mica was partially-split and the Ag-containing resin was placed in the gap. The resin in the mica was pressed to form a film and then photo-cured. The resin film was used for TEM examination.

Extracted caries-free human third molars were sawed to remove the crowns (Isomet, Buehler, Lake Bluff, Ill.). The mid-coronal dentin surface was ground perpendicular to the longitudinal axis of the tooth on 320-grit SiC paper until occlusal enamel was completely removed. The dentin surface was etched with 37% phosphoric acid for 15 s and rinsed with water (Antonucci et al., 2009). A primer was applied, and the solvent was removed with an air stream. The adhesive was applied and light-cured for 10 s (Optilux-VCL401, Demetron, Danbury, Conn.).

A stainless-steel iris having a central opening (diameter=4 mm, thickness=1.5 mm) was held against the adhesive-treated dentin (Antonucci et al., 2009). The central opening was filled with a composite (TPH, Caulk/Dentsply, Milford, Del.) and light-cured for 60 s. Specimens were stored in water at 37° C. for 24 h. Dentin shear bond strength, $S_D$, was measured following a previous method (Antonucci et al., 2009). A chisel was aligned parallel to the composite-dentin interface, and loaded via a computer-controlled Universal Testing Machine (MTS, Eden Prairie, Minn.) at 0.5 mm/min until the composite-dentin bond failed. $S_D=4P/(\pi d^2)$, where P is load at failure, and d is composite diameter.

Saliva was collected from a healthy adult donor having natural dentition without active caries or periopathology, and without using antibiotics within the last 3 months. The donor did not brush teeth for 24 h and abstained from food/drink intake for 2 h prior to donating saliva. Stimulated saliva was collected during parafilm chewing and kept on ice. The saliva was diluted in sterile glycerol to a concentration of 30% (Cheng L et al., 2011).

The un-cured primers were tested in agar disk diffusion. The saliva-glycerol was added to a growth medium containing mucin (concentration=2.5 g/L), bacteriological peptone (concentration=2.0 g/L), tryptone (concentration=2.0 g/L), yeast extract (concentration=1.0 g/L), NaCl (concentration=0.35 g/L), KCl (concentration=0.2 g/L), $CaCl_2$ (concentration=0.2 g/L), and cysteine hydrochloride (concentration=0.1 g/L) (pH=7.0) (McBain, 2009). The inoculum was incubated (37° C., 5% $CO_2$) for 24 h, and then used for the agar disk diffusion test. It employed three types of media. First, tryptic soy blood agar plates were used to determine total microorganisms (Cheng L et al., 2011). Second, *mitis salivarius* agar (MSA) plates, containing 15% sucrose, were used to determine total streptococci. Third, MSA plates plus 0.2 units of bacitracin/mL was used to determine *mutans* streptococci.

Bacteria suspension of 0.4 mL was poured onto each agar plate (diameter=90 mm, thickness=4 mm). Then, 30 μL of each primer was impregnated into a sterile paper disk (diameter=9 mm, thickness=1.5 mm) (Imazato et al., 2006). The primer-impregnated paper disk (referred to as "disk") was placed on a plate with bacteria, and incubated for 48 h. Bacteria inhibition zone size=(Outer diameter of inhibition zone−disk diameter)/2.

Cured specimens were fabricated as schematically-shown in FIG. 24A, following a previous study (Imazato et al., 1998). A polyethylene mold (inner diameter=9 mm, thickness=2 mm) was situated on a glass slide. Each primer was brushed into the mold on the glass slide. After drying with a stream of air, SBMP adhesive was applied and cured for 20 s with Optilux. Then, a composite (TPH) was placed on the adhesive to fill the mold and light-cured for 1 min. Specimens were agitated in water for 1 h to remove uncured monomers (Imazato et al., 1998).

Each specimen was placed into a well of 24-well plates with the primer facing up. 1.5 mL of inoculum was added to each well. The assemblies were incubated for 8 h. The specimens were then transferred to new 24-well plates with fresh medium. After 16 h, the specimens were transferred to new 24-well plates with fresh medium and incubated for 24 h (Cheng L et al., 2011). Then, the biofilms on specimens were washed with phosphate-buffered saline (PBS), live/dead stained (Molecular Probes, Eugene, Oreg.), and examined using an epifluorescence microscope (TE2000-S, Nikon, Melville, N.Y.).

For colony-forming unit (CFU) counts, specimens with 2-d biofilm were rinsed with cysteine peptone water (CPW) to remove loose bacteria. The specimens were transferred to 24-well plates containing buffered-peptone water (BPW) plus 0.2% sucrose, and incubated for 3 h to allow biofilms to produce acid. Lactate concentrations were determined using an enzymatic method (Cheng L et al., 2011). A microplate reader (SpectraMax, Molecular Devices, Sunnyvale, Calif.) was used to measure the 340-nm absorbance. Standard curves were prepared using a lactic acid standard (Supelco, Bellefonte, Pa.).

Specimens were transferred into tubes with 2-mL CPW, and the biofilms were harvested by sonication/vortexing (Fisher, Pittsburgh, Pa.). Three types of agar plates were used: Tryptic soy blood plates to determine total microorganisms; MSA plus 15% sucrose to determine total streptococci; and MSA plus 0.2 units of bacitracin/mL to determine *mutans* streptococci.

One-way and two-way analyses-of-variance (ANOVA) were performed to detect the significant effects of variables. Tukey's multiple comparison was used to compare the data at p=0.05.

Results

Figure 1:
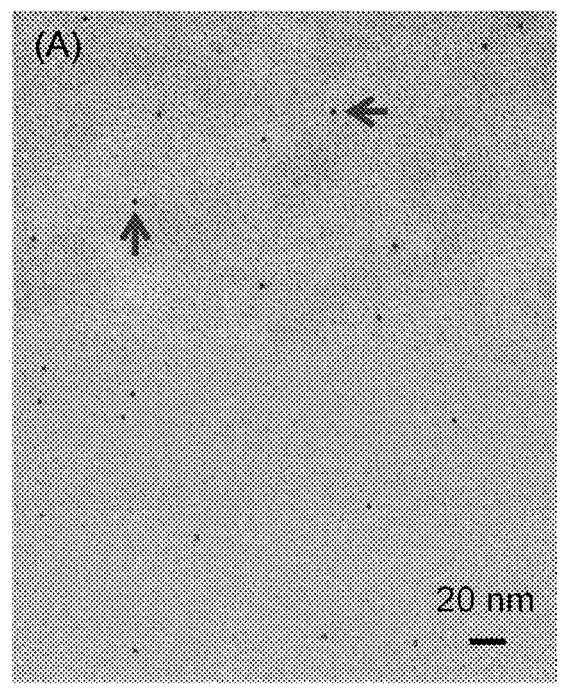
FIG. 1. TEM image of nanoparticles of silver (NAg), and dentin shear bond strength. In (A), the NAg particle sizes ranged from approximately 2 to 5 nm, with (mean±sd, n=100) of (2.7±0.6) nm. The NAg particles appeared to be well dispersed in the resin, without noticeable agglomeration. In (B), the dentin shear bond strength was between 30 to 35 MPa. Ten teeth were tested for each group (n=10). The horizontal line indicates values not significantly different from each other (p>0.1).
Figure 1:
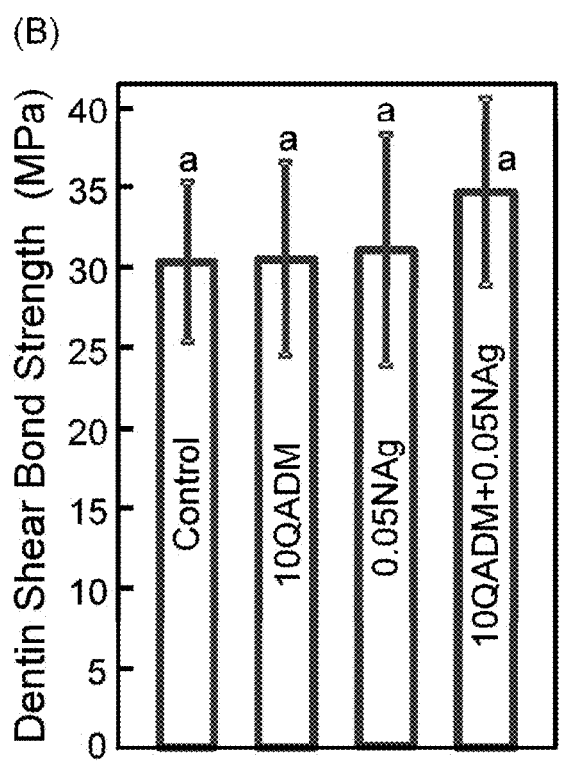

TEM examination showed NAg particle sizes ranging 2-5 nm (FIG. 1A). Measurement of 100 particles (mean±sd) yielded (2.7±0.6) nm. The NAg were well-dispersed in the resin, without noticeable agglomeration. Dentin shear bond strengths (FIG. 1B) were about 30-35 MPa. Adding QADM and NAg into primer did not compromise the bond strength (p>0.1).

Figure 2:
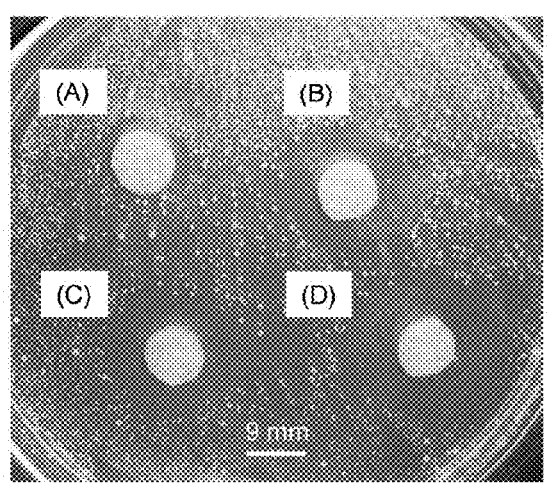
FIG. 2. Antibacterial activity of un-cured primers in agar disk diffusion test. (A-D) Control primer, 10QADM, 0.05NAg, and 10QADM+0.05NAg, respectively. Note a small inhibition zone for control, and much wider inhibition zones for primers with QADM and NAg. This example is for *mutans* streptococci. Total microorganisms and total streptococci had similar results. (E-G) Inhibition zone data for total microorganisms, total streptococci, and *mutans* streptococci, respectively. Each value is mean±sd (n=6). Bars with dissimilar letters indicate values that are significantly different (p<0.05).
Figure 2:
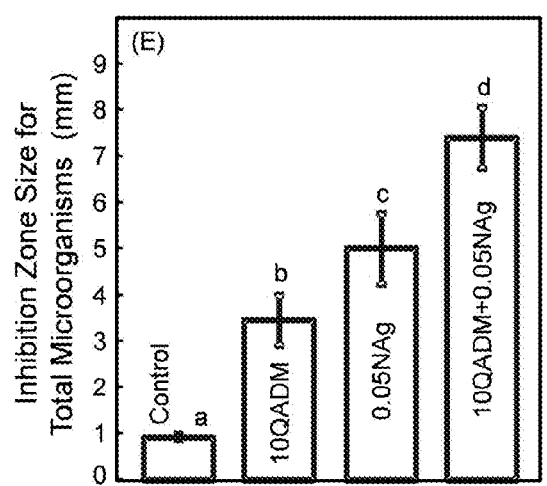
Figure 2:
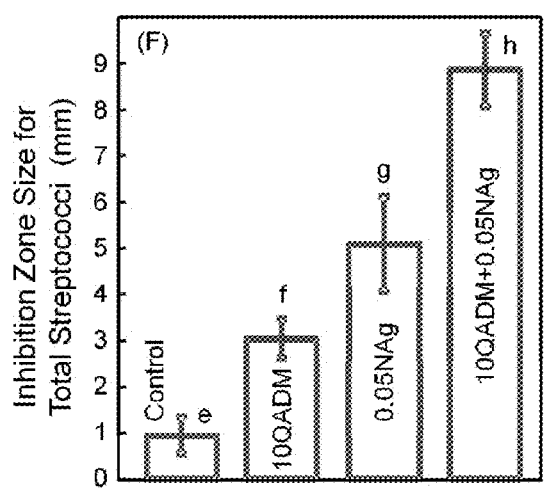
Figure 2:
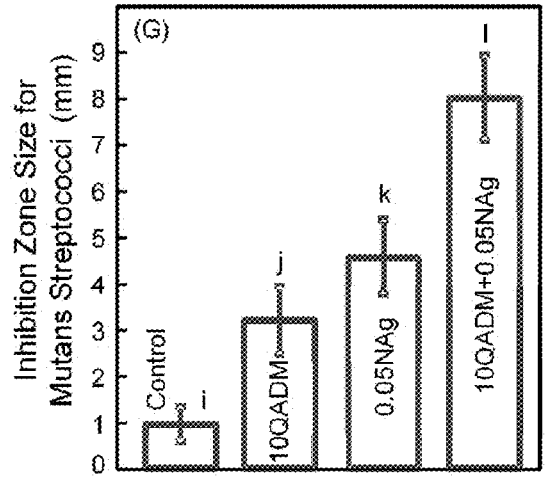

Un-cured QADM-NAg primers had a strong antibacterial activity (FIG. 2). Control primer had a minimal inhibition zone (A). Primers 10QADM (B), 0.05NAg (C), and 10QADM+0.05NAg (D) had much larger inhibition zones. Inhibition zone sizes are plotted in (E-G) for total microorganisms, total streptococci, and *mutans* streptococci, respectively. Inhibition zone sizes for 10QADM+0.05NAg were 8-9 fold those of control (p<0.05).

Figure 3:
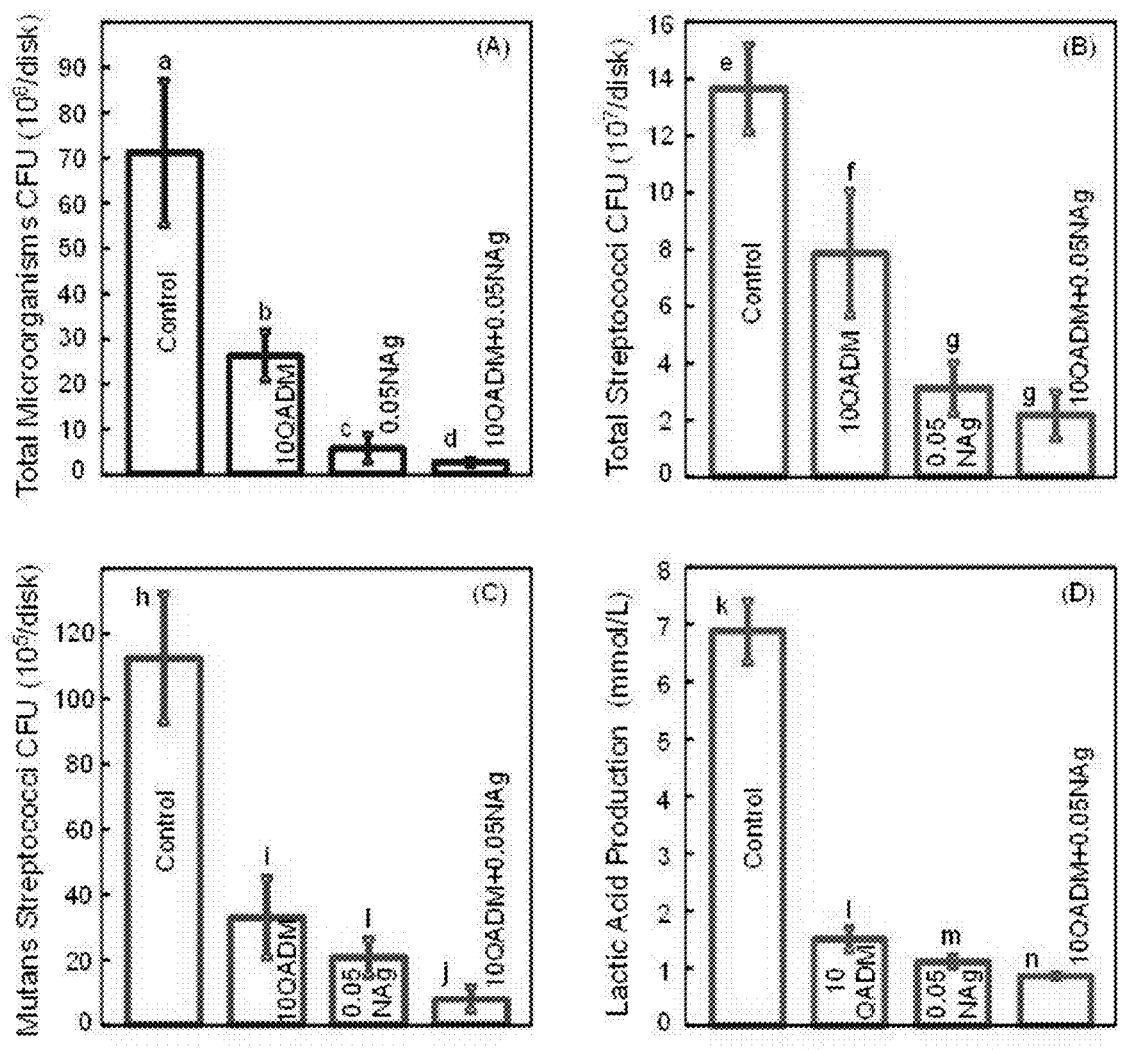
FIG. 3. Biofilm CFU counts and lactic acid production on specimens with cured primers. (A) CFU of total microorganisms, (B) CFU of total streptococci, (C) CFU of *mutans* streptococci, and (D) lactic acid production. Each value is mean±sd (n=6). In each plot, values with dissimilar letters are significantly different (p<0.05). Adding QADM or NAg into the primer imparted a potent antibacterial effect. The strongest antibacterial effect was achieved with QADM and NAg together in the same primer.

Biofilms were grown on cured primers (FIG. 24A). Control primer had full coverage of primarily live bacteria, while 10QADM, 0.05NAg, and 10QADM+0.05NAg exhibited strong antibacterial activity. The 10QADM, 0.05NAg, and 10QADM+0.05NAg primers greatly reduced the CFU counts (FIG. 3A-C). CFU on 10QADM+0.05NAg was approximately an order of magnitude less than those on control primer. Lactic acid from biofilms (FIG. 3D) was reduced on 10QADM, 0.05NAg, and 10QADM+0.05NAg, compared to control (p<0.05). These results demonstrate that adding QADM or NAg into primer imparted a potent antibacterial effect, and the strongest effect was achieved by combining QADM and NAg in the primer.

Example 2

Effect of Quaternary Ammonium and Silver Nanoparticle-Containing Adhesives on Dentin Bond Strength and Dental Plaque Microcosm Biofilms The objective of this study were to develop an antibacterial, two-component, dental bonding system by incorporation of quaternary ammonium dimethacrylate (QADM) and nanoparticles of silver (NAg) into dental primers and dental adhesives, and to investigate the effect of QADM-NAg-containing adhesive and primer on dentin bond strength and plaque microcosm biofilm response for the first time. Adding QADM and NAg into adhesive and primer did not compromise the dentin shear bond strength which ranged from 30 to 35 MPa (p>0.1). Adding QADM or NAg markedly reduced the biofilm viability, compared to adhesive control. QADM and NAg together in the adhesive had a much stronger antibacterial effect than using each agent alone (p<0.05). Adding QADM and NAg in both adhesive and primer had the strongest antibacterial activity, reducing metabolic activity, CFU, and lactic acid by an order of magnitude, compared to control.

Materials and Methods
QADM Incorporation

Scotchbond Multi-Purpose bonding system (3M, St. Paul, Minn.), referred as "SBMP", was used as the parent bonding system to test the effect of incorporation of QADM and NAg. The purpose was to investigate a model system, and then the method of QADM and NAg incorporation could be applied to other adhesive systems. According to the manufacturer, SBMP etchant contains 37% phosphoric acid. SBMP primer single bottle contains 35-45% 2-Hydroxyethylmethacrylate (HEMA), 10-20% copolymer of acrylic and itaconic acids, and 40-50% water. SBMP adhesive contains 60-70% BisGMA and 30-40% HEMA.

Bis(2-methacryloyloxyethyl)dimethylammonium bromide was a quaternary ammonium dimethacrylate (QADM), and was recently synthesized and incorporated into dental composites (Antonucci et al. 2011; Cheng L. et al. 2011). The synthesis of QADM was performed using a modified Menschutkin reaction, where a tertiary amine group was reacted with an organo-halide. A benefit of this reaction is that the reaction products are generated at virtually quantitative amounts and require minimal purification (Antonucci et al. 2011). Briefly, 10 mmol of 2-(N,N-dimethylamino) ethyl methacrylate (DMAEMA, Sigma, St. Louis, Mo.) and 10 mmol of 2-bromoethyl methacrylate (BEMA, Monomer-Polymer and Dajec Labs, Trevose, Pa.) were combined with 3 g of ethanol in a 20 mL scintillation vial. The vial was stirred at 60° C. for 24 h. The solvent was then removed, yielding QADM as a clear, colorless, and viscous liquid. The QADM was mixed with the SBMP adhesive or primer at a QADM mass fraction of 10%. QADM mass fractions of 20% or higher were not used due to a decrease in dentin bond strength in preliminary study.

NAg Incorporation

Silver 2-ethylhexanoate powder (Strem, New Buryport, Mass.) was dissolved in 2-(tert-butylamino)ethyl methacrylate (TBAEMA, Sigma) at 0.08 g of silver salt per 1 g of TBAEMA, following previous studies (Cheng L. et al. 2011; Cheng Y J. et al. 2011). TBAEMA was used because it improves the solubility by forming Ag—N coordination bonds with Ag ions, thereby facilitating the Ag salt to dissolve in the resin solution. TBAEMA was selected since it contains reactive methacrylate groups and therefore can be chemically incorporated into a dental resin upon photopolymerization (Cheng L. et al. 2011; Cheng Y J. et al. 2011). This method produced NAg with a mean particle size of 2.7 nm that were well dispersed in the resin matrix (Cheng L. et al. 2011). The Ag solution was mixed with SBMP adhesive at silver 2-ethylhexanoate mass fractions of 0.05% and 0.1%. Ag mass fractions of 0.15% or higher were not used due to a decrease in dentin bond strength.

Dentin Shear Bond Testing and SEM Examination

As listed in Table 1, six groups were used for dentin shear bond strength testing. The purpose of groups 1-3 was to investigate the effects of QADM or NAg individually. The purpose of 3 and 4 was to examine the effect of NAg mass fraction. The purpose of comparing 2, 3 and 5 was to examine the effect of combining QADM and NAg together in the same adhesive. The purpose of comparing 5 with 6 was to investigate the effects of adding QADM and NAg into both the adhesive and the primer on dentin bond strength and biofilm response.

TABLE 1

Compositions of adhesive resin and dentin primer*

| Group | Adhesive resin | Dentin primer | Group name |
|---|---|---|---|
| 1 | Control | Control | Control |
| 2 | Control + 10% QADM | Control | A + 10QADM |
| 3 | Control + 0.05% NAg | Control | A + 0.05NAg |
| 4 | Control + 0.1% NAg | Control | A + 0.1NAg |
| 5 | Control + 10% QADM + 0.05% NAg | Control | A + 10QADM + 0.05NAg |
| 6 | Control + 10% QADM + 0.05% NAg | Control + 10% QADM + 0.05% NAg | A&P + 10QADM + 0.05NAg |

*The control adhesive was the SBMP adhesive without modification. The control primer was the SBMP primer without modification. QADM = quaternary ammonium dimethacrylate. NAg = nanoparticles of silver. In the "Group name" column, A = adhesive resin. P = primer.

Extracted caries-free human third molars were cleaned and stored in 0.01% thymol solution. Flat mid-coronal dentin surfaces were prepared by cutting off the tips of molar crowns with a diamond saw (Isomet, Buehler, Lake Bluff, Ill.). Each tooth was embedded in a poly-carbonate holder (Bosworth, Skokie, Ill.) and ground perpendicular to the longitudinal axis on 320-grit silicon carbide paper until the occlusal enamel was completely removed. As shown schematically in FIG. 4A, the dentin surface was etched with 37% phosphoric acid gel for 15 s and rinsed with distilled water for 15 s, following a previous study (Antonucci et al. 2009). The primer was applied with a brush-tipped applicator and rubbed in for 15 s. The solvent was removed with a stream of air for 5 s. Then the adhesive was applied and light-cured for 10 s (Optilux VCL 401, Demetron Kerr, Danbury, Conn.). A stainless-steel iris, having a central opening with a diameter of 4 mm and a thickness of 1.5 mm, was held against the adhesive-treated dentin surface. The central opening was filled with a composite (TPH, Caulk/Dentsply, Milford, Del.), and light-cured for 60 s. The bonded specimens were stored in distilled water at 37° C. for 24 h.

The dentin shear bond strength, $S_D$, was measured as shown schematically in FIG. 4B (Antonucci et al. 2009). The chisel was connected with a computer-controlled Universal Testing Machine (MTS, Eden Prairie, Minn.) and held parallel to the composite-dentin interface. Load was applied at a rate of 0.5 mm/min until the bond failed. $S_D$ was calculated as: $S_D = 4P/(\pi d^2)$, where P is the load at failure, and d is the diameter of the composite. Ten teeth were tested for each group (n=10).

The bonded tooth was cut through the center in the longitudinal direction via the diamond saw (Isomet) with copious water. Three specimens were prepared for each group. The sectioned surface was polished with increasingly finer SiC paper up to 4000 grit. Following a previous study (Imazato et al. 2003), the polished surface was treated with 50% phosphoric acid for 30 s, then with 10% NaOCl for 2 min. After being thoroughly rinsed with water for 10 min, the specimens were air dried and then sputter-coated with gold. The dentin-adhesive bonded interfaces were then examined via scanning electron microscopy (SEM, Quanta 200, FEI, Hillsboro, Oreg.).

Saliva Collection for Plaque Microcosm Model

The dental plaque microcosm model was approved by the University of Maryland. Human saliva was shown to be ideal for growing plaque microcosm biofilms in vitro, with the advantage of maintaining much of the complexity and heterogeneity of the dental plaque in vivo (McBain A J. 2009). The saliva for biofilm inoculums was collected from a healthy adult donor having natural dentition without active caries or periopathology, and without the use of antibiotics within the last 3 months, following a previous study (Cheng L. et al. 2011). The donor did not brush teeth for 24 h and abstained from food/drink intake for at least 2 h prior to donating saliva. Stimulated saliva was collected during parafilm chewing and kept on ice. The saliva was diluted in sterile glycerol to a concentration of 30%, and stored at −80° C. (Cheng L. et al. 2011).

Specimen Fabrication for Biofilm Experiments

Layered disk specimens for biofilm experiments were fabricated following previous studies (Imazato et al. 1998; Li et al. 2009). A polyethylene disk mold (inner diameter=9 mm, thickness=2 mm) was situated on a glass slide. For groups 1-5, each adhesive was applied into the mold to cover the glass slide. Then, a composite (TPH) was placed onto the adhesive to fill the disk mold and light-cured for 1 min. For group 6, the primer was first applied into the mold to cover the glass slide. After drying with a stream of air, the adhesive was applied and cured for 20 s with Optilux. Then, a composite (TPH) was placed on the adhesive to fill the disk mold and light-cured for 1 min. The disks were immersed in sterile water and agitated for 1 h to remove any uncured monomer, following a previous study (Imazato et al. 1998). The disks were then dried and sterilized with ethylene oxide (Anprolene AN 74i, Andersen, Haw River, N.C.).

Six groups were tested in biofilm experiments. Groups 1-5 had specimens with adhesives 1-5 (Table 1) covering the top surface of the composite disk, without primer, in order to test the antibacterial properties of the adhesives, as shown schematically in FIG. 24B. Group 6 had the QADM-NAg primer covering the adhesive on the composite disk in order to test the antibacterial properties of the primer/adhesive combination, as shown schematically in FIG. 24A.

MTT Assay of Metabolic Activity

The saliva-glycerol stock was added, with 1:50 final dilution, to a growth medium as inoculum. The growth medium contained mucin (type II, porcine, gastric) at a concentration of 2.5 g/L; bacteriological peptone, 2.0 g/L; tryptone, 2.0 g/L; yeast extract, 1.0 g/L; NaCl, 0.35 g/L; KCl, 0.2 g/L; $CaCl_2$, 0.2 g/L; cysteine hydrochloride, 0.1 g/L; haemin, 0.001 g/L; vitamin K1, 0.0002 g/L, at pH 7 (McBain et al. 2005). The inoculum was cultured at 37° C. in an incubator containing 5% $CO_2$ for 24 h. Each disk specimen was placed into a well of 24-well plates, with the antibacterial surface on the top. 1.5 mL of inoculum was added to each well, and incubated in 5% $CO_2$ at 37° C. for 8 h. The disks were then transferred to new 24-well plates with fresh medium and incubated. After 16 h, the disks were transferred to new 24-well plates with fresh medium and incubated for 24 h. This 2-day (d) incubation formed plaque microcosm biofilms as shown previously (Cheng L. et al. 2011).

The MTT (3-[4,5-Dimethylthiazol-2-yl]-2,5-diphenyltetrazolium bromide) assay is a colorimetric assay that measures the enzymatic reduction of MTT, a yellow tetrazole, to formazan (Antonucci et al. 2011; Cheng L. et al. 2011). Each disk with the 2-d biofilm was transferred to a new 24-well plate, then 1 mL of MTT dye (0.5 mg/mL MTT in PBS) was added to each well and incubated at 37° C. in 5% $CO_2$ for 1 h. During this process, metabolically active bacteria reduced the MTT to purple formazan. After 1 h, the disks were transferred to a new 24-well plate, 1 mL of dimethyl sulfoxide (DMSO) was added to solubilize the formazan crystals, and the plate was incubated for 20 min with gentle mixing at room temperature in the dark. After mixing via pipetting, 200 μL of the DMSO solution from each well was transferred to a 96-well plate, and the absorbance at 540 nm (optical density OD540) was measured via a microplate reader (SpectraMax M5, Molecular Devices, Sunnvale, Calif.). A higher absorbance is related to a higher formazan concentration, which indicates a higher metabolic activity in the biofilm on the disk.

Lactic Acid Production and Colony Forming Unit (CFU) Counts

Each disk with the 2-d biofilm was rinsed with cysteine peptone water (CPW) to remove loose bacteria. The disks were transferred to 24-well plates containing buffered peptone water (BPW) plus 0.2% sucrose. The samples were incubated in 5% $CO_2$ at 37° C. for 3 h to allow the biofilms to produce acid. The BPW solutions were then stored for lactate analysis.

Disks with biofilms were transferred into tubes with 2 mL CPW, and the biofilms were harvested by sonication and vortexing via a vortex mixer (Fisher, Pittsburgh, Pa.). Three types of agar plates were used. First, tryptic soy blood agar culture plates were used to determine total microorganisms (Cheng L. et al. 2011). Second, *mitis salivarius* agar (MSA) culture plates, containing 15% sucrose, were used to determine total streptococci (Lima et al. 2009). This is because MSA contains selective agents crystal violet, potassium tellurite and trypan blue, which inhibit most gram-negative bacilli and most gram-positive bacteria except streptococci, thus enabling streptococci to grow (Lima et al. 2009). Third, cariogenic *mutans* streptococci are known to be resistant to bacitracin, and this property is often used to isolate *mutans* streptococci from the highly heterogeneous oral microflora. Hence, MSA agar culture plates plus 0.2 units of bacitracin per mL was used to determine *mutans* streptococci (Hildebrandt et al. 2006).

Lactate concentrations in the BPW solutions were determined using an enzymatic (lactate dehydrogenase) method, following a previous study (Cheng L. et al. 2011). The microplate reader was used to measure the absorbance at 340 nm (optical density $OD_{340}$) for the collected BPW solutions. Standard curves were prepared using a lactic acid standard (Supelco, Bellefonte, Pa.).

One-way analysis of variance (ANOVA) was performed to detect the significant effects of the variables. Tukey's multiple comparison was used to compare the data at a p value of 0.05.

Results

Figure 4:
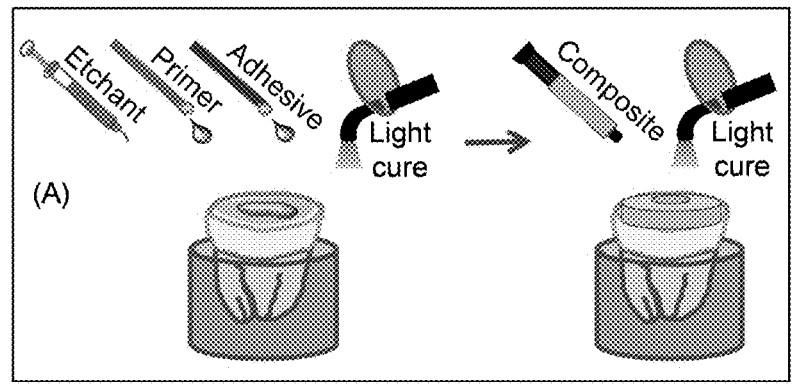
FIG. 4. Human dentin shear bond testing: (A) Schematic of specimen preparation, (B) schematic of shear bond strength testing, (C) shear bond strength data. Ten teeth were used for each group, requiring a total of sixty third-molars. Each value is mean±sd (n=10). Horizontal line indicates that all six groups had similar shear bond strengths (p>0.1).
Figure 4:
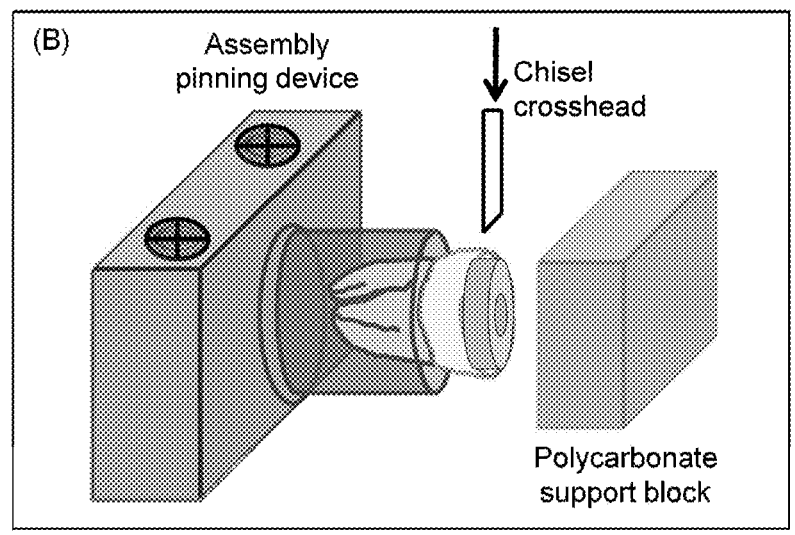
Figure 4:
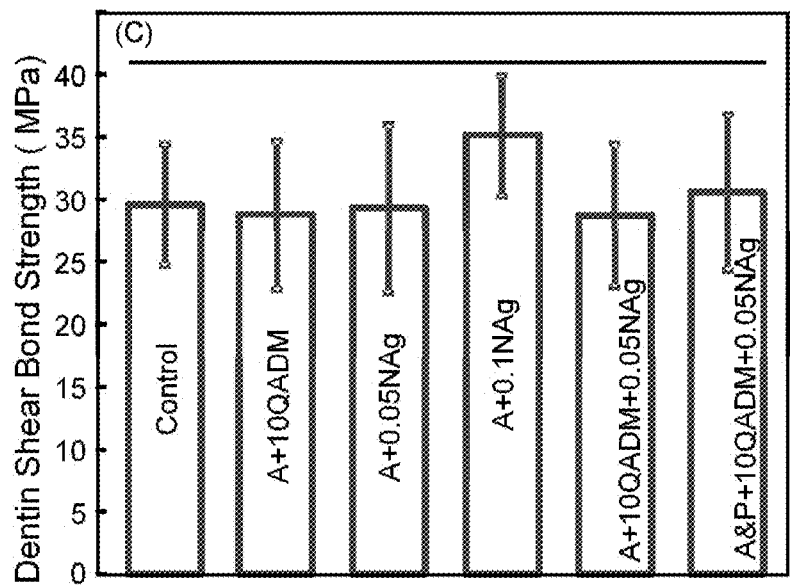

FIG. 4 shows schematics of the dentin shear bond test and the strength results: (A) Schematic of specimen preparation, (B) schematic of shear bond testing, (C) dentin shear bond strength results. In (C), each value is mean±sd (n=10). The six groups had shear bond strengths that were not significantly different (p>0.1), indicating that adding QADM and NAg to adhesive and primer did not compromise the dentin shear bond strength.

Figure 5:
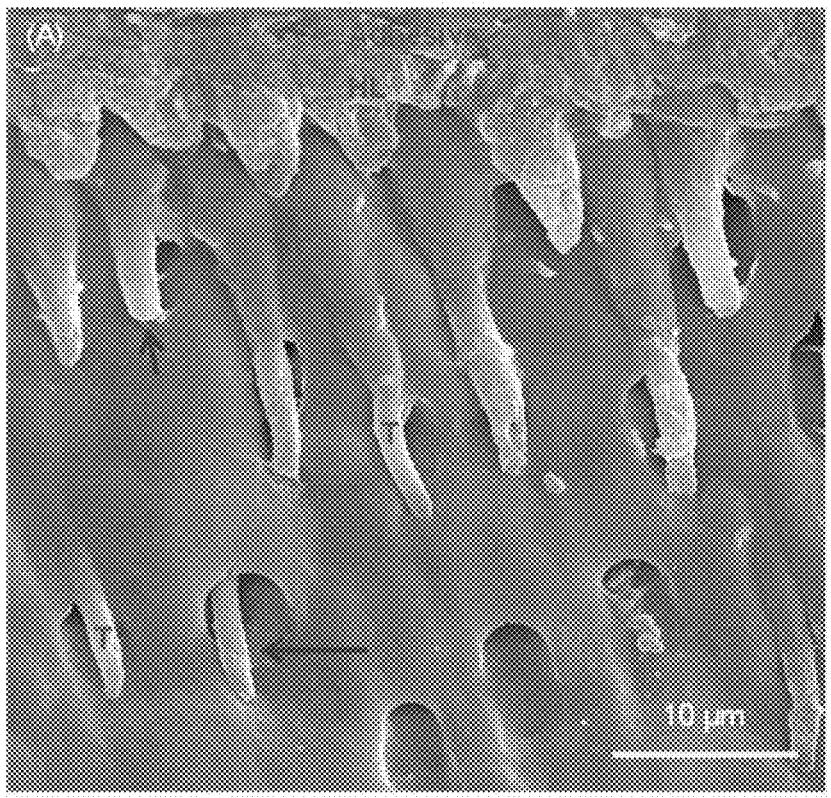
FIG. 5. SEM micrographs of dentin-adhesive interfaces: (A) SBMP control, and (B) A&P+10QADM+0.05NAg. Other groups had similar features and are not included here. "HL" refers to the hybrid layer between the adhesive and the underlying mineralized dentin. The adhesive resin was well-infiltrated into dentinal tubules to form resin tags "T". In (A), the long arrow indicates a long resin tag. The short arrow points to a short tag, which was shortened due to the sectioning surface not being parallel to the tubules. Numerous resin tags were observed in all samples, without noticeable difference between the six groups, indicating that adding QADM and NAg did not affect dentin bonding.
Figure 5:
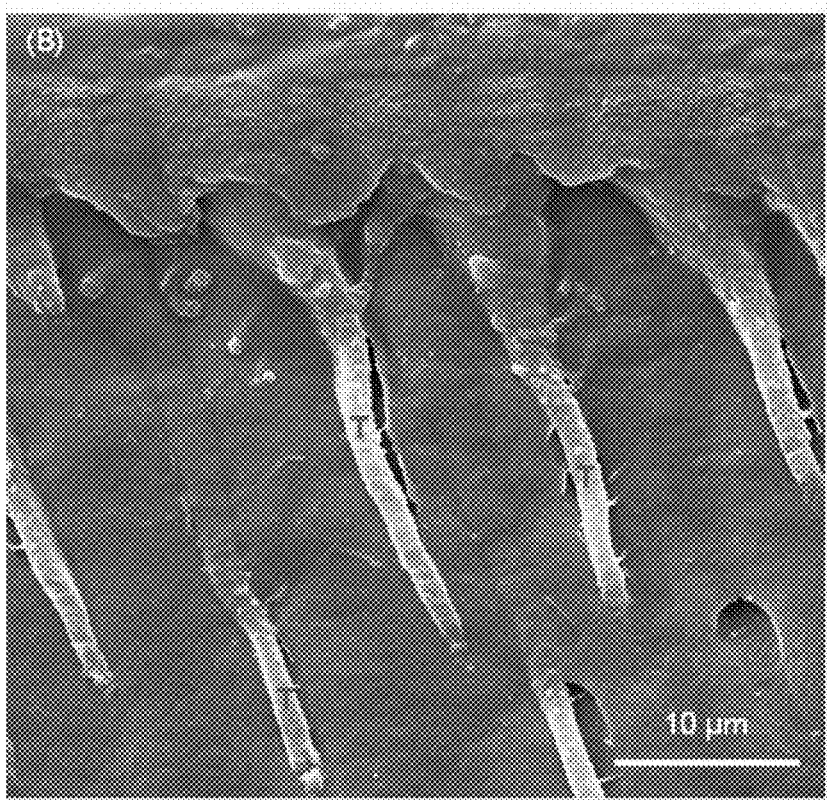

The dentin-adhesive interfaces were examined via SEM, and representative images are shown in FIG. 5: (A) SBMP control, and (B) A&P+10QADM+0.05NAg. "HL" refers to the hybrid layer between the adhesive and the underlying mineralized dentin. "T" indicates the resin tags formed by the adhesive resin filling into the dentinal tubules. Numerous resin tags were found in samples of all six groups. The short arrow in (A) indicates a short resin tag. The long arrow indicates an example of a long resin tag. Some tags were shorter because, during sample preparation, the sectioning surface was not exactly parallel to the long axis of dentinal tubules. Some tubules were intersected by the cutting and thus shortened. A mixture of long and short tags was observed in all samples. There was no noticeable difference between the six groups.

Figure 6:
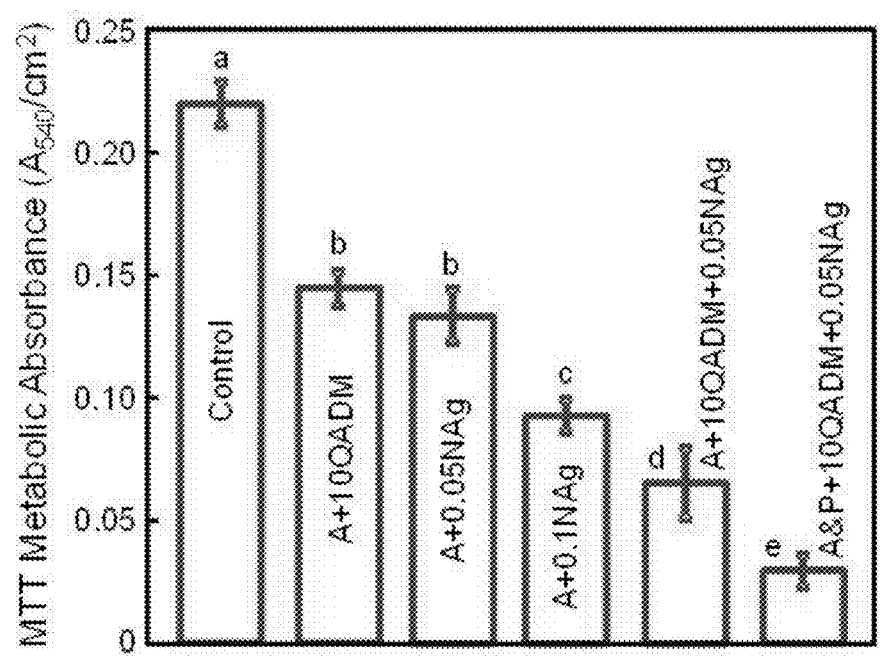
FIG. 6. MTT metabolic activity. Biofilms were grown for 2 d using a microcosm model. Five adhesive groups were tested following schematic of FIG. 24B: Control, A+10QADM, A+0.05NAg, A+0.1NAg, A+10QADM+ 0.05NAg. One group was tested following schematic of FIG. 24A with a primer layer: A&P+10QADM+0.05NAg. Each values is mean±sd (n=6). Values with dissimilar letters are different (p<0.05).

FIG. 6 shows metabolic activity. Groups 1-5 followed schematic of FIG. 24B. Group 6 used the QADM-NAg primer and followed schematic of FIG. 24A. Biofilms on the as-received commercial adhesive had a high metabolic activity. Incorporation of QADM and NAg each markedly reduced the metabolic activity (p<0.05). Adding QADM and NAg together in the adhesive resulted in a much lower metabolic activity than using QADM or NAg alone (p<0.05). Adding QADM and NAg both in the primer and in the adhesive yielded the lowest biofilm metabolic activity (p<0.05). The metabolic activity of biofilms on A&P+10QADM+0.05NAg was nearly an order of magnitude less than that on adhesive control.

Figure 7:
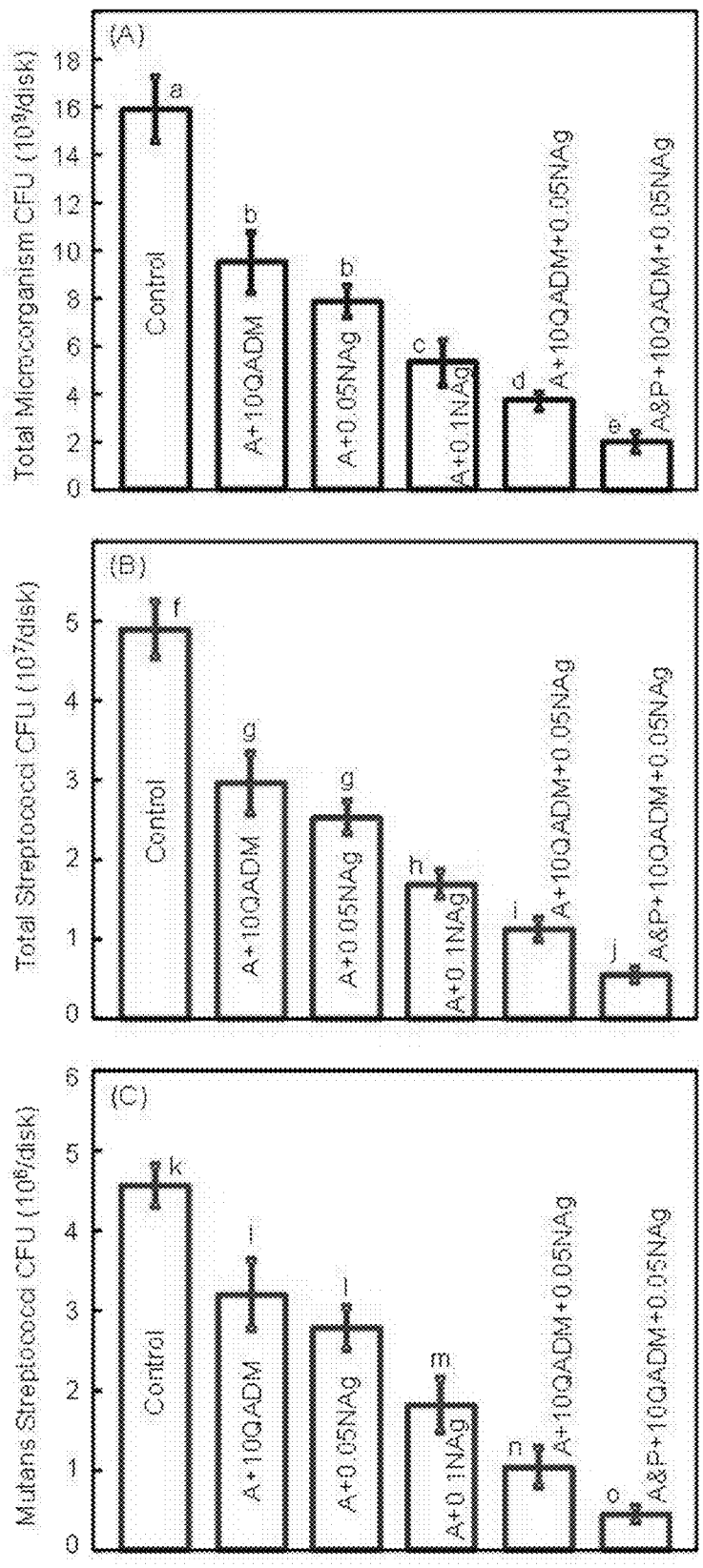
FIG. 7. Microcosm biofilm CFU counts: (A) Total microorganisms, (B) total streptococci, and (C) *mutans* streptococci. Each values is mean±sd (n=6). Values indicated by dissimilar letters are significantly different (p<0.05). The results showed that: (1) QADM or NAg each decreased the CFU compared to commercial adhesive control; (2) higher NAg mass fraction further decreased the CFU; (3) QADM and NAg together yielded a greater reduction in CFU than each alone; (4) QADM and NAg in both primer and adhesive had the strongest antibacterial effect.

FIG. 7 plots CFU counts for: (A) Total microorganisms, (B) total streptococci, and (C) *mutans* streptococci. Adding QADM or NAg each decreased the CFU, compared to the as-received commercial adhesive control (p<0.01). Increasing the NAg mass fraction from 0.05% to 0.1% decreased the CFU (p<0.05). The combination of QADM and NAg in the adhesive had a much stronger antibacterial effect than using QADM or NAg alone (p<0.05). Incorporation of QADM and NAg together, in both the primer and the adhesive, had the greatest reductions in CFU (p<0.05). All three CFU counts for biofilms on A&P+10QADM+0.05NAg were reduced by an order of magnitude, compared to those on the as-received commercial adhesive.

Figure 8:
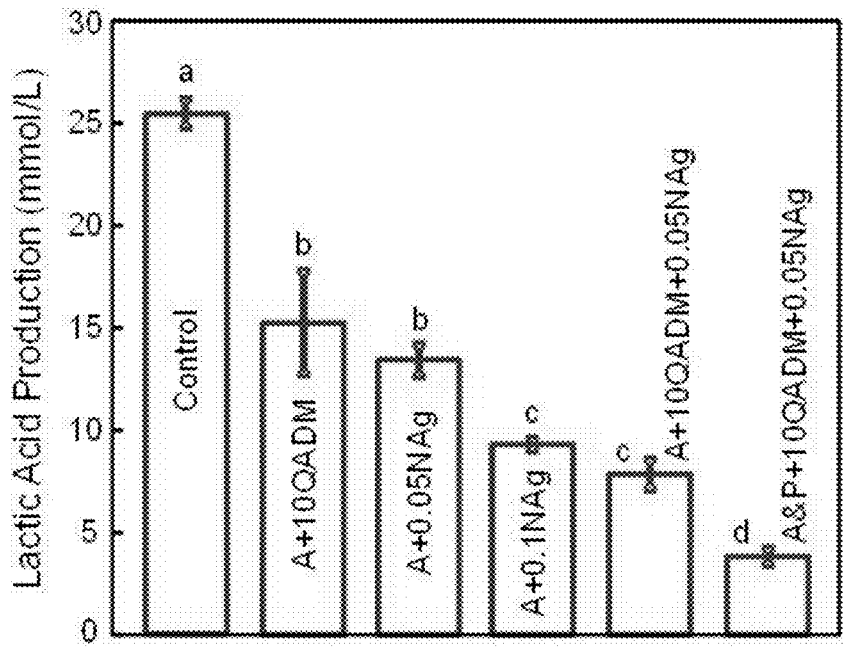
FIG. 8. Lactic acid production by dental plaque microcosm biofilms. Each values is mean±sd (n=6). Values indicated by dissimilar letters are significantly different (p<0.05).

FIG. 8 plots the lactic acid production by biofilms. Biofilms on adhesive control produced the most acid. Adding QADM or NAg each decreased the acid production (p<0.05). Adhesive with 0.1% NAg had less acid than that with 0.05% NAg (p<0.05). Adhesive with both 10% QADM and 0.05% NAg had less acid than those using either 10%

QADM or 0.05% NAg (p<0.05). When 10% QADM and 0.05% NAg were incorporated into both the adhesive resin and the primer, the lactic acid production was further reduced (p<0.05).

Example 3

Antibacterial Dental Adhesive Containing Silver and Amorphous Calcium Phosphate Nanoparticles The objectives of this study were to incorporate nanoparticles of silver (NAg) and nanoparticles of amorphous calcium phosphate (NACP) into a dental adhesive, and to investigate the effects on dentin bond strength and dental plaque microcosm biofilm response. Human dentin shear bond strengths ranged from 26 to 34 MPa; adding NAg and NACP did not significantly decrease the bond strength (p>0.1). Bonding agents containing NAg and NACP greatly reduced the biofilm viability and metabolic activity, compared to the control. CFU for total microorganisms, total streptococci, and *mutans* streptococci on bonding agents with NACP and NAg were an order of magnitude less than those of control. Lactic acid production for groups containing NACP and NAg were reduced to ¼ of that of control. Microcosm biofilm viability and acid production were greatly reduced on bonding agents containing NAg and NACP nanoparticles for the first time, without compromising dentin bond strength.

Materials and Methods

NAg Incorporation into Primer and Adhesive

Scotchbond Multi-Purpose (3M, St. Paul, Minn.), referred to as "SBMP", was used as the parent bonding system to test the effect of incorporation of NACP and NAg. The purpose was to investigate a model system, and then the method of incorporating NACP and NAg could be applied to other bonding agents. According to the manufacturer, SBMP etchant contained 37% phosphoric acid. SBMP primer single bottle contained 35-45% 2-Hydroxyethylmethacrylate (HEMA), 10-20% copolymer of acrylic and itaconic acids, and 40-50% water. SBMP adhesive contained 60-70% BisGMA and 30-40% HEMA.

Silver 2-ethylhexanoate powder (Strem, New Buryport, Mass.) was dissolved in 2-(tert-butylamino)ethyl methacrylate (TBAEMA, Sigma) at 0.08 g of silver salt per 1 g of TBAEMA, following previous studies (Cheng Y J. et al. 2011; Cheng L. et al. 2011). TBAEMA was used because it improves the solubility by forming Ag—N coordination bonds with Ag ions, thereby facilitating the Ag salt to dissolve in the resin solution. TBAEMA was selected since it contains reactive methacrylate groups and can be chemically incorporated into a resin upon photopolymerization. This method produced NAg with a mean particle size of 2.7 nm that were well dispersed in the resin (Cheng Y J. et al. 2011; Cheng L. et al. 2011). To incorporate NAg into the primer, the aforementioned Ag-TBAEMA solution was mixed with the SBMP primer at a silver 2-ethylhexanoate/(primer+silver 2-ethylhexanoate) of 0.1% by mass; this mass fraction was selected based on previous studies (Cheng Y J. et al. 2011; Cheng L. et al. 2011). To incorporate NAg into the adhesive, the Ag-TBAEMA was mixed with the SBMP adhesive at 0.1% mass fraction.

Addition of NACP into Adhesive

Nanoparticles of ACP ($Ca_3[PO_4]_2$) were synthesized using a spray-drying technique as described previously (Xu et al. 2006; Chow et al. 2004). Briefly, calcium carbonate ($CaCO_3$, Fisher, Fair Lawn, N.J.) and dicalcium phosphate anhydrous ($CaHPO_4$, Baker Chemical, Phillipsburg, N.J.) were dissolved into an acetic acid solution to obtain final Ca and $PO_4$ ionic concentrations of 8 mmol/L and 5.333 mmol/L, respectively. The Ca/P molar ratio for the solution was 1.5, the same as that for ACP. The solution was sprayed into the heated chamber of the spray-drying apparatus. The dried particles were collected via an electrostatic precipitator (AirQuality, Minneapolis, Minn.), yielding NACP with a mean particle size of 116 nm (Xu et al. 2011).

The NACP were mixed with the adhesive containing 0.1% silver 2-ethylhexanoate. The NACP mass fractions in the adhesive were: 0%, 10%, 20%, 30%, and 40%, following previous studies on NACP nanocomposites (Xu et al. 2011; Moreau et al. 2011).

Hence, six bonding agents were tested:

[1]. SBMP primer, SBMP adhesive (termed "SBMP control").
[2]. Primer+0.1% NAg, adhesive+0.1% NAg (termed "P&A+NAg". P=primer, A=adhesive).
[3]. Primer+0.1% NAg, adhesive+0.1% NAg+10% NACP (termed "P&A+NAg, A+10NACP").
[4]. Primer+0.1% NAg, adhesive+0.1% NAg+20% NACP (termed "P&A+NAg, A+20NACP").
[5]. Primer+0.1% NAg, adhesive+0.1% NAg+30% NACP (termed "P&A+NAg, A+30NACP").
[6]. Primer+0.1% NAg, adhesive+0.1% NAg+40% NACP (termed "P&A+NAg, A+40NACP").

Dentin Shear Bond Strength Testing and SEM Examination

Extracted caries-free human third molars were cleaned and stored in 0.01% thymol solution. The tips of the molar crowns were cut off via a diamond saw (Isomet, Buehler, Lake Bluff, Ill.) to yield flat mid-coronal dentin surfaces. Following a previous study (Antonucci et al. 2009), the tooth was embedded in a poly-carbonate holder (Bosworth, Skokie, Ill.) and ground perpendicular to the longitudinal axis using 320-grit SiC paper until there was no occlusal enamel left. The bonding procedures are shown in FIG. 4A. Briefly, the dentin surface was etched with 37% phosphoric acid gel for 15 s and rinsed with water for 15 s (Antonucci et al. 2009). The primer was applied with a brush-tipped applicator and rubbed in for 15 s, and the solvent was removed with a stream of air. The adhesive was then applied and photo-cured for 10 s (Optilux VCL 401, Demetron Kerr, Danbury, Conn.). Then, a stainless-steel iris with a central opening (diameter=4 mm, thickness=1.5 mm) was held against the adhesive-treated dentin surface. The central opening was filled with a composite (TPH, Caulk/Dentsply, Milford, Del.) and photo-cured for 60 s.

The bonded specimens were stored in distilled water at 37° C. for 24 h (Antonucci et al. 2009). Then, the dentin shear bond strength, $S_D$, was measured as schematically shown in FIG. 4B. The chisel was connected with a computer-controlled Universal Testing Machine (MTS, Eden Prairie, Minn.), held parallel to the composite-dentin interface, and loaded at 0.5 mm/min until the bond failed. $S_D$ was calculated as: $S_D=4P/(\pi d^2)$, where P is the load at failure, and d is the diameter of the composite. Ten teeth were tested for each group (n=10).

For scanning electron microscopy (SEM) examination, the bonded tooth was cut through the center parallel to the longitudinal axis via a diamond saw (Isomet) with copious water. The sectioned surface was polished with increasingly finer SiC paper up to 4000 grit. Following a previous study (Imazato et al. 2007), the polished surface was treated with 50% phosphoric acid for 30 s, then with 10% NaOCl for 2 min. After being thoroughly rinsed with water for 10 min, the specimens were air dried and then sputter-coated with gold. Three specimens were prepared for each group. The specimens were then examined in an SEM (Quanta 200, FEI, Hillsboro, Oreg.).

Specimen Fabrication for Biofilm Experiments

Following previous studies (Imazato et al. 1998; Li et al. 2009), layered disk specimens were made as shown in FIG. 3A (Example 3). A polyethylene mold (inner diameter=9 mm, thickness=2 mm) was situated on a glass slide. A primer was applied into the mold to cover the glass. After drying with a stream of air, an adhesive was applied and cured for 20 s with Optilux. A composite (TPH) was placed on the adhesive to completely fill the mold, and light-cured for 1 min. The bonded specimens were immersed in water and agitated for 1 h to remove any uncured monomer (Imazato et al. 1998). The disks were then dried and sterilized with ethylene oxide (Anprolene AN 74i, Andersen, Haw River, N.C.).

Dental Plaque Microcosm Model and Live/Dead Assay

Saliva is ideal for growing dental plaque microcosm biofilms in vitro which maintain much of the complexity and heterogeneity of dental plaque in vivo (McBain et al. 2009). The dental plaque microcosm model was approved by the University of Maryland. Saliva was collected from a healthy adult donor having natural dentition without active caries or periopathology, and without the use of antibiotics within the last 3 months (Cheng L. et al. 2011). The donor did not brush teeth for 24 h and abstained from food/drink intake for at least 2 h prior to donating saliva. Stimulated saliva was collected during parafilm chewing and kept on ice. The saliva was diluted in sterile glycerol to a concentration of 30%, and stored at −80° C. (Cheng L. et al. 2011).

The saliva-glycerol stock was added, with 1:50 final dilution, to a growth medium as inoculum. The growth medium contained mucin (type II, porcine, gastric) at a concentration of 2.5 g/L; bacteriological peptone, 2.0 g/L; tryptone, 2.0 g/L; yeast extract, 1.0 g/L; NaCl, 0.35 g/L; KCl, 0.2 g/L; $CaCl_2$, 0.2 g/L; cysteine hydrochloride, 0.1 g/L; haemin, 0.001 g/L; vitamin K1, 0.0002 g/L, at pH 7 (McBain et al. 2005). The inoculum was cultured in an incubator (5% $CO_2$, 37° C.) for 24 h. Each disk was placed into a well of 24-well plates, with the primer on the top. Then, 1.5 mL of inoculum was added to each well, and incubated for 8 h. The disks were transferred to new 24-well plates with fresh medium and incubated. After 16 h, the disks were transferred to new 24-well plates with fresh medium and incubated for 24 h. This totaled 2 d of incubation, which was shown in a previous study to be sufficient to form microcosm biofilms (Cheng L. et al. 2011).

Disks with 2-d biofilms were washed three times with phosphate buffered saline (PBS), and then stained using a live/dead bacterial kit (Molecular Probes, Eugene, Oreg.). Live bacteria were stained with Syto 9 to produce a green fluorescence, and bacteria with compromised membranes were stained with propidium iodide to produce a red fluorescence. Specimens were examined with an epifluorescence microscope (TE2000-S, Nikon, Melville, N.Y.).

MTT Assay of Metabolic Activity

MTT (3-[4,5-Dimethylthiazol-2-yl]-2,5-diphenyltetrazolium bromide) assay was used to measure the metabolic activity of biofilms (Cheng Y J. et al. 2011; Antonucci et al. 2011). MTT is a colorimetric assay that measures the enzymatic reduction of MTT, a yellow tetrazole, to formazan. Each disk with the 2-d biofilm was transferred to a new 24-well plate. One mL of MTT dye (0.5 mg/mL MTT in PBS) was added to each well and incubated for 1 h. During this process, metabolically active bacteria reduced the MTT to purple formazan. After 1 h, the disks were transferred to a new 24-well plate, 1 mL of dimethyl sulfoxide (DMSO) was added to solubilize the formazan crystals, and the plate was incubated for 20 min in the dark. After mixing via pipetting, 200 μL of the DMSO solution from each well was transferred to a 96-well plate, and the absorbance at 540 nm (optical density OD540) was measured via a microplate reader (SpectraMax M5, Molecular Devices, Sunnvale, Calif.). A higher absorbance is related to a higher formazan concentration, which indicates a higher metabolic activity in the biofilm adherent on the disk.

Lactic Acid Production and Colony Forming Unit (CFU) Counts

Disks with 2-d biofilms were rinsed with cysteine peptone water (CPW) to remove loose bacteria, and transferred to 24-well plates containing buffered peptone water (BPW) plus 0.2% sucrose. The samples were incubated for 3 h to allow the biofilms to produce acid. The BPW solutions were then stored for lactate analysis. Lactate concentrations were determined using an enzymatic (lactate dehydrogenase) method (Cheng L. et al. 2011). The microplate reader was used to measure the absorbance at 340 nm (optical density $OD_{340}$) for the collected BPW solutions. Standard curves were prepared using a lactic acid standard (Supelco, Bellefonte, Pa.).

Disks with biofilms were transferred into tubes with 2 mL CPW, and the biofilms were harvested by sonication and vortexing via a vortex mixer (Fisher, Pittsburgh, Pa.). Three types of agar plates were used. First, tryptic soy blood agar culture plates were used to determine total microorganisms (Cheng L. et al. 2011). Second, *mitis salivarius* agar (MSA) culture plates, containing 15% sucrose, were used to determine total streptococci (Lima et al. 2009). This is because MSA contains selective agents crystal violet, potassium tellurite and trypan blue, which inhibit most gram-negative bacilli and gram-positive bacteria except streptococci, thus enabling streptococci to grow (Lima et al. 2009). Third, cariogenic *mutans* streptococci are known to be resistant to bacitracin, and this property was used to isolate *mutans* streptococci from the oral microflora. The MSA agar plates with 0.2 units of bacitracin per mL were used to determine *mutans* streptococci.

One-way analysis of variance (ANOVA) was performed to detect the significant effects of the variables. Tukey's multiple comparison was used to compare the data at a p value of 0.05.

Results

Figure 9:
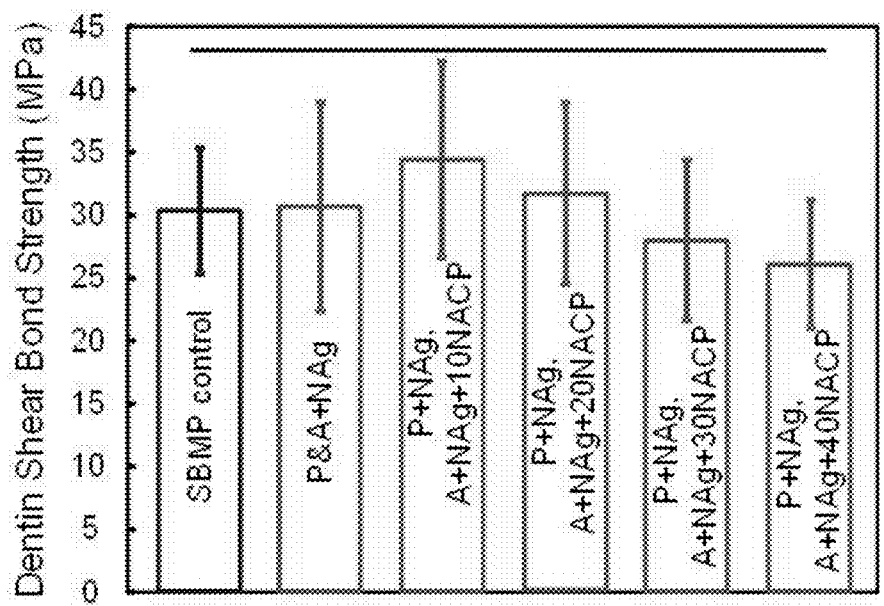
FIG. 9. Human dentin shear bond strengths. Each value is mean±sd (n=10). The same letter at the bars indicates that all the six groups had bond strengths that were not significantly different (p>0.1).

FIG. 4A shows schematic of the bonding procedures, FIG. 4B schematic of the bond test, and FIG. 9 human dentin shear bond strength data (mean±sd; n=10). Adding 0.1% NAg into primer and adhesive yielded a bond strength of (30.7±8.3) MPa, similar to (30.2±5.0) MPa for the control (p>0.1). Further adding 10% NACP into the adhesive slightly increased the bond strength to (34.3±7.7) MPa (p>0.1). While 40% NACP slightly decreased the bond strength, all the six groups had bond strengths that were not significantly different (p>0.1).

Figure 10:
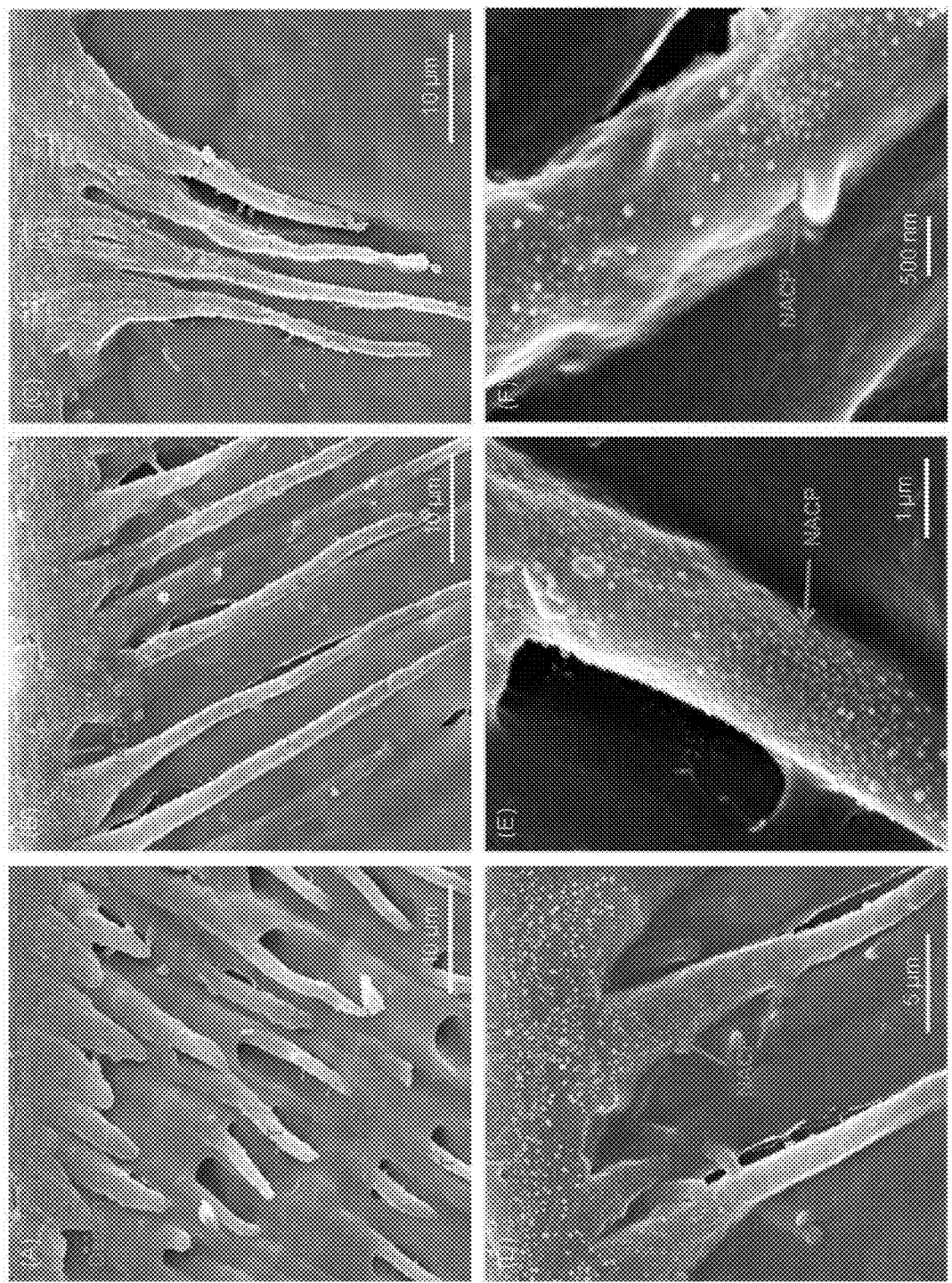
FIG. 10. SEM micrographs of dentin-adhesive interfaces. (A) SBMP control, (B) P&A+NAg, A+20NACP, (C) P&A+ NAg, A+40NACP. (D) P&A+NAg, A+20NACP at a higher magnification, and (E, F) at even higher magnifications. Adhesives filled the dentinal tubules and formed resin tags "T" for all six groups. "HL" indicates the hybrid layer between the adhesive and the underlying mineralized dentin. High magnification SEM in (D-F) revealed numerous NACP nanoparticles in the adhesive layer, in the hybrid zone, and inside the dentinal tubules. Arrows in (D-F) indicate NACP in the dentinal tubules. NACP were not only able to infiltrate with the adhesive into straight tubules (E), but also into bent and irregularly-shaped tubules (F).

Typical SEM images of the dentin-adhesive interfaces are shown in FIG. 10 for (A) SBMP control, (B) P&A+NAg, A+20NACP, and (C) P&A+NAg, A+40NACP. Numerous resin tags "T" from well-filled dentinal tubules were visible in all the samples. The resin tags were slightly shorter at 40% NACP than the other groups. "HL" refers to the hybrid layer between the adhesive and the underlying mineralized dentin. At a higher magnification, the NACP nanoparticles were visible in (D) with 20% NACP. Arrows in (D) indicate examples of NACP nanoparticles infiltrated into the dentinal tubules. This feature became more visible at higher magnifications in (E) and (F), where arrows indicate NACP, which infiltrated into not only the straight and smooth tubules (E), but also the bent and irregularly-shaped tubules (F).

Figure 11:
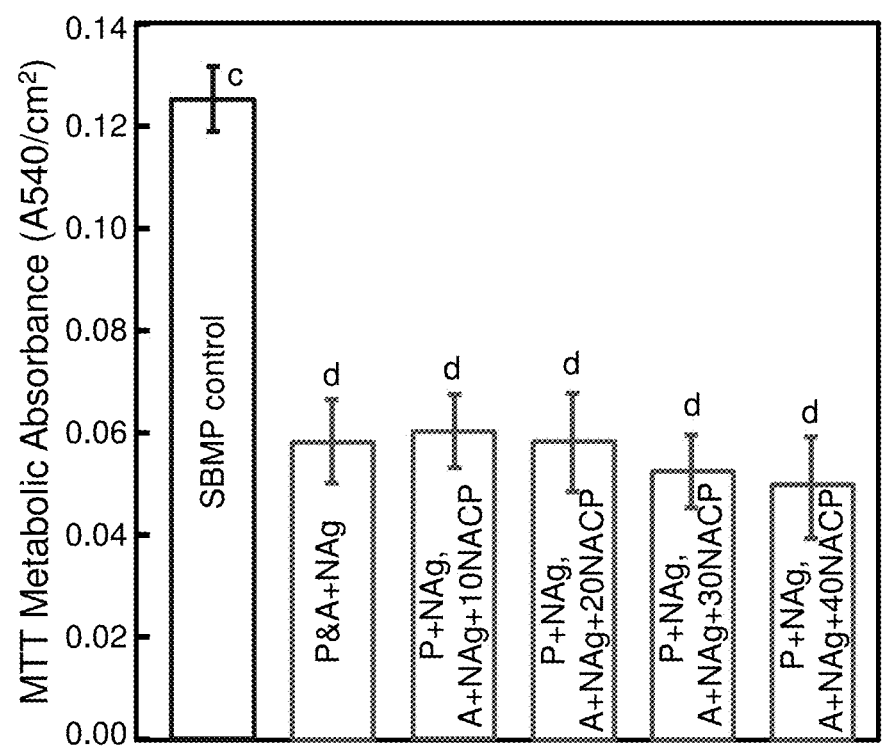
FIG. 11. MTT assay on metabolic activity of biofilms on specimens of the six groups (mean±sd; n=6). Control disks had biofilms with a relatively high metabolic activity, indicating no antibacterial effect. However, all the bonding agents modified with NAg and NACP decreased the metabolic activity by more than half. Values with dissimilar letters are significantly different (p<0.05).

The MTT metabolic results are plotted in FIG. 11. Control disks had biofilms with a high metabolic activity. Incorporation of 0.1% of NAg decreased the metabolic activity by more than half (p<0.05). Adding NACP to the adhesive did not further significantly decrease the metabolic activity, although there was a decreasing trend at 30% and 40% NACP (p>0.1).

Figure 12:
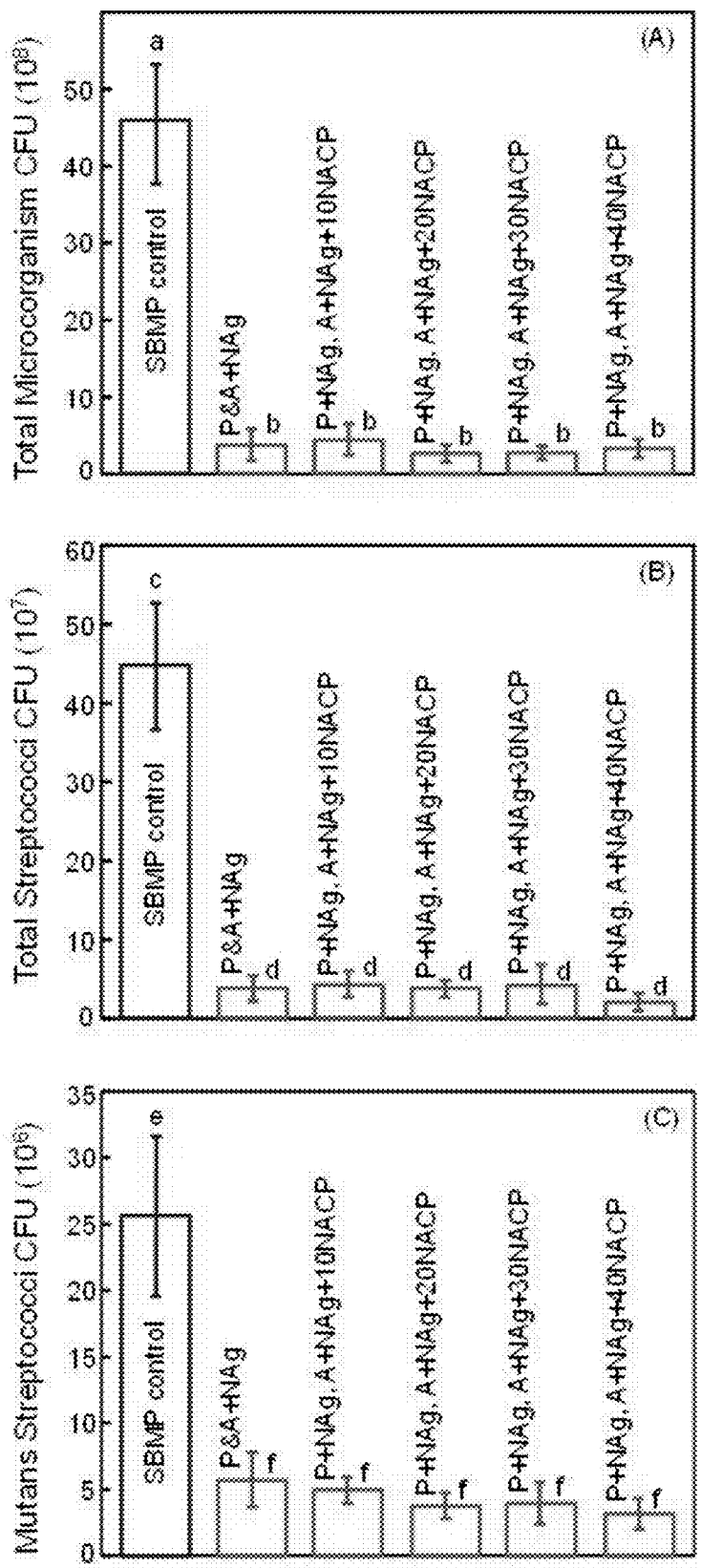
FIG. 12. Microcosm biofilm CFU per disk for: (A) Total microorganisms, (B) total streptococci, and (C) *mutans* streptococci (mean±sd; n=6). In each plot, values with dissimilar letters are significantly different (p<0.05). The modified bonding systems reduced the CFU counts by about an order of magnitude, compared to the commercial control. Therefore, the bonding agents containing NAg and NACP were strongly antibacterial.

FIG. 12 plots biofilm CFU counts per disk for: (A) Total microorganisms, (B) total streptococci, and (C) *mutans* streptococci. NAg greatly reduced the CFU compared to that of the control (p<0.05). Specimens with NAg and NACP reduced the CFU by an order of magnitude, compared to the control. Specimens with 40% NACP slightly reduced the CFU, compared to P&A+NAg without NACP; however, this decrease was not statistically significant (p>0.1).

Figure 13:
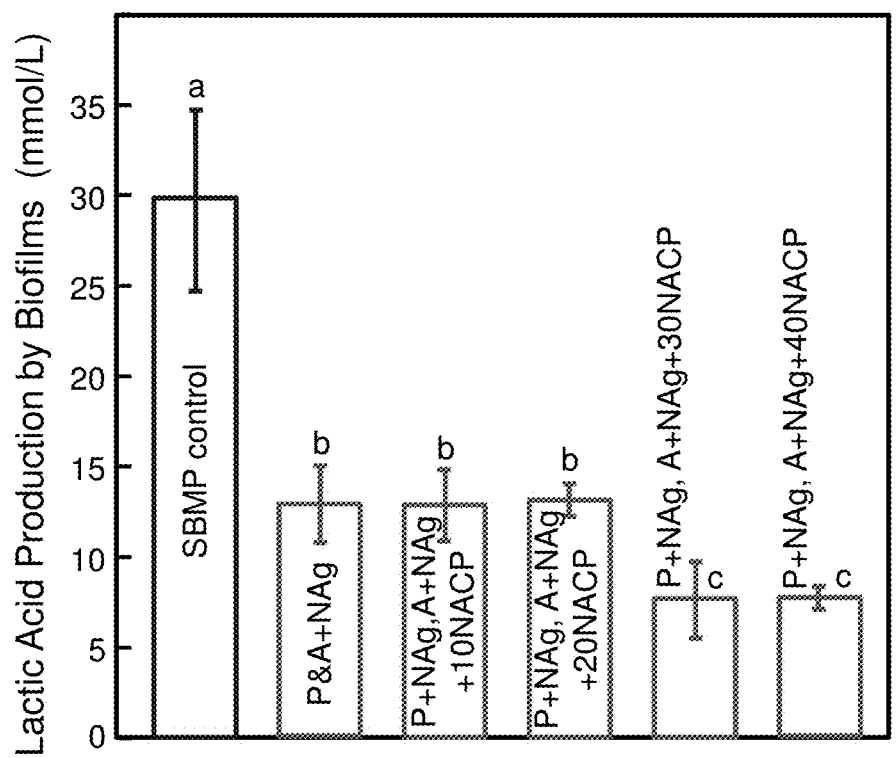
FIG. 13. Lactic acid production by biofilms for the six groups (mean±sd; n=6). Acid production by biofilms on disks with NAg plus 30% and 40% NACP were approximately ¼ of that on the control, indicating a potent antibacterial effect of specimens containing NAg and NACP. Values with dissimilar letters are significantly different (p<0.05).

FIG. 13 plots the lactic acid production by biofilms. Biofilms on control disks produced the most acid, indicating that the un-modified commercial bonding agent was not antibacterial. Incorporation of NAg dramatically decreased the acid production, to less than half of that of the control (p<0.05). Adding 30% and 40% NACP slightly and significantly (p<0.05) decreased the acid production, compared to P&A+NAg without NACP. Lactic acid production by biofilms on the disks with 30% and 40% NACP were about ¼ of the acid production for the control.

Example 4

Figure 14:
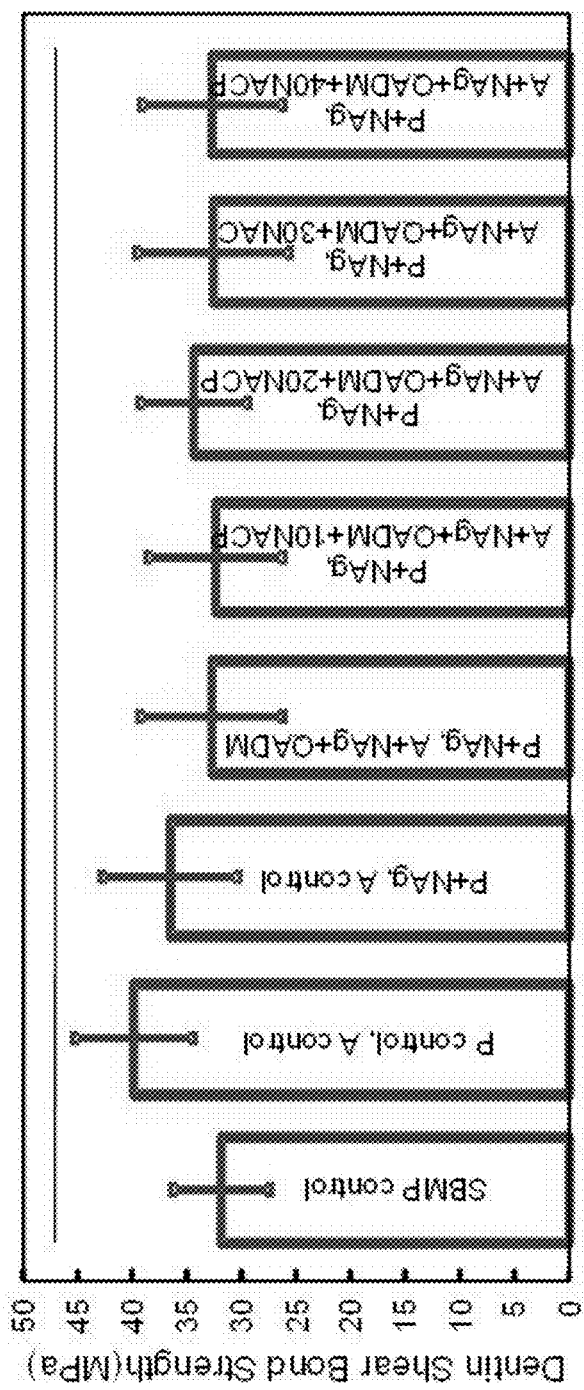
FIG. 14. Dentin Shear Bond Strength of Anti-bacterial, Re-mineralizing Primer/Adhesive Dental Bonding Agents.

Dentin Shear Bond Strength of Anti-Bacterial, Re-Mineralizing Primer/Adhesive Dental Bonding Agents Dental primer/adhesive bonding agents were prepared as described below, and dentin shear bond strength was measured as described in the preceding Examples. The results are provided in FIG. 14.

Group 1: Scotchbond Multi-Purpose (3M, St. Paul, Minn.), referred to as "SBMP control".

Group 2: Experimental Primer=PMGDM/HEMA at 3.3/1 ratio+1% BAPO+50% acetone (Referred to as "P control"). Experimental Adhesive=BisGMA/TEGMA at 7/3 ratio+1% BAPO (Referred to as "A control").

Group 3: P control+0.1% nano silver. A control was not modified. Referred to as "P+NAg, A control".

Group 4: P control+0.1% nano silver. A control+0.1% nano silver+10% QADM. Referred to as "P+NAg, A+NAg+QADM".

Group 5: P control+0.1% nano silver. A control+0.1% nano silver+10% QADM+10% NACP. Referred to as "P+NAg, A+NAg+QADM+10NACP".

Group 6: P control+0.1% nano silver. A control+0.1% nano silver+20% QADM+20% NACP. Referred to as "P+NAg, A+NAg+QADM+20NACP".

Group 7: P control+0.1% nano silver. A control+0.1% nano silver+10% QADM+30% NACP. Referred to as "P+NAg, A+NAg+QADM+30NACP".

Group 8: P control+0.1% nano silver. A control+0.1% nano silver+10% QADM+40% NACP. Referred to as "P+NAg, A+NAg+QADM+40NACP".

Each value is mean±sd; n=10). Horizontal lines in FIG. 14 indicate values that are not significantly different (p>0.1). These results demonstrate that the antibacterial and remineralizing bonding agents of the invention have the promise of achieving antibacterial and remineralizing capabilities in an experimental bonding agent without compromising the dentin bond strength.

Example 5

Synthesis of Quaternary Ammonium Methacrylates with Different Alkyl Chain Lengths Synthesis of a variety of quaternary ammonium salt (QAS) monomethacrylates was carried out using a Menschutkin reaction (Menschutkin et al. 1890; Antonucci et al. 2012). The reaction proceeds by the addition reaction of tertiary amines with organo-halides. To form a QAS with a reactive methacrylate groups, 2-(dimethylamino)ethyl methacrylate (DMAEMA) was chosen as methacrylate-containing tertiary amine. In order to investigate the effect of chain length from the quaternary ammonium site on the antibacterial properties of QAS monomers, seven different alkyl organo-halides were each chosen to react with BEMA.

Examples are summarized in Table 2. Other chain lengths including 2, 4, 5, 7, 8, 10, 11, 13, 14, 16, 17, 19, 20, 21, 23, 24, and 25 can be similarly synthesized.

TABLE 2

Summary of the Reaction of Dimethylamino methacrylate (DMAEMA) with Various Organo-Halides

| Tertiary Amine | Alkyl Organo-Halide | Product | Alkyl Chain Length |
|---|---|---|---|
| Dimethylamino methacrylate (DMAEMA) | 1-bromopropane (BP) | DMAPM | 3 |
| | 1-bromohexane (BH) | DMAHM | 6 |
| | 1-bromoheptane (BHP) | DMAHPM | 7 |
| | 1-bromooctane (BO) | DMAOM | 8 |
| | 1-bromononane (BN) | DMANM | 9 |
| | 1-bromodecane (BD) | DMADM | 10 |
| | 1-bromoundecane (BUD) | DMAUDM | 11 |
| | 1-bromododecane (BDD) | DMADDM | 12 |
| | 1-bromotridecane (BTD) | DMATDM | 13 |
| | 1-bromotetradecane (BTTD) | DMATTDM | 14 |
| | 1-bromopentadecane (BPD) | DMAPDM | 15 |
| | 1-bromohexadecane (BHD) | DMAHDM | 16 |
| | 1-bromoheptadecane (BHPD) | DMAHPDM | 17 |
| | 1-bromooctadecane (BOD) | DMAODM | 18 |
| | 1-bromononadecane(BND) | DMANDM | 19 |
| | 1-bromoicosane (BIO) | DMAIOM | 20 |
| | 1-bromohenicosane (BHO) | DMAHOM | 21 |
| | 1-bromodocosane (BDO) | DMADOM | 22 |

Synthesis of QAS with Chain Length=3

In a 20 mL scintillation vial, 10 mmol of 2-(dimethylamino)ethyl methacrylate (DMAEMA, Sigma Aldrich, St. Louis Mo.) and 10 mmol of 1-bromopropane (BP, TCI America, Portland Oreg.) were added. To this mixture, 3 g of ethanol was added as a solvent. A magnetic stir bar was added, and the vial was capped and stirred at 70° C. for 24 h. After the reaction was complete, the ethanol solvent was removed via evaporation at room temperature over several days.

Synthesis of QAS with Chain Length=6

In a 20 mL scintillation vial, 10 mmol of DMAEMA and 10 mmol of 1-bromohexane (BH, TCI America, Portland Oreg.) were added. To this mixture, 3 g of ethanol was added as a solvent. A magnetic stir bar was added, and the vial was capped and stirred at 70° C. for 24 h. After the reaction was complete, the ethanol solvent was removed via evaporation at room temperature over several days.

Synthesis of QAS with Chain Length=9

In a 20 mL scintillation vial, 10 mmol of DMAEMA and 10 mmol of 1-bromononane (BN, TCI America, Portland Oreg.) were added. To this mixture, 3 g of ethanol was added as a solvent. A magnetic stir bar was added, and the vial was capped and stirred at 70° C. for 24 h. After the reaction was complete, the ethanol solvent was removed via evaporation at room temperature over several days.

Synthesis of QAS with Chain Length=12

In a 20 mL scintillation vial, 10 mmol of DMAEMA and 10 mmol of 1-bromododecane (BDD, TCI America, Portland Oreg.) were added. To this mixture, 3 g of ethanol was added as a solvent. A magnetic stir bar was added, and the vial was capped and stirred at 70° C. for 24 h. After the reaction was complete, the ethanol solvent was removed via evaporation at room temperature over several days.

Synthesis of QAS with Chain Length=15

In a 20 mL scintillation vial, 10 mmol of DMAEMA and 10 mmol of 1-bromopentadecane (BPD, TCI America, Portland Oreg.) were added. To this mixture, 3 g of ethanol was added as a solvent. A magnetic stir bar was added, and the vial was capped and stirred at 70° C. for 24 h. After the reaction was complete, the ethanol solvent was removed via evaporation at room temperature over several days.

Synthesis of QAS with Chain Length=18

In a 20 mL scintillation vial, 10 mmol of DMAEMA and 10 mmol of 1-bromooctadecane (BOD, TCI America, Portland Oreg.) were added. To this mixture, 3 g of ethanol was added as a solvent. A magnetic stir bar was added, and the vial was capped and stirred at 70° C. for 24 h. After the reaction was complete, the ethanol solvent was removed via evaporation at room temperature over several days.

Synthesis of QAS with Chain Length=22

In a 20 mL scintillation vial, 10 mmol of DMAEMA and 10 mmol of 1-bromodocosane (BDO, TCI America, Portland Oreg.) were added. To this mixture, 3 g of ethanol was added as a solvent. A magnetic stir bar was added, and the vial was capped and stirred at 70° C. for 24 h. After the reaction was complete, the ethanol solvent was removed via evaporation at room temperature over several days.

Characterization of Reaction Products

FTIR spectra (Nicolet 6700, Thermo Scientific, Waltham, Mass.) of the starting materials and the viscous products were collected between two KBr windows in the 4000 cm$^{-1}$ to 400 cm$^{-1}$ region with 128 scans at 4 cm$^{-1}$ resolution. Water and $CO_2$ bands were removed from all spectra by subtraction. $^1$H NMR spectra (GSX 270, JEOL USA Inc., Peabody, Mass.) of the starting materials and products were taken in deuterated chloroform at a concentration of approximately 3%. All spectra were run at room temperature, 15 Hz sample spinning, 45° tip angle for the observation pulse, and a 10 s recycle delay, for 64 scans.

Cytotoxicity of Monomers Via MTT Assay

Human gingival fibroblasts (HGF, ScienCell) were cultured in a fibroblast medium (FM). Each unpolymerized monomer was dissolved in FM, at concentrations of: 0 (control), 0.5, 1, 2, 5, 10, 20, 40, 60, and 100 µg/mL (Huang L et al. 2011; Chai Z et al. 2011). Then, HGF were seeded in 96-well plates at 5,000 cells per well. After 2 d, 20 µL of MTT solution was added (Chai Z et al. 2011). After 4 h, the unreacted dye was removed and 150 µL of dimethyl sulfoxide was added. Absorbance was measured via the microplate reader at 492 nm. Relative fibroblast viability=absorbance of monomer sample/absorbance of control without monomer (Chai Z et al. 2011). The results are provided in FIG. 15A.

Figure 15:
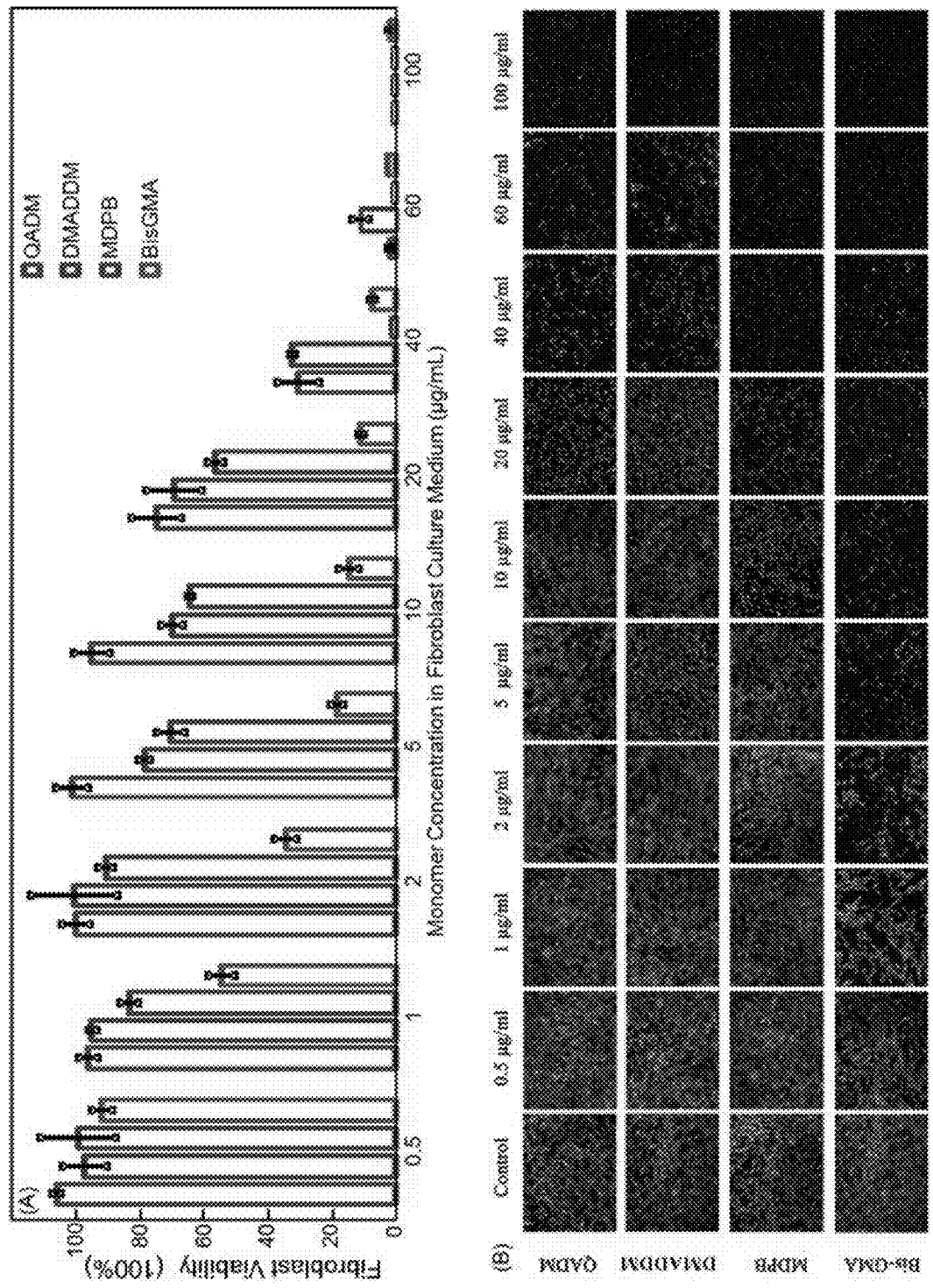
FIGS. 15A-B. Increasing the monomer concentration decreased the fibroblast viability (n=6). At each concentration, the antibacterial monomer with a chain length of 12 (DMADDM) had the highest fibroblast viability (p<0.05). DMADDM and MDPB are less cytotoxic, with higher cell viability, than BisGMA, a monomer commonly used in dental resins. In each group of bars, the antibacterials QADM, DMADDM, MDPB and BisGMA appear from left to right, respectively.

Cells were also live/dead stained (Molecular Probes) and examined with fluorescence microscopy (TE2000-S, Nikon) as shown in FIG. 15B.

Incorporating Antibacterial Monomers with Different Chain Lengths into Dental Composites The composite matrix is a resin or combinations of resins selected from the group consisting of bis-GMA (bisphenol glycidyl methacrylate), TEGDMA (triethylene glycol dimethacrylate), HEMA (2-hydroxyethyl methacrylate), UDMA (urethane dimethacrylate) and PMGDM (pyromellitic acid glycerol dimethacrylate). The composite fillers may include calcium phosphate nanoparticles such as nanoparticles of amorphous calcium phosphate (NACP). The NACP particles range in size from about 10 nm to about 500 nm. The NACP filler level ranges from about 5% to about 90% of the mass of the composite. The composite can contain other fillers such as usual dental glass fillers. Alternatively, the composite may contain glass fillers, without calcium phosphate fillers, in which the incorporation of the new antibacterial monomers will render the composite strongly antibacterial. The new antibacterial composite may contain fibers and whiskers as mechanical reinforcement.

One or more antibacterial monomers with various chain lengths can be incorporated into the composite, at antibacterial resin mass fractions ranging from 1% to 50% of the composite, preferably 2% to 20% of the composite. Other techniques for producing the dental composites are disclosed in WO 2012/003290, incorporated herein by reference in its entirety.

Data on Longer Chain Length

A new antibacterial monomer with a chain length of 16 was also prepared which exhibited a MBC=0.61 µg/mL and a MIC=0.305 µg/mL. These values are an order of magnitude more potent than those for chain length 12 reported below.

Example 6

Alternative Means for Synthesis of Quaternary Ammonium Methacrylates (QAMs)

A modified Menschutkin reaction approach was used to synthesize the new QAMs. This method uses a tertiary amine group to react with an organo-halide, as described in previous studies (Antonucci J M et al. 2012; Cheng L et al. 2012a). A benefit of this reaction is that the reaction products are generated at virtually quantitative amounts and require minimal purification (Antonucci J M et al. 2012). In the present study, 2-bromoethyl methacrylate (BEMA) was the organo halide. N,N-dimethylaminohexane (DMAH) and 1-(dimethylamino) docecane (DMAD) were the two tertiary amines.

The scheme of synthesis of dimethylaminohexane methacrylate (DMAHM) is shown in FIG. 16A. Ten mmol of DMAH (Tokyo Chemical Industry, Tokyo, Japan), 10 mmol of BEMA (Monomer-Polymer and Dajac Labs, Trevose, Pa.), and 3 g of ethanol were added to a 20 mL scintillation vial with a magnetic stir bar. The vial was capped and stirred at 70° C. for 24 h. After the reaction was complete, the ethanol solvent was removed via evaporation at room temperature over several days. This yielded DMAHM as a clear liquid.

Figure 16:
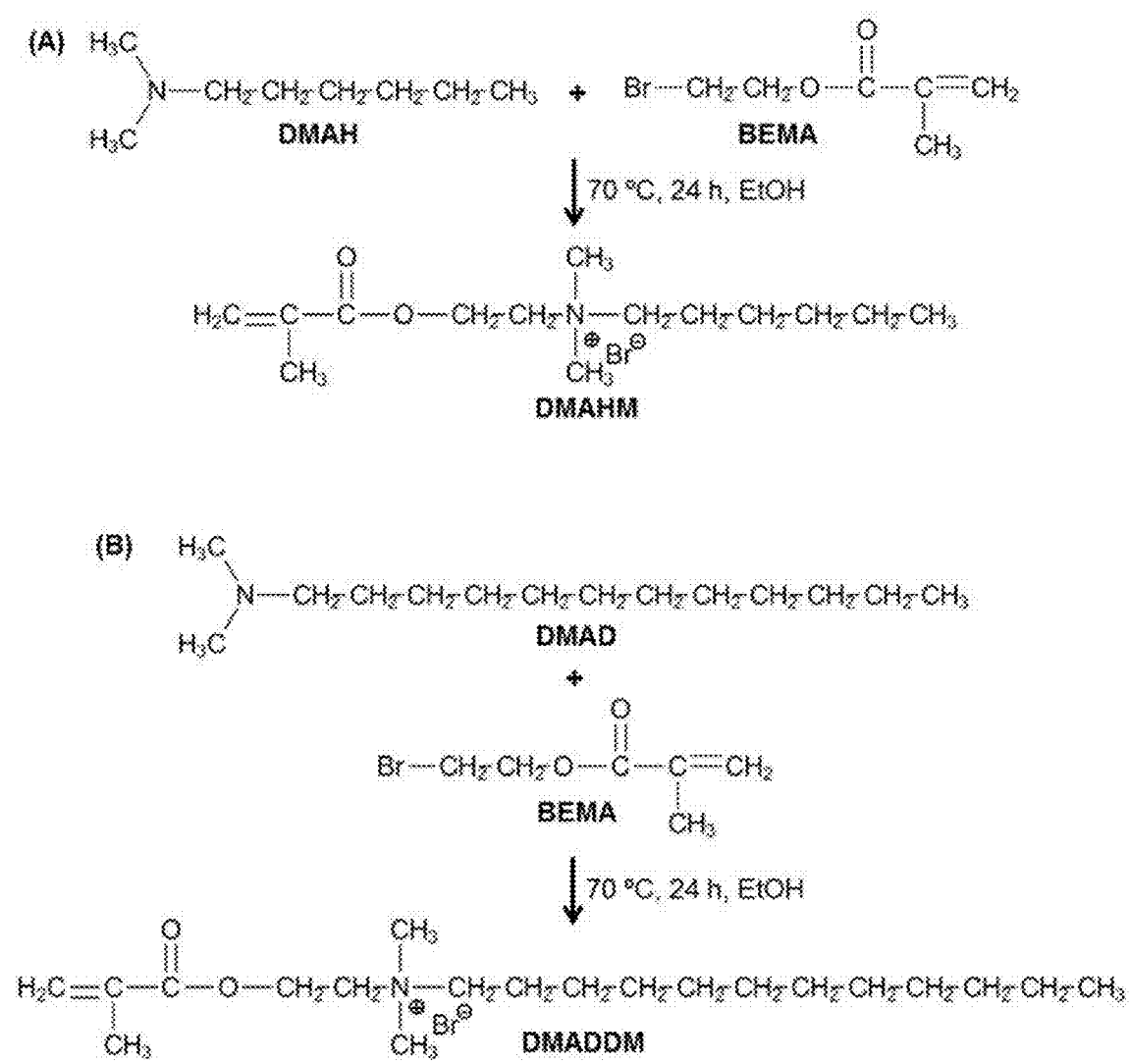
FIG. 16. A modified Menschutkin reaction was used to synthesize antibacterial monomers: (A) DMAHM, and (B) DMADDM. DMAH=N,N-dimethylaminohexane.

The scheme of synthesis of dimethylaminododecyl methacrylate (DMADDM) is shown in FIG. 16B. In a 20 mL scintillation vials were added 10 mmol of DMAD (Tokyo Chemical Industry), 10 mmol of BEMA, and 3 g of ethanol. A magnetic stir bar was added, and the vial was capped and stirred at 70° C. for 24 h. After the reaction was complete, the solvent was removed via evaporation. The number of the alkyl chain length units was 6 for DMAHM and 12 for DMADDM (FIG. 16).

To characterize the reaction products, Fourier transform infrared spectroscopy (FTIR, Nicolet 6700, Thermo Scientific, Waltham, Mass.) was used. FTIR spectra of the starting materials and the viscous products were collected between two KBr windows in the 4000 cm$^{-1}$ to 400 cm$^{-1}$ region with 128 scans at 4 cm$^{-1}$ resolution (Antonucci J M et al. 2012). Water and $CO_2$ bands were removed from all spectra by subtraction. $^1$H NMR spectra (GSX 270, JEOL, Peabody, Mass.) of the starting materials and products were taken in deuterated chloroform at a concentration of approximately 3%. All spectra were run at room temperature, 15 Hz sample spinning, 45° tip angle for the observation pulse, and a 10 s recycle delay, for 64 scans (Antonucci J M et al. 2012).

Figure 17:
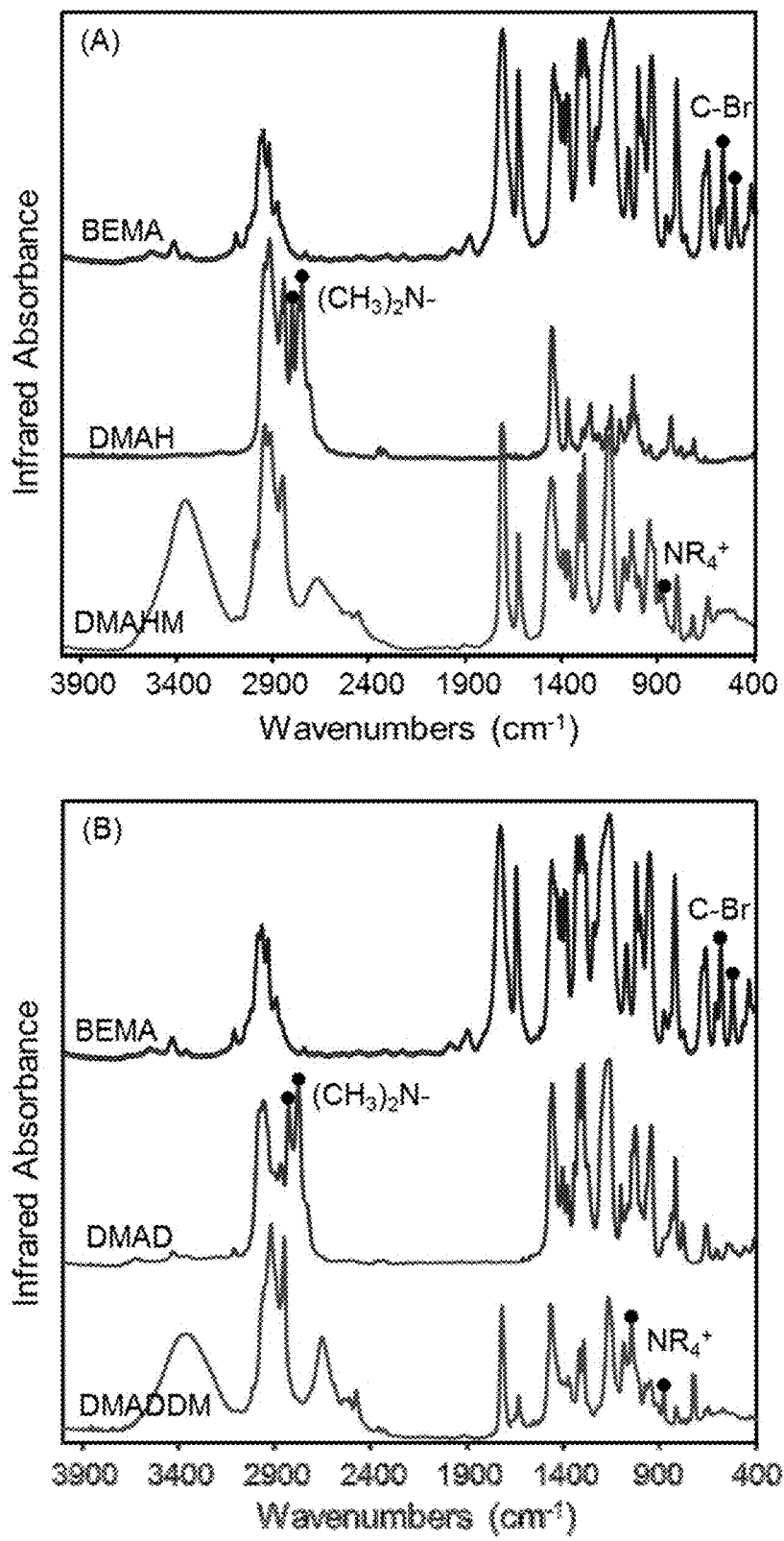

Representative results are provided in FIG. 17. The characterization using FTIR and $^1$H NMR indicated that the Menschutkin reaction was successful. The infrared spectroscopy showed the disappearance of C—Br and tertiary amine groups, and the appearance of quaternary ammonium group that resulted from the reaction. In each plot, the appearance of the $NR_4^+$ peak in the last curve corresponded to the formation of the quaternary ammonium group. In FIG. 17A, FTIR showed that the C—Br absorption bands from BEMA (575 cm$^{-1}$, 512 cm$^{-1}$) in curve 1 and the $(CH_3)_2N^-$ bands (2822 cm$^{-1}$, 2771 cm$^{-1}$) from DMAH in curve 2 disappeared in curve 3. This indicated that the bromine group in BEMA successfully reacted with the amine group in DMHA to form the quaternary ammonium group. The appearance in curve 3 of the $NR_4^+$ peak corresponded to the formation of the quaternary ammonium group and, hence, DMAHM was successfully synthesized. Similarly, FIG. 17B showed the synthesis of DMADDM from the reaction of BEMA and DMAD.

Minimum Inhibitory Concentration (MIC) and Bactericidal Concentration (MBC)

MIC and MBC were measured using S. mutans (ATCC 700610, UA159, American Type Culture, Manassas, Va.). S. mutans is a cariogenic, aerotolerant anaerobic bacterium and the primary causative agent of dental caries (Loesche 1986). MIC and MBC were determined via serial microdilution assays (Imazato S et al. 2006; Huang L et al. 2011). Unpolymerized DMAHM or DMADM monomer was dissolved in brain heart infusion (BHI) broth (BD, Franklin Lakes, N.J.) to give a final concentration of 200 mg/mL. From these starting solutions, serial two fold dilutions were made into 1 mL volumes of BHI broth. 15 µL of stock S. mutans was added to 15 mL of BHI broth with 0.2% sucrose and incubated at 37° C. with 5% $CO_2$. Overnight cultures of S. mutans were adjusted to $2 \times 10^6$ CFU/mL with BHI broth, and 50 µL of inocula was added to each well of a 96-well plate containing 50 µL of a series of antibacterial monomer dilution broths. BHI broth with $1 \times 10^6$ CFU/mL bacteria suspension without antibacterial agent served as negative control. Chlorhexidine diacetate (CHX) (Sigma, St. Louis, Mo.) served as positive control. The previously-synthesized QADM (Antonucci J M et al. 2012; Cheng L et al. 2012a) served as an antibacterial monomer control. After incubation at 37° C. in 5% $CO_2$ for 48 h, the wells were read for turbidity, referenced by the negative and positive control wells. MIC was determined as the endpoint (the well with the lowest antibacterial agent concentration) where no turbidity could be detected with respect to the controls (Huang L et al. 2011). To determine MBC, an aliquot of 50 µL from each well without turbidity was inoculated on BHI agar plates and incubated at 37° C. in 5% $CO_2$ for 48 h. MBC was determined as the lowest concentration of antibacterial agent that produced no colonies on the plate. The tests were performed in triplicate (Huang L et al. 2011). The MIC and MBC values of the antibacterial agents against S. mutans are listed in Table 3.

TABLE 3

MIC and MBC values of various antibacterial agents against S. mutans*

| Compound | MBC | MIC |
|---|---|---|
| QADM | $2.5 \times 10^4$ µg/mL | $1.25 \times 10^4$ µg/mL |
| DMAHM | $3.13 \times 10^3$ µg/mL | $1.56 \times 10^3$ µg/mL |
| DMADDM | 12.21 µg/mL | 6.10 µg/mL |
| CHX | 3.91 µg/mL | 1.95 µg/mL |

*CHX = Chlorlhexidine. QADM = quaternary ammonium dimethacrylate. DMAHM = dimethylaminohexane methacrylate. DMADDM = dimethylaminododecyl methacrylate. Tests were repeated in triplicate.

A lower concentration of the antibacterial agent needed to inhibit the bacteria indicates a higher antibacterial potency. The new DMAHM with an alkyl chain length of 6 was more potent than the previously-synthesized QADM. In dramatic contrast, the new DMADDM with an alkyl chain length of 12 was much more strongly antibacterial than DMAHM. The MIC and MBC of DMADDM was more than two orders of magnitude lower than those of MDAHM, and approached those of the CHX control.

Processing of DMADDM-NACP Nanocomposite

A spray-drying technique as described previously in Chow L C et al. (2004) was used to make NACP ($Ca_3[PO_4]_2$). Calcium carbonate ($CaCO_3$, Fisher, Fair Lawn, N.J.) and dicalcium phosphate anhydrous ($CaHPO_4$, Baker Chemical, Phillipsburg, N.J.) were dissolved into an acetic acid solution to obtain final Ca and P ionic concentrations of 8 mmol/L and 5.333 mmol/L, respectively. This resulted in a Ca/P molar ratio of 1.5, the same as that for ACP. This solution was sprayed into a heated chamber, and an electrostatic precipitator (AirQuality, Minneapolis, Minn.) was used to collect the dried particles. This method produced NACP with a mean particle size of 116 nm, as measured in a previous study (Xu H H K et al. 2011). Other techniques for producing NACP are disclosed in WO 2012/003290, incorporated herein by reference in its entirety.

Because DMADDM exhibited a much greater antibacterial potency than DMAHM and QADM, DMADDM was used for incorporation into the NACP nanocomposite to obtain antibacterial properties. BisGMA (bisphenol glycidyl dimethacrylate) and TEGDMA (triethylene glycol dimethacrylate) (Esstech, Essington, Pa.) were mixed at a mass ratio=1:1, and rendered light-curable with 0.2% camphorquinone and 0.8% ethyl 4-N,N-dimethylaminobenzoate (mass fractions). DMADDM was mixed with the photoactivated BisGMA-TEGDMA resin at the following DMADDM/(BisGMA-TEGDMA+DMADDM) mass fractions: 0%, 2.5%, 5%, 7.5% and 10%, yielding five groups of resin, respectively. A dental barium boroaluminosilicate glass of a median particle size of 1.4 µm (Caulk/Dentsply, Milford, Del.) was silanized with 4% 3-methacryloxypropyltrimethoxysilane and 2% n-propylamine (Xu H H K et al. 2011). The NACP and glass particles were mixed into each resin, at the same filler level of 70% by mass, with 20% of NACP and 50% of glass (Xu H H K et al. 2011). Because the resin mass fraction was 30% in the composite, the five DMADDM mass fractions in the composite were 0%, 0.75%, 1.5%, 2.25% and 3%, respectively. Other techniques for producing the dental composites are disclosed in WO 2012/003290, incorporated herein by reference in its entirety.

Six composites were tested: Five NACP nanocomposites at the five DMADDM mass fractions described above, and a commercial control composite. Renamel (Cosmedent, Chicago, Ill.) served as a control composite. It consisted of nanofillers of 20-40 nm in size, at 60% filler level in a multifunctional methacrylate ester resin. For mechanical testing, each paste was placed into rectangular molds of 2×2×25 mm. For biofilm experiments, each paste was placed into disk molds of 9 mm in diameter and 2 mm in thickness. The specimens were photo-cured (Triad 2000, Dentsply, York, Pa.) for 1 min on each side. The specimens were then incubated in distilled water at 37° C. for 24 hours prior to mechanical or biofilm testing.

Mechanical Testing

A computer-controlled Universal Testing Machine (5500R, MTS, Cary, N.C.) was used to fracture the specimens in three-point flexure using a span of 10 mm and a crosshead speed of 1 mm/min. Flexural strength S was measured as: $S=3P_{max}L/(2bh^2)$, where $P_{max}$ is the load-at-failure, L is span, b is specimen width and h is specimen thickness. Elastic modulus E was measured as: $E=(P/d)(L^3/[4bh^3])$, where load P divided by displacement d is the slope in the linear elastic region of the load-displacement curve. The specimens were taken out of the water and fractured within several minutes while still being wet (Cheng L et al. 2012a).

Figure 18:
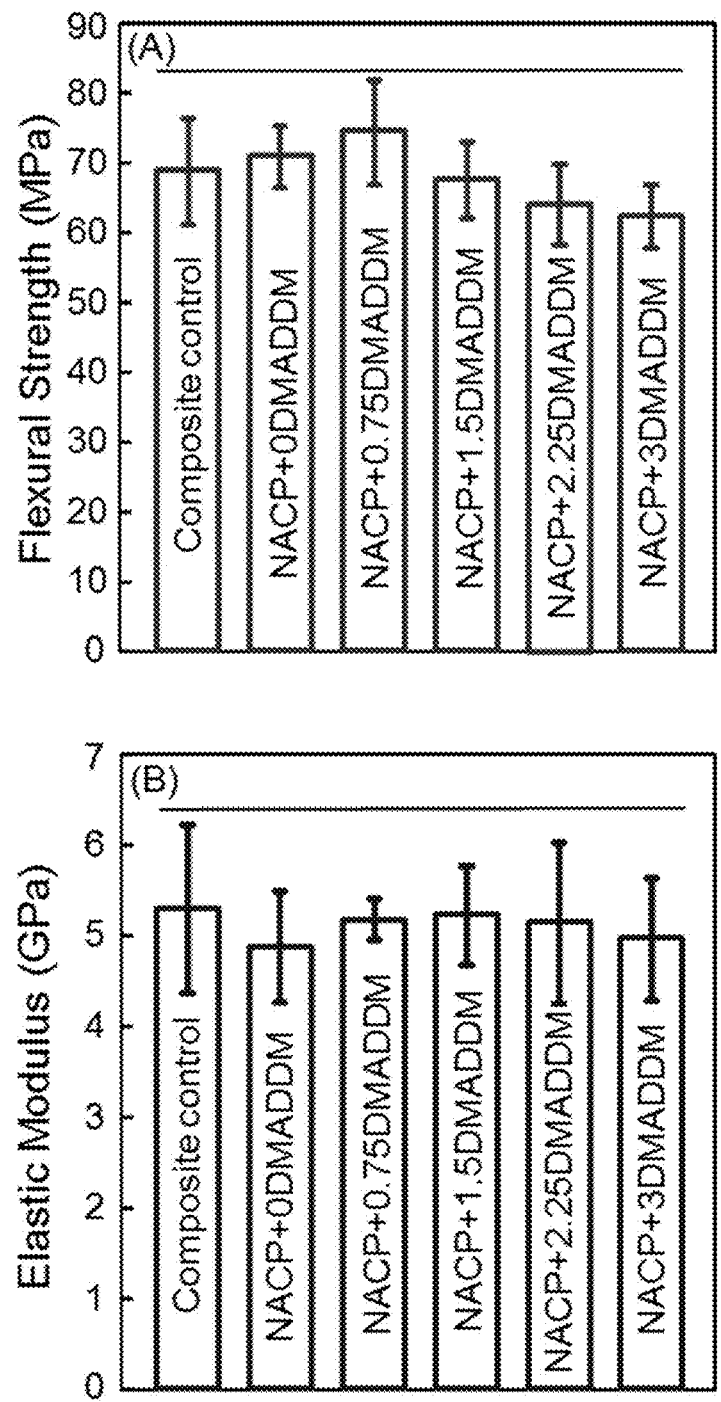

FIG. 18 plots (A) flexural strength, and (B) elastic modulus of the composites (mean±sd; n=6). The NACP nanocomposite with various DMADDM mass fractions had strengths similar to that of the commercial composite control, which was not antibacterial and had no Ca and P ion release ($p>0.1$). The elastic moduli of DMADDM-NACP nanocomposites were also similar to those of the NACP nanocomposite without DMADDM and the composite control ($p>0.1$).

Dental Plaque Microcosm Biofilm and Live/Dead Assay

The dental plaque microcosm biofilm model used human saliva as inoculum. Saliva was collected from a healthy adult donor following a previous study (Cheng L et al. 2012b). The donor had natural dentition without active caries or periopathology, and without the use of antibiotics within the last 3 months. The donor did not brush teeth for 24 h and abstained from food or drink intake for at least 2 h prior to donating saliva (Cheng L et al. 2012b). Stimulated saliva was collected during parafilm chewing and kept on ice. The saliva was diluted in sterile glycerol to a concentration of 70% saliva and 30% glycerol (Cheng L et al. 2012b), and stored at −80° C.

The saliva-glycerol stock was added, with 1:50 final dilution, into the growth medium as inoculum. The growth medium contained mucin (type II, porcine, gastric) at a concentration of 2.5 g/L; bacteriological peptone, 2.0 g/L; tryptone, 2.0 g/L; yeast extract, 1.0 g/L; NaCl, 0.35 g/L; KCl, 0.2 g/L; $CaCl_2$, 0.2 g/L; cysteine hydrochloride, 0.1 g/L; haemin, 0.001 g/L; vitamin $K_1$, 0.0002 g/L, at pH 7 (McBain A J 2009). Composite disks were sterilized in ethylene oxide (Anprolene AN 74i, Andersen, Haw River, N.C.). 1.5 mL of inoculum was added to each well of 24-well plates with a composite disk, and incubated in 5% $CO_2$ at 37° C. for 8 h. The disks were then transferred to new 24-well plates filled with fresh medium and incubated. After 16 h, the disks were transferred to new 24-well plates with fresh medium and incubated for 24 h. This totaled 48 h of incubation, which was shown to be adequate to form dental plaque microcosm biofilms on resins (Cheng L et al. 2012b; Zhang K et al. 2012).

After 48 h of growth, the microcosm biofilms adherent on the disks were gently washed three times with phosphate buffered saline (PBS), and then stained using the BacLight live/dead bacterial viability kit (Molecular Probes, Eugene, Oreg.) (Cheng L et al. 2012b; Zhang K et al. 2012). Live bacteria were stained with Syto 9 to produce a green fluorescence, and bacteria with compromised membranes were stained with propidium iodide to produce a red fluorescence. The stained disks were examined using a confocal laser scanning microscopy (CLSM 510, Carl Zeiss, Thornwood, N.Y.).

Biofilms on composite control and NACP nanocomposite without DMADDM had primarily live bacteria (data not shown). Increasing the DMADDM mass fraction in the nanocomposite resulted in much more red/yellow/orange staining, indicating that the DMADDM-containing nanocomposites effectively inhibited the biofilm growth. These results also indicate that NACP was not antibacterial, and DMADDM was responsible for the antibacterial activity.

MTT Assays

MTT (3-(4,5-Dimethylthiazol-2-yl)-2,5-diphenyltetrazolium bromide) assay was performed according to previous studies (Antonucci J M et al. 2012; Cheng L et al. 2012a). It is a colorimetric method that measures the enzymatic reduction of MTT, a yellow tetrazole, to formazan. Briefly, disks with 48-h biofilms were rinsed with PBS and transferred to 24 well plates. Then, 1 mL of MTT dye (0.5 mg/mL MTT in PBS) was added to each well and incubated for 1 h. The disks were transferred to new 24-well plates, 1 mL of dimethyl sulfoxide (DMSO) was added to solubilize the formazan crystals, and the plate was incubated for 20 min in the dark. Then, 200 µL of the DMSO solution from each well was transferred to a 96-well plate, and the absorbance at 540 nm was measured via a microplate reader (SpectraMax M5, Molecular Devices, Sunnvale, Calif.) (Cheng L et al. 2012a).

Figure 19:
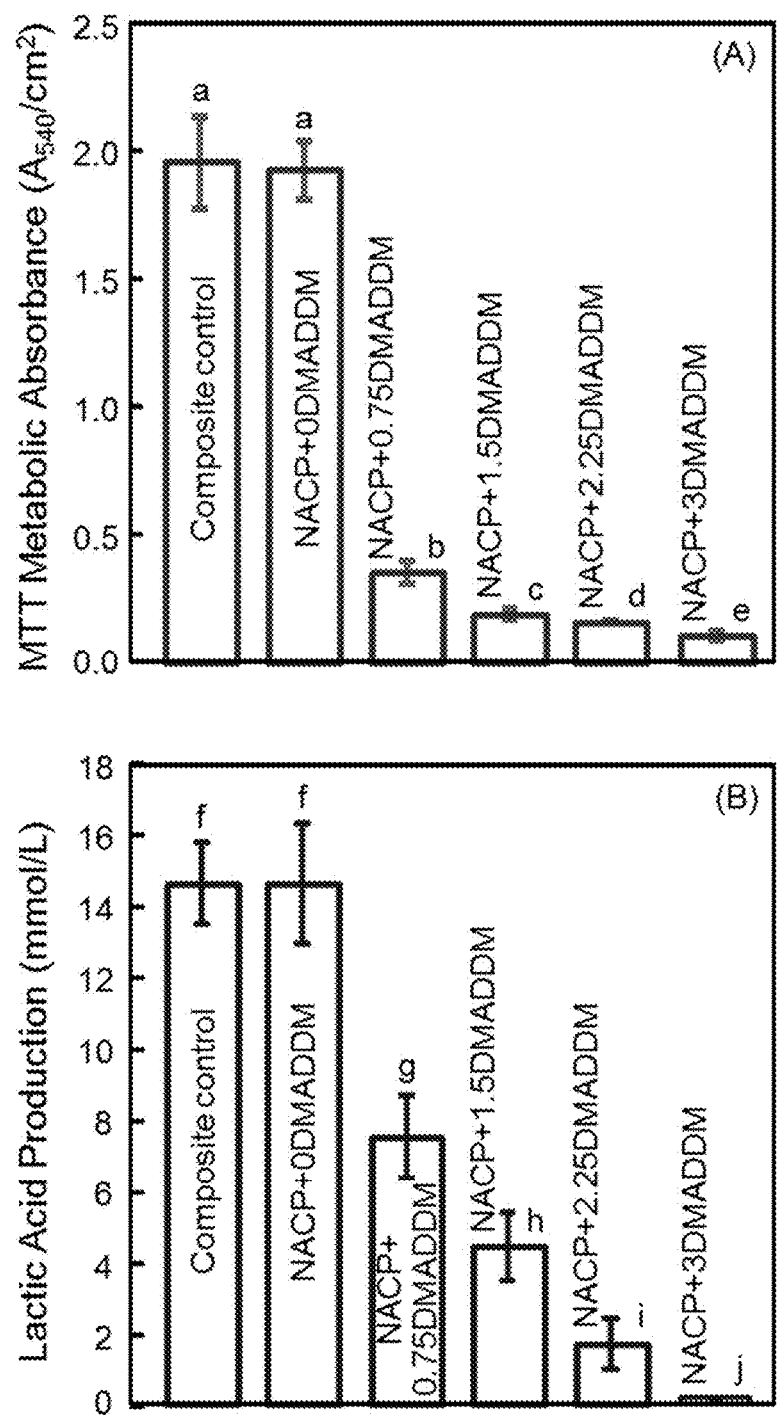

FIG. 19 plots (A) the MTT assay, and (B) lactic acid production of biofilms adherent on the composites. Each values is mean±sd (n=6). In (A), the biofilms on composite control and NACP+0% DMADDM had a similar metabolic activity ($p>0.1$). Increasing the DMADDM mass fraction significantly decreased the metabolic activity of biofilms ($p<0.05$). At 3% DMADDM in the composite, the metabolic activity was approximately 5% of that on composite control. In (B), the biofilms on composite control produced the most acid, similar to that on NACP+0% DMADDM. With increasing DMADDM mass fraction, the lactic acid production monotonically decreased ($p<0.05$). The lactic acid production by biofilms on NACP+3% DMADDM was about 1% of that on the commercial composite control.

Lactic Acid Production and CFU Counts

Composite disks with 48-h biofilms were rinsed in cysteine peptone water (CPW) to remove the loose bacteria. Each disk was placed in a new 24-well plate and 1.5 mL of buffered peptone water (BPW) supplemented with 0.2% sucrose (Cheng L et al. 2012a). The samples were incubated in 5% $CO_2$ at 37° C. for 3 h to allow the biofilms to produce acid. The BPW solutions were then stored for lactate analysis. Lactate concentrations were determined using an enzymatic (lactate dehydrogenase) method according to previous studies (Cheng L et al. 2012a; Cheng L et al. 2012b). The microplate reader was used to measure the absorbance at 340 nm for the collected BPW solutions. Standard curves were prepared using a lactic acid standard (Supelco Analytical, Bellefonte, Pa.) (Cheng L et al. 2012a; Cheng L et al. 2012b).

Composite disks with 2-day biofilms were transferred into tubes with 2 mL CPW, and the biofilms were harvested by sonication and vortexing at the maximum speed for 20 seconds using a vortex mixer (Fisher, Pittsburgh, Pa.). Three types of agar plates were used to assess the microorganism viability after serial dilution in CPW: *Mitis salivarius* agar (MSA) culture plates, containing 15% sucrose, to determine total streptococci (Lima J P et al. 2009); MSA agar culture plates plus 0.2 units of bacitracin per mL, to determine *mutans* streptococci (Park J H et al. 2006); and Tryptic Soy Blood Agar culture plates to determine total microorganisms (Cheng L et al. 2012b). One-way analysis of variance (ANOVA) was performed to detect the significant effects of the variables. Tukey's multiple comparison test was used at a p value of 0.05.

Figure 20:
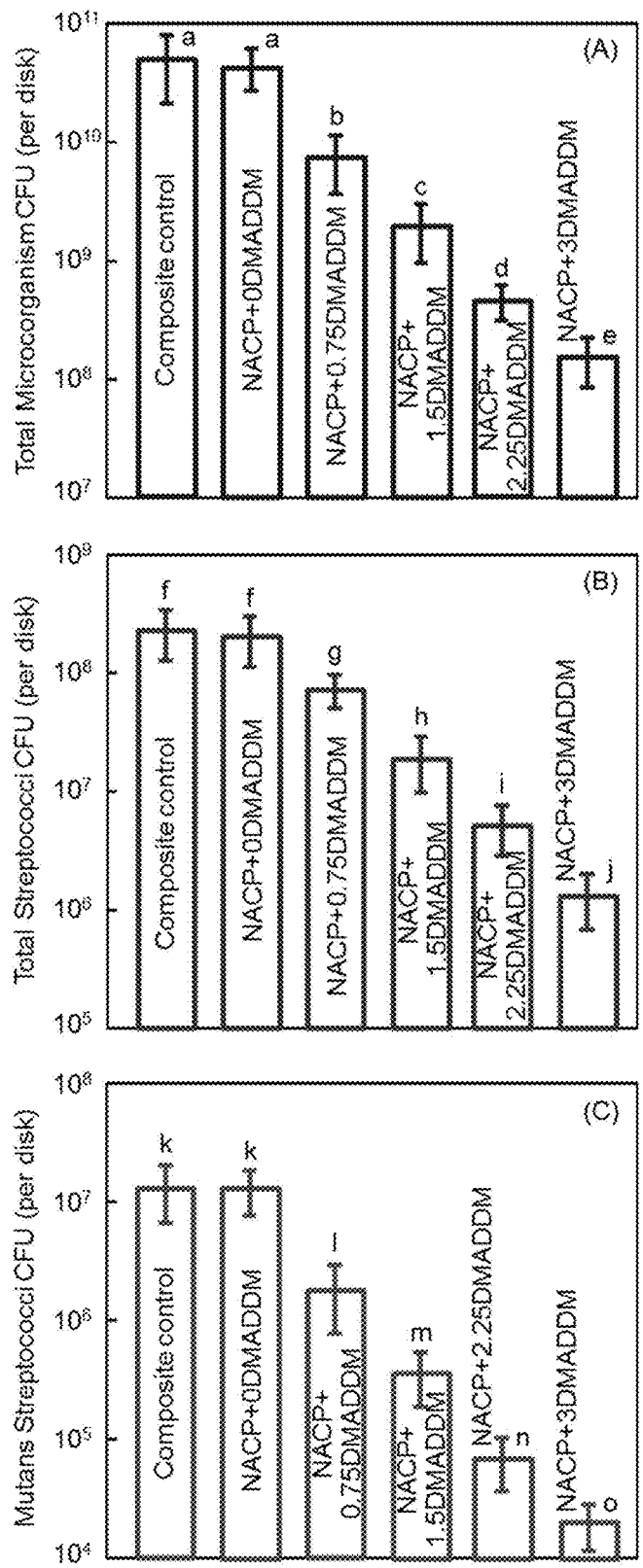

FIG. 20 plots the CFU counts for: (A) Total microorganisms, (B) total streptococci, and (C) *mutans* streptococci (mean±sd; n=6). The composite control had the highest CFU counts. All three CFU counts showed a similar decreasing trend with increasing DMADM mass fraction in NACP nanocomposite (p<0.05). Compared to the control composite, all three CFU counts on NACP+3% DMADDM were reduced by 2-3 orders of magnitude.

The present study demonstrated that the antibacterial monomers, such as DMADDM, could be incorporated into the NACP nanocomposite to impart a strong antibacterial activity without compromising mechanical properties. This indicates the versatility of incorporating various types of antibacterial monomers into the NACP nanocomposite, and the miscibility and compatibility of the antibacterial monomers with NACP nanocomposite. It is interesting to compare the DMADDM nanocomposite of the present study with the previous QADM nanocomposite tested by the same operator using the same procedures (Cheng et al. 2012c). The previous QADM nanocomposite reduced the MTT metabolic activity by 2-fold, compared to the same control composite (Cheng L et al. 2012c). The present study using DMADDM reduced the MTT by 20-fold. In addition, the previous QADM nanocomposite reduced the lactic acid production by 2-fold (Cheng L et al. 2012c); the present study using DMADDM reduced lactic acid by 2 orders of magnitude. Furthermore, the previous QADM nanocomposite reduced the biofilm CFU counts by 3-fold (Cheng L et al. 2012c); the present study using DMADDM reduced the biofilm CFU by 2-3 orders of magnitude. Therefore, the new DMADDM-NACP nanocomposite represents a substantial improvement over previous antibacterial dental composites.

Example 7

DMADDM Bond Strength Durability at 1 Day and at 6 Months

Extracted human molar teeth were used (n=10). The monomer DMADDM and nanoparticles of silver (NAg) were incorporated into a commercial bonding agent SBMP. The bonded dentin samples were immersed in water for 1 day and 6 months, to test the degradation of bond strength over time. The commercial control lost ⅓ of its strength in 6 months, which is unusual for commercial bonding agents (FIG. 21). In contrast, the antibacterial bonding agents showed no loss of dentin bond strength. These results demonstrate the double benefits of the new antibacterial bonding agents: inhibiting biofilms and caries, and improving the durability of the mechanical strength of the bonded interface.

Example 8

The objectives of the study were to develop antibacterial dental primer and dental adhesive containing a new quaternary ammonium monomer (dimethylaminododecyl methacrylate, DMADDM) as well as nanoparticles of silver (NAg), and to investigate their effects on antibacterial and dentin bond properties. The minimum inhibitory concentration (MIC) and minimum bactericidal concentration (MBC) of the new DMADDM were orders of magnitude lower than those of a previously-synthesized quaternary ammonium dimethacrylates (QADM). Un-cured dental primer containing DMADDM produced much larger bacteria inhibition zones than QADM (p<0.05). Cured primer/adhesive samples containing DMADDM and NAg greatly reduced biofilm metabolic activity (p<0.05). Combining DMADDM with NAg in primer/adhesive resulted in less CFU than DMADDM alone (p<0.05). Lactic acid production by biofilms was reduced by 20-fold via DMADDM and NAg, compared to commercial bonding agent control. Incorporation of the new DMADDM and NAg into primer and adhesive did not adversely affect the dentin bond strength.

Materials and Methods

Developing New Antibacterial Monomers

Two new antibacterial monomers were synthesized: dimethylaminohexane methacrylate (DMAHM) with an alkyl chain length of 6, and dimethylaminododecyl methacrylate (DMADDM) with an alkyl chain length of 12. A modified Menschutkin reaction method was employed, which used a tertiary amine group to react with an organo-halide, following previous studies (Antonucci et al. 2012; Cheng et al. 2012a; Cheng et al. 2012a). This method is useful because the reaction products are generated at virtually quantitative amounts and require minimal purification (Antonucci et al. 2012). To synthesize DMAHM, 2-bromoethyl methacrylate (BEMA) served as the organo halide, and N,N-dimethylaminohexane (DMAH) served as the tertiary amine. Ten mmol of DMAH (Tokyo Chemical Industry, Tokyo, Japan), 10 mmol of BEMA (Monomer-Polymer and Dajac Labs, Trevose, Pa.), and 3 g of ethanol were added to a 20 mL scintillation vial with a magnetic stir bar. The vial was capped and stirred at 70° C. for 24 h. After the reaction was complete, the ethanol solvent was removed via evaporation, yielding DMAHM as a clear, colorless, and viscous liquid. To synthesize the second new monomer DMADDM, BEMA was the organo halide, and 1-(dimethylamino)docecane (DMAD) was the tertiary amine. In a 20 mL scintillation vials were added 10 mmol of DMAD (Tokyo Chemical Industry) and 10 mmol of BEMA, while otherwise following the same procedures as for DMAHM. Fourier transform infrared (FTIR) spectroscopy (Nicolet 6700, Thermo Scientific, Waltham, Mass.) spectra of the starting materials and the products were collected between two KBr windows in the 4000 to 400 $cm^{-1}$ region. $^1$H NMR spectra (GSX 270, JEOL) were taken in deuterated chloroform at a concentration of about 3% (Antonucci et al. 2012). The reactions and products of DMAHM and DMADDM were all verified in preliminary studies.

Minimum Inhibitory Concentration (MIC) and Minimum Bactericidal Concentration (MBC)

The use of *S. mutans* (ATCC 700610, American Type Culture, Manassas, Va.) was approved by the University of Maryland. *S. mutans* is a cariogenic, aerotolerant anaerobic bacterium and the primary causative agent of dental caries (Deng et al. 2004). MIC and MBC were determined via serial microdilution assays (Imazato et al. 2006; Huang et al. 2011). Unpolymerized DMAHM or DMADDM monomer was dissolved in brain heart infusion (BHI) broth (BD, Franklin Lakes, N.J.) to a concentration of 200 mg/mL. From these starting solutions, serial two fold dilutions were made into 1 mL volumes of BHI broth. Fifteen µL of stock S. mutans was added to 15 mL of BHI broth with 0.2% sucrose and incubated at 37° C. with 5% $CO_2$. Overnight cultures of S. mutans were adjusted to $2 \times 10^6$ CFU/mL with BHI, and 50 µL of inoculum was added to each well of a 96-well plate containing 50 µL of a series of antibacterial monomer dilution broths. BHI with $1 \times 10^6$ CFU/mL bacteria suspension without antibacterial agent served as negative control. Chlorhexidine diacetate (CHX) (Sigma, St. Louis, Mo.) served as positive control. The previously-synthesized QADM (Antonucci et al. 2012; Cheng et al. 2012a) served as an antibacterial monomer control. The wells were read for turbidity after incubation at 37° C. in 5% $CO_2$ for 48 h, referenced by the negative and positive control wells. MIC was defined as the endpoint (the well with the lowest antibacterial agent concentration) where no turbidity could be detected with respect to the controls (Huang et al. 2011). An aliquot of 50 µL from each well without turbidity was inoculated on BHI agar plates. After incubation at 37° C. in 5% $CO_2$ for 48 h, the MBC value was defined as the lowest concentration of antibacterial agent that produced no colonies on the plate. The tests were performed in triplicate (Huang et al. 2011).

Fabrication of Antibacterial Primer and Adhesive

Scotchbond Multi-Purpose (3M, St. Paul, Minn.), referred to as "SBMP", was used as the parent bonding system to test the effect of incorporation of antibacterial agents. According to the manufacturer, SBMP etchant contains 37% phosphoric acid. SBMP primer contains 35-45% 2-Hydroxyethylmethacrylate (HEMA), 10-20% copolymer of acrylic and itaconic acids, and 40-50% water. SBMP adhesive contains 60-70% BisGMA and 30-40% HEMA.

DMAHM was mixed with SBMP primer at a DMAHM/(primer+DMAHM) mass fraction of 5%. The 5% was selected following a previous study (Imazato et al. 2006). Similarly, 5% of DMAHM was incorporated into the SBMP adhesive. The second new monomer, DMADDM, was also incorporated into the SBMP primer and adhesive at 5% mass fraction.

Another antibacterial agent NAg was also incorporated into the primer and adhesive. Silver 2-ethylhexanoate powder (Strem, New Buryport, Mass.) was dissolved in 2-(tert-butylamino)ethyl methacrylate (TBAEMA, Sigma) at 0.1 g of silver salt per 0.9 g of TBAEMA (Cheng et al. 2012a; Cheng Y J. et al. 2011). TBAEMA was used because it improves the solubility by forming Ag—N coordination bonds with Ag ions, thereby facilitating the Ag salt to dissolve in the resin solution. TBAEMA was selected since it contains reactive methacrylate groups and therefore can be chemically incorporated into a dental resin upon photopolymerization (Cheng Y J. et al. 2011). This method produced NAg with a mean particle size of 2.7 nm that were well dispersed in the resin matrix (Cheng et al. 2012a; Cheng Y J. et al. 2011). The Ag solution was mixed with SBMP primer at a silver 2-ethylhexanoate/(primer+silver 2-ethylhexanoate) mass fraction of 0.1%, following a previous study (Zhang et al. 2012). The same 0.1% was used in the SBMP adhesive to formulate the antibacterial adhesive.

Dental Plaque Microcosm Model

Human saliva is useful for growing plaque microcosm biofilms in vitro to have the advantage of maintaining much of the complexity and heterogeneity of in vivo plaques (McBain. et al. 2009). The dental plaque microcosm model was approved by the University of Maryland. Saliva was collected from a healthy adult donor having natural dentition without active caries or periopathology, and without the use of antibiotics within the past three months (Cheng et al. 2012b). The donor did not brush teeth for 24 h and abstained from food/drink intake for at least 2 h prior to donating saliva. Stimulated saliva was collected during parafilm chewing and kept on ice. Saliva was diluted in sterile glycerol to a saliva concentration of 70% and stored at −80° C. (Cheng et al. 2012b).

Agar Disk-Diffusion Test of Uncured Antibacterial Primers

Agar disk diffusion test (ADT) was used to examine the antibacterial effect of un-cured primers. Five primers were tested: SBMP control primer (referred to as "P"); P+5% QADM; P+5% DMAHM; P+5% DMADDM; P+5% DMADDM+0.1% NAg.

Three types of culture media were used: (A) Tryptic Soy Blood Agar culture plates to determine total microorganisms; (B) mitis salivarius agar (MSA) culture plates, containing 15% sucrose, to determine total streptococci; (C) MSA agar culture plates plus 0.2 units of bacitracin per mL to determine mutans streptococci. The saliva-glycerol stock was added to a growth medium containing mucin (at a concentration of 2.5 g/L), bacteriological peptone (2.0 g/L), tryptone (2.0 g/L), yeast extract (1.0 g/L), NaCl (0.35 g/L), KCl (0.2 g/L), $CaCl_2$ (0.2 g/L), and cysteine hydrochloride (0.1 g/L), at pH of 7 (McBain et al. 2009). The inoculum was incubated at 37° C. in 5% $CO_2$ for 24 h. After 24 h, 0.4 mL of bacteria suspension was swabbed across an agar plate with a diameter of 90 mm. A sterile paper disk with a diameter of 6 mm and a thickness of 1.5 mm was impregnated with 20 µL of a primer. The primer-impregnated paper disk was placed on an agar plate with bacteria, and incubated in 5% $CO_2$ at 37° C. for 48 h. Bacteria inhibition zone size=(Outer diameter of inhibition zone−paper disk diameter)/2 (Imazato et al. 2006).

Specimen Fabrication and Biofilm Culture

The MIC, MBC and ADT results showed that DMADDM was much more strongly antibacterial than DMAHM and QADM. Therefore, DMADDM was selected for incorporation into SBMP primer and adhesive for the subsequent experiments.

Six bonding agents were used in biofilm tests:

[i] SBMP control primer P and adhesive A (referred to as "SBMP P & A control")

[ii] P+5% DMADDM, with unmodified adhesive A (referred to as "P+DMADDM, A control")

[iii] P+5% DMADDM+0.1% NAg, unmodified A ("P+DMADDM+NAg, A control")

[iv] A+5% DMADDM, biofilm was cultured on adhesive without primer ("A+DMADDM, no P")

[v] A+5% DMADDM+0.1% NAg, biofilm on adhesive, no primer ("A+DMADDM+NAg, no P")

[vi] 5% DMADDM and 0.1% NAg were added to both A and P ("A&P+DMADDM+NAg")

The purpose of i-iii was to investigate the new DMADDM and its combination with NAg in cured primer on antibacterial properties (schematic in FIG. 24A). The purpose of iv and v was to examine the antibacterial effect of adhesive, with biofilms on adhesive without primer (schematic in FIG. 24B). The purpose of vi was to determine the effect of both primer and adhesive being antibacterial (FIG. 24A), instead of using antibacterial primer alone (iii), or antibacterial adhesive alone (v).

Layered disk specimens for biofilm experiments were fabricated following previous studies (Li et al. 2009; Imazato et al. 1998). A polyethylene disk mold (inner diameter=9 mm, thickness=2 mm) was situated on a glass slide. For groups i, ii, iii and vi, a primer was first applied into the mold to cover the glass slide. After drying with a stream of air, an adhesive was applied and cured for 20 s (Optilux VCL 401, Demetron Kerr, Danbury, Conn.). Then, a composite (TPH, Caulk/Dentsply, Milford, Del.) was placed on the adhesive to fill the disk mold and was light-cured for 1 min. For groups iv and v, each adhesive was applied into the mold to cover the glass slide. Then, a composite (TPH) was placed onto the adhesive to fill the disk mold and light-cured for 1 min. The disks were immersed in sterile water and agitated for 1 h to remove any uncured monomer, following a previous study (Imazato et al. 1998). The disks were then dried and sterilized with ethylene oxide (Anprolene AN 74i, Andersen, Haw River, N.C.).

The saliva-glycerol stock was added, with 1:50 final dilution, into the growth medium as inoculum, as described above. A layered disk was placed in a well of 24-well plates, and 1.5 mL of inoculum was added and incubated in 5% $CO_2$ at 37° C. for 8 h. The disks were then transferred to new 24-well plates filled with fresh medium and incubated. After 16 h, the disks were transferred to new 24-well plates with fresh medium and incubated for 24 h. Microcosm biofilms were formed on the disks with this 48 h incubation, as shown previously (Cheng et al. 2012b; Zhang et al. 2012).

MTT Assay of Biofilm Metabolic Activity

A MTT (3-[4,5-Dimethylthiazol-2-yl]-2,5-diphenyltetrazolium bromide) assay was used to examine the metabolic activity of biofilms (Cheng et al. 2012a). MTT is a colorimetric assay that measures the enzymatic reduction of MTT, a yellow tetrazole, to formazan. Disks with 2-day biofilms were transferred to a new 24-well plate, and 1 mL of MTT dye (0.5 mg/mL MTT in PBS) was added to each well and incubated at 37° C. in 5% $CO_2$ for 1 h. During this process, metabolically active bacteria reduced the MTT to purple formazan. After 1 h, the disks were transferred to a new 24-well plate, 1 mL of dimethyl sulfoxide (DMSO) was added to solubilize the formazan crystals, and the plate was incubated for 20 min at room temperature in the dark. After mixing via pipetting, 200 µL of the DMSO solution from each well was transferred to a 96-well plate, and the absorbance at 540 nm was measured via a microplate reader (SpectraMax M5, Molecular Devices, Sunnyvale, Calif.). A higher absorbance is related to a higher formazan concentration, which indicates a higher metabolic activity in the biofilm on the disk.

Colony Forming Units (CFU) and Lactic Acid Production

Disk with 2-day microcosm biofilms were rinsed with cysteine peptone water (CPW) to remove loose bacteria. The disks were then transferred to 24-well plates containing buffered peptone water (BPW) plus 0.2% sucrose, and incubated in 5% $CO_2$ at 37° C. for 3 h to allow the biofilms to produce acid (Cheng et al. 2012a; Cheng et al. 2012b). Subsequently, the BPW solutions were stored for lactate analysis. The disks with biofilms were then transferred into tubes with 2 mL CPW, and the biofilms were harvested by sonication and vortexing at the maximum speed for 20 seconds using a vortex mixer (Fisher, Pittsburgh, Pa.). Three types of agar plates were used to measure the CFU counts to assess the microorganism viability (Cheng et al. 2012b). First, tryptic soy blood agar culture plates were used to determine total microorganisms. Second, (MSA) culture plates containing 15% sucrose were used to determine total streptococci (Lima et al. 2009). Third, MSA agar culture plates plus 0.2 units of bacitracin per mL was used to determine *mutans* streptococci.

The lactate concentrations in the BPW solutions were determined using an enzymatic (lactate dehydrogenase) method (Cheng et al. 2012a; Cheng et al. 2012b). A microplate reader (SpectraMax M5) was used to measure the absorbance at 340 nm (optical density $OD_{340}$) for the collected BPW solutions. Standard curves were prepared using a lactic acid standard (Supelco, Bellefonte, Pa.) (Cheng et al. 2012a; Cheng et al. 2012b).

Dentin Shear Bond Strength

The use of extracted human teeth was approved by the University of Maryland. Caries-free molars were cleaned and stored in 0.01% thymol solution. Flat mid-coronal dentin surfaces were prepared by cutting off the tips of crowns with a diamond saw (Isomet, Buehler, Lake Bluff, Ill.). Each tooth was embedded in a poly-carbonate holder (Bosworth, Skokie, Ill.) and ground perpendicular to the longitudinal axis on 320-grit silicon carbide paper until the occlusal enamel was removed. The dentin surface was etched with 37% phosphoric acid gel for 15 s and rinsed with water for 15 s (Antonucci et al. 2009). A primer was applied with a brush-tipped applicator and rubbed in for 15 s. The solvent was removed with a stream of air for 5 s. An adhesive was applied and light-cured for 10 s (Optilux). A stainless-steel iris, having a central opening with a diameter of 4 mm and a thickness of 1.5 mm, was held against the adhesive-treated dentin surface. The opening was filled with a composite (TPH) and light-cured for 60 s (Antonucci et al. 2009). The bonded specimens were stored in water at 37° C. for 24 h. A chisel connected with a Universal Testing Machine (MTS, Eden Prairie, Minn.) was aligned to be parallel to the composite-dentin interface (Cheng et al. 2012b; Antonucci et al. 2009). The load was applied at a rate of 0.5 mm/min until the bond failed. Dentin shear bond strength, $S_D$, was calculated as: $S_D=4P/(\pi d^2)$, where P is the load at failure, and d is the diameter of the composite. Ten teeth were tested for each group (n=10) (Cheng et al. 2012b; Antonucci et al. 2009).

Statistical Analyses

One-way analysis of variance (ANOVA) was performed to detect the significant effects of the variables. Tukey's multiple comparison test was used to compare the data at a p value of 0.05.

Results

The MIC and MBC results are plotted in FIG. 22. A low concentration needed to inhibit the bacteria indicates a high potency for the antibacterial agent. The new DMAHM was more strongly antibacterial than the previously-synthesized QADM, requiring a lower concentration, by an order of magnitude, to achieve the same bacteria-inhibitory effect. The new DMADDM was even more potent than DMAHM. The MIC and MBC of DMADDM was three orders of magnitude lower than those of MDAHM, and four orders of magnitude lower than QADM. The MIC and MBC of DMADDM approached those of CHX control.

The ADT results for un-cured primers are shown in FIG. 23. In (A), the commercial control primer had a minimal inhibition zone, as expected. Incorporation of QADM, DMAHM and DMADDM significantly increased the inhibition zone size. In (B-D), the primer with DMADDM had significantly larger inhibition zones than the primers with DMAHM and QADM (p<0.05). Incorporating 0.1% NAg into the primer with DMADDM further increased the inhibition zone size, which was about 10-fold those of the SBMP control primer (p<0.05).

The biofilm setup schematic and metabolic activity are shown in FIG. 24. In FIG. 24A, the biofilm was adherent on the cured primer covering the adhesive and the composite. In FIG. 24B, the biofilm was on the adhesive covering the composite without a primer, for the purpose of testing the antibacterial properties of the adhesive. In FIG. 24C, the first three groups followed the setup in FIG. 24A, groups 4 and 5 followed the setup in FIG. 24B, and the last group also followed FIG. 24A. The MTT results (mean±sd; n=6) in FIG. 24C showed that biofilms on SBMP had a high metabolic activity. Incorporation of DMADDM and NAg into the primer greatly reduced the metabolic activity (p<0.05). Similarly, incorporating DMADDM and NAg into the adhesive also reduced the metabolic activity. In the last group, with both primer and adhesive being antibacterial, the lowest metabolic activity was achieved. A&P+DMADDM+NAg yielded a biofilm metabolic activity that was about 20-fold lower than that of commercial bonding agent control.

FIG. 25 plots the CFU counts for: (A) Total microorganisms, (B) total streptococci, and (C) *mutans* streptococci (mean±sd; n=6). The values are shown in a log scale. Incorporation of DMADDM into the primer greatly reduced all three CFU counts, compared to the control group (p<0.05). Combining DMADDM with NAg in the primer significantly decreased the CFU than that using DMADDM alone (p<0.05). The same trend was observed when DMADDM and NAg were incorporated into the adhesive.

The lactic acid production by biofilms is plotted in FIG. 26 (mean±sd; n=6). Biofilms on commercial control primer produced the most lactic acid. Adding 5% of DMADDM in either primer or adhesive greatly reduced acid production, comparing to the control (p<0.05). Using DMADDM+NAg had a significantly stronger acid-inhibiting effect than using DMADDM alone (p<0.05). Adding DMADDM+NAg in both the primer and the adhesive further reduced lactic acid production (p<0.05). The lactic acid production by biofilms on P&A+DMADDM+NAg was approximately 1/20 of that on the commercial bonding agent.

FIG. 27 plots the dentin shear bond results (mean±sd; n=10). The six groups had shear bond strengths that were not significantly different from each other (p>0.1). This indicates that incorporation of the new quaternary ammonium monomer DMADDM and NAg into primer and adhesive to obtain antibacterial activity did not adversely affect the dentin shear bond strength.

All documents, books, manuals, papers, patents, published patent applications, guides, abstracts and other reference materials cited herein are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

CITED DOCUMENTS

Antonucci J M, O'Donnell J N, Schumacher G E, Skrtic D (2009). Amorphous calcium phosphate composites and their effect on composite-adhesive-dentin bonding. *J Adhes Sci Technol* 23:1133-1147.

Antonucci J M, Zeiger D N, Tang K, Lin-Gibson S, Fowler B O, Lin N J (2012). Synthesis and characterization of dimethacrylates containing quaternary ammonium functionalities for dental applications. *Dent Mater* 28:219-228.

Bayne S C, Thompson J Y, Swift Jr. E J, Stamatiades P, Wilkerson M (1998). A characterization of first-generation flowable composites. *J Am Dent Assoc* 129:567-577.

Burne R A (1998). Oral Streptococci . . . Products of their environment. *J Dent Res* 77:445-452.

Carlén A, Nikdel K, Wennerberg A, Holmberg K, Olsson J (2001). Surface characteristics and in vitro biofilm formation on glass ionomer and composite resin. *Biomaterials* 22:481-487.

Cenci M S, Pereira-Cenci T, Cury J A, ten Cate J M (2009). Relationship between gap size and dentine secondary caries formation assessed in a microcosm biofilm model. *Caries Res* 43:97-102.

Chai Z, Li F, Fang M, Wang Y, Ma S, Xiao Y, Huang L, Chen J (2011). The bonding property and cytotoxicity of a dental adhesive incorporating a new antibacterial monomer. *Oral Rehab* 38:849-856.

Cheng L, Exterkate R A, Zhou X, Li J, ten Cate J M (2011). Effect of galla *chinensis* on growth and metabolism of microcosm biofilms. *Caries Res* 45:87-92.

Cheng L, Weir M D, Xu H H K, Antonucci J M, Kraigsley A M, Lin N J, Lin-Gibson S, Zhou X D (2012a). Antibacterial amorphous calcium phosphate nanocomposite with quaternary ammonium salt and silver nanoparticles. *Dent Mater* 28:561-572

Cheng L, Zhang K, Melo M A S, Weir M D, Zhou X D, Xu H H K (2012b). Anti-biofilm dentin primer with quaternary ammonium and silver nanoparticles. *J Dent Res* 91:598-604.

Cheng L, Weir M D, Zhang K, Xu S M, Q Chen, Zhou X D, Xu H H K (2012c). Antibacterial nanocomposite with calcium phosphate and quaternary ammonium. *J Dent Res* 91:460-466.

Cheng Y J, Zeiger D N, Howarter J A, Zhang X, Lin N J, Antonucci J M, Lin-Gibson S (2011). In situ formation of silver nanoparticles in photocrosslinking polymers. *J Biomed Mater Res B* 97:124-131.

Chow L C, Sun L, Hockey B (2004). Properties of nano-structured hydroxyapatite prepared by a spray drying technique. *J Res NIST* 109:543-551.

Deng D M, ten Cate J M (2004). Demineralization of dentin by *Streptococcus mutans* biofilms grown in the constant depth film fermentor. *Caries Res* 38:54-61.

Deng D M, van Loveren C, ten Cate J M (2005). Caries-preventive agents induce remineralization of dentin in a biofilm model. *Caries Res* 39:216-223.

Deligeorgi V, Mjor I A, Wilson N H (2001). An overview of reasons for the placement and replacement of restorations. *Prim Dent Care* 8:5-11.

Drummond J L, Bapna M S (2003). Static and cyclic loading of fiber-reinforced dental resin. *Dent Mater* 19:226-231.

Drummond J L (2008). Degradation, fatigue, and failure of resin dental composite materials. *J Dent Res* 87:710-719.

Featherstone J D B (2000). The science and practice of caries prevention. *J Am Dent Assoc* 131:887-899.

Featherstone J D B (2004). The continuum of dental caries—Evidence for a dynamic disease process. *J Dent Res* 83: C39-C42.

Ferracane J L (1995). Current trends in dental composites. *Crit Rev Oral Biol Med* 6:302-318.

Frost P M (2002). An audit on the placement and replacement of restorations in a general dental practice. *Prim Dent Care* 9:31-36.

Hildebrandt G H, Bretz W A (2006). Comparison of culture media and chairside assays for enumerating *mutans* streptococci. *J Appl Microbiol* 100:1339-1347.

Huang L, Xiao Y H, Xing X D, Li F, Ma S, Qi L L, Chen J (2011). Antibacterial activity and cytotoxicity of two novel cross-linking antibacterial monomers on oral pathogens. *Arch Oral Biol* 56:367-373.

Imazato S (2003). Review: Antibacterial properties of resin composites and dentin bonding systems. *Dent Mater* 19:449-457.

Imazato S, Ehara A, Torii M, Ebisu S (1998). Antibacterial activity of dentine primer containing MDPB after curing. *J Dent* 26:267-271.

Imazato S, Kuramoto A, Takahashi Y, Ebisu S, Peters M C (2006). In vitro antibacterial effects of the dentin primer of Clearfil Protect Bond. *Dent Mater* 22:527-532.

Imazato S, Tay F R, Kaneshiro A V, Takahashi Y, Ebisu S (2007). An in vivo evaluation of bonding ability of comprehensive antibacterial adhesive system incorporating MDPB. *Dent Mater* 23:170-176.

Imazato S, Torii M, Tsuchitani Y, McCabe J F, Russell R R B (1994). Incorporation of bacterial inhibitor into resin composite. *J Dent Res* 73; 1437-1443.

Krämer N, García-Godoy F, Reinelt C, Frankenberger R (2006). Clinical performance of posterior compomer restorations over 4 years. *Am J Dent* 19:61-66.

Li F, Chen J, Chai Z, Zhang L, Xiao Y, Fang M, Ma S. Effects of a dental adhesive incorporating antibacterial monomer on the growth, adherence and membrane integrity of *Streptococcus mutans*. J Dent 2009; 37:289-296.

Lim B S, Ferracane J L, Sakaguchi R L, Condon J R (2002). Reduction of polymerization contraction stress for dental composites by two-step light-activation. *Dent Mater* 18:436-444.

Lima J P, Sampaio de Melo M A, Borges F M, Teixeira A H, Steiner-Oliveira C, Nobre Dos Santos M, et al (2009). Evaluation of the antimicrobial effect of photodynamic antimicrobial therapy in an in situ model of dentine caries. *Eur J Oral Sci.* 117:568-74.

Loesche W J (1986). Role of *Streptococcus mutans* in human dental decay. *Microbiological Reviews* 50:353-380.

Lu H, Stansbury J W, and C. N. Bowman C N (2005). Impact of curing protocol on conversion and shrinkage stress. *J Dent Res* 84:822-826.

Menschutkin, N. Z (1890). *Physik. Chemie* 5, 589.

McBain A J (2009). In vitro biofilm models: an overview. *Adv Appl Microbiol* 69:99-132.

McBain A J, Sissons C, Ledder R G, Sreenivasan P K, De Vizio W, Gilbert P (2005). Development and characterization of a simple perfused oral microcosm. *J Appl Microbiol* 98:624-634.

Mjör I A, Moorhead J E, Dahl J E (2000). Reasons for replacement of restorations in permanent teeth in general dental practice. *International Dent J* 50:361-366.

Moreau J L, Sun L, Chow L C, Xu H H K (2011). Mechanical and acid neutralizing properties and inhibition of bacterial growth of amorphous calcium phosphate dental nanocomposite. J Biomed Mater Res Part B 2011; 98: 80-88.

Park J, Ye Q, Topp E, Misra A, Kieweg S L, Spencer P (2009). Water sorption and dynamic mechanical properties of dentin adhesives with a urethane-based multifunctional methacrylate monomer. *Dent Mater* 25:1569-1575.

Park J H, Tanabe Y, Tinanoff N, Turng B F, Lilli H, Minah G E (2006). Evaluation of microbiological screening systems using dental plaque specimens from young children aged 6-36 months. *Caries Res.* 40:277-80.

Ruddell D E, M. M. Maloney M M, Thompson J Y (2002). Effect of novel filler particles on the mechanical and wear properties of dental composites. *Dent Mater* 18:72-80.

Sakaguchi R L (2005). Review of the current status and challenges for dental posterior restorative composites: clinical, chemistry, and physical behavior considerations. *Dent Mater* 21:3-6.

Sarrett D C (2005). Clinical challenges and the relevance of materials testing for posterior composite restorations. *Dent Mater* 21:9-20.

Stoodley P, Wefel J, Gieseke A, deBeer D, von Ohle C (2008). Biofilm plaque and hydrodynamic effects on mass transfer, fluoride delivery and caries. *J Am Dent Assoc* 139:1182-1190.

Svanberg M, Mjör I A, Orstavik D (1990). *Mutans* streptococci in plaque from margins of amalgam, composite, and glass-ionomer restorations. *J Dent Res* 69:861-864.

Takahashi Y, Imazato S, Russell R R B, Noiri Y, Ebisu S (2004). Influence of resin monomers on growth of oral streptococci. *J Dent Res* 83:302-306.

Totiam P, Gonzalez-Cabezas C, Fontana M R, Zero D T (2007). A new in vitro model to study the relationship of gap size and secondary caries. *Caries Res* 41:467-473.

van Houte J (1994). Role of micro-organisms in caries etiology. *J Dent Res* 73:672-681.

Watts D C, Marouf A S, Al-Hindi A M (2003). Photopolymerization shrinkage-stress kinetics in resin-composites: methods development. *Dent Mater* 19:1-11.

Xu H H K, Sun L, Weir M D, Antonucci J M, Takagi S, Chow L C (2006). Nano dicalcium phosphate anhydrous-whisker composites with high strength and Ca and $PO_4$ release. *J Dent Res* 85:722-727.

Xu H H K, Moreau J L, Sun L, Chow L C (2011). Nanocomposite containing amorphous calcium phosphate nanoparticles for caries inhibition. Dent Mater 27:762-769.

Zero D T (1995). In situ caries models. *Adv Dent Res* 9:214-230.

Zhang K, Melo M A S, Cheng L, Weir M D, Bai Y X, Xu H H K (2012). Effect of quaternary ammonium and silver nanoparticle-containing adhesives on dentin bond strength and dental plaque microcosm biofilms. *Dent Mater* 28:842-852.

What is claimed is:

1. A dental bonding system comprising (i) a dental primer and (ii) a dental adhesive, wherein the dental primer comprises a primer and one or more antibacterial agents and wherein the dental adhesive comprises an adhesive and one or more antibacterial agents, wherein one or more of the antibacterial agents of the dental primer and/or the dental adhesive is an antibacterial monomer selected from the group consisting of dimethylamino hexyl methacrylate (DMAHM), dimethylamino heptyl methacrylate (DMAHPM), dimethylamino octyl methacrylate (DMAOM), dimethylamino nonyl methacrylate (DMANM), dimethylamino decyl methacrylate (DMADM), dimethylamino undecyl methacrylate (DMAUDM), dimethylamino dodecyl methacrylate (DMADDM), dimethylamino tridecyl methacrylate (DMATDM), dimethylamino tetradecyl methacrylate (DMATTDM), dimethylamino pentadecyl methacrylate (DMAPDM), dimethylamino hexadecyl methacrylate (DMAHDM), dimethylamino heptadecyl methacrylate (DMAHPDM), dimethylamino octadecyl methacrylate (DMAODM), dimethylamino nonadecyl methacrylate (DMANDM), dimethylamino icosyl methacrylate (DMAIOM), dimethylamino henicosyl methacrylate (DMAHOM), and dimethylamino docosyl methacrylate (DMADOM).

2. The dental bonding system of claim 1, wherein the primer comprises one or more primers selected from the group consisting of bisphenol A diglycidyl methacrylate (Bis-GMA), glycerol dimethacrylate (GDMA), 2-hydroxyethyl methacrylate (HEMA), mono-2-methacryloyloxyethyl phthalate (MMEP), methacrylic acid (MA), methyl methacrylate (MMA), 4-acryloyloxyethyl trimellitate anhydride (4-AETA), N-phenylglycine glycidyl methacrylate (NPG-GMA), N-tolylglycine glycidyl methacrylate or N-(2-hydroxy-3-((2-methyl-1-oxo-2-propenyl)oxy)propyl)-N-tolyl glycine (NTG-GMA), pyromellitic diethylmethacrylate or 2,5-dimethacryloyloxyethyloxycarbonyl-1,4-benzenedicarboxylic acid (PMDM), pyromellitic glycerol dimethacrylate or 2,5-bis(1,3-dimethacryloyloxyprop-2-yloxycarbonyl)benzene-1,4-dicarboxylic acid (PMGDM), and triethylene glycol dimethacrylate (TEGDMA).

3. The dental bonding system of claim 1, wherein the primer comprises (a) 35-45% 2-hydroxyethylmethacrylate (HEMA), 10-20% copolymer of acrylic and itaconic acids, 40-50% water, or the primer comprises (b) PMGDM/HEMA at 3.3/1 ratio+1% BAPO+50% acetone.

4. The dental bonding system of claim 1, wherein the adhesive comprises one or more adhesives selected from the group consisting of ethoxylated bisphenol A glycol dimethacrylate (Bis-EMA), bisphenol A diglycidyl methacrylate (Bis-GMA), 2-hydroxyethyl methacrylate (HEMA), triethylene glycol dimethacrylate (TEGDMA), urethane dimethacrylate (UDMA), 4-methacryloyloxyethyl trimellitate anhydride (4-META), methacrylic acid (MA), methyl methacrylate (MMA), 4-acryloyloxyethyl trimellitate anhydride (4-AETA), ethyleneglycol dimethacrylate (EGDMA), glycerol dimethacrylate (GDMA), glycerol phosphate dimethacrylate (GPDM), pyromellitic glycerol dimethacrylate or 2,5-bis(1,3-dimethacryloyloxyprop-2-yloxycarbonyl)benzene-1,4-dicarboxylic acid (PMGDM).

5. The dental bonding system of claim 1, wherein the adhesive comprises (a) 60-70% BisGMA and 30-40% HEMA, or the adhesive comprises (b) BisGMA/TEGMA at 7/3 ratio+1% BAPO.

6. The dental bonding system of claim 1, wherein a further antibacterial agent present in the dental primer is selected from the group consisting of, silver-containing nanoparticles (NAg), quaternary ammonium salts (QAS), chlorhexidine particles, TiO2 particles and ZnO particles, and wherein a further antibacterial agent present in the dental adhesive is selected from the group consisting of, silver-containing nanoparticles (NAg), quaternary ammonium salts (QAS), chlorhexidine particles, TiO2 particles and ZnO particles.

7. The dental bonding system of claim 1, wherein when the antibacterial monomers are selected from the group consisting of DMADDM, DMATDM, DMATTDM, DMAPDM and DMAHDM.

8. The dental bonding system of claim 1, wherein the combined amount of antibacterial monomers present in the dental primer or the dental adhesive ranges from about 2.5% to about 12.5% of the mass of the dental primer or the dental adhesive.

9. The dental bonding system of claim 6, wherein when the one or more antibacterial agents include NAg, NAg is present in the dental primer or the dental adhesive in an amount ranging from about 0.05% to about 1% of the mass of the dental primer or the dental adhesive.

10. The dental bonding system of claim 6, wherein when the one or more antibacterial agents include QAS, QAS is present in the dental primer or the dental adhesive in an amount ranging from about 3% to about 15% of the mass of the dental primer or the dental adhesive.

11. The dental bonding system of claim 1, wherein the dental primer or the dental adhesive, or both, further comprises a remineralizing agent.

12. The dental bonding system of claim 11, wherein the remineralizing agent is nanoparticles of amorphous calcium phosphate (NACP) present in the dental primer or the dental adhesive in an amount ranging from about 5% to about 45% of the dental primer or the dental adhesive.

13. The dental bonding system of claim 1, wherein the dental bonding system is a two-component dental bonding system, a three-step dental bonding system, a two-step dental bonding system or a one-step self-adhesive bonding system.

14. The dental bonding system of claim 7, wherein the combined amount of antibacterial monomers present in the dental primer or the dental adhesive ranges from about 2.5% to about 12.5% of the mass of the dental primer or the dental adhesive.

* * * * *